US010202587B2

(12) United States Patent
Chabriere et al.

(10) Patent No.: US 10,202,587 B2
(45) Date of Patent: Feb. 12, 2019

(54) VULCANISAETAL PHOSPHOTRIESTERASE-LIKE LACTONASES (PLL) HAVING ENHANCED PROPERTIES AND THE USES THEREOF

(71) Applicants: CENTRE NATIONAL DE LA RECHERCHE SCIENTIFIQUE, Paris (FR); UNIVERSITE D'AIX-MARSEILLE, Marseilles (FR)

(72) Inventors: Eric Chabriere, Marseilles (FR); Mikael Elias, Florange (FR); Julien Hiblot, Prilly (CH); Didier Raoult, Marseilles (FR)

(73) Assignees: CENTRE NATIONAL DE LA RECHERCHE SCIENTIFIQUE, Paris (FR); UNIVERSITE D'AIX-MARSEILLE, Marseilles (FR)

( * ) Notice: Subject to any disclaimer, the term of this patent is extended or adjusted under 35 U.S.C. 154(b) by 199 days.

(21) Appl. No.: 14/905,157

(22) PCT Filed: Jul. 31, 2014

(86) PCT No.: PCT/EP2014/066563
§ 371 (c)(1),
(2) Date: Jan. 14, 2016

(87) PCT Pub. No.: WO2015/014971
PCT Pub. Date: Feb. 5, 2015

(65) Prior Publication Data
US 2016/0237413 A1   Aug. 18, 2016

(30) Foreign Application Priority Data
Jul. 31, 2013   (EP) ..................... 13306109

(51) Int. Cl.
| | |
|---|---|
| A62D 3/02 | (2007.01) |
| C12N 9/16 | (2006.01) |
| C11D 3/386 | (2006.01) |
| A61K 38/46 | (2006.01) |
| C11D 3/48 | (2006.01) |
| C12N 9/18 | (2006.01) |
| A62D 101/02 | (2007.01) |
| A62D 101/04 | (2007.01) |
| A62D 101/26 | (2007.01) |

(52) U.S. Cl.
CPC .............. *C12N 9/16* (2013.01); *A61K 38/465* (2013.01); *A62D 3/02* (2013.01); *C11D 3/38636* (2013.01); *C11D 3/48* (2013.01); *C12N 9/18* (2013.01); *A62D 2101/02* (2013.01); *A62D 2101/04* (2013.01); *A62D 2101/26* (2013.01); *C12Y 301/01* (2013.01); *C12Y 301/08001* (2013.01)

(58) Field of Classification Search
None
See application file for complete search history.

(56) References Cited

U.S. PATENT DOCUMENTS 8,372,618 B2 *   2/2013   Chabriere ............... C12N 9/16
435/174

FOREIGN PATENT DOCUMENTS

WO   WO-2008145865 A2 * 12/2008 ............... C12N 9/16

OTHER PUBLICATIONS

Julien Hiblot et al., Characterisation of the organophosphate hydrolase catalytic activity of SsoPox, (2012) Sci Rep 2: 779.
Asael Herman et al., (2007) Incorporating Synthetic Oligonucleotides via Gene Reassembly (ISOR): a versatile tool for generating targeted libraries. Protein Engineering, Design & Selection; vol. 20 No. 5: 219-226.
F. William Studier., (2005) Protein production by auto-induction in high density shaking cultures. Protein Expression and Purification 41: 207-234.
Guillaume Gotthard et al., (2011) Crystallization and preliminary X-ray diffraction analysis of the hyperthermophilic Sulfolobus islandicus lactonase. Acta Crystallographica Section F, Structural Biology and Crystallization Communications 67: 354-357.
Pompea Del Vecchio et al., (2009) Structural determinants of the high thermal stability of SsoPox from the hyperthermophilic archaeon Sulfolobus solfataricus. Extremophiles 13: 461-470.
Julien Hiblot et al., (2012) Structural and Enzymatic characterization of the lactonase SisLac from Sulfolobus islandicus. PLos One 7: e47028.
Y. Ashani et al., (2010) Stereo-specific synthesis of analogs of nerve agents and their utilization for selection and characterization of paraoxonase (PON1) catalytic scavengers. Chem Biol Interact. 187: 362-369.
Nimmy Augustine et al., (2010) Inhibition of Vibrio cholerae biofilm by AiiA enzyme produced from *Bacillus* spp. Arch Microbiol 192: 1019-1022.
Tu-Chen Cheng et al., Purification and Properties of a Highly Active Organophosphorus Acid Anhydrolase from Alteromonas undina. Applied and Environmental Microbiology, Sep. 1993, p. 3138-3140.
Yi-Hu Dong et al., Quenching quorum-sensing-dependent bacterial infection by an N-acyl homoserine lactonase. Nature, Jun. 14, 2001, vol. 411; 813-817.
Vadim M. Gumerov et al., Complete Genome Sequence of "Vulcanisaeta moutnovskia" Strain 768-28, a Novel Member of the Hyperthermophilic Crenarchaeal Genus *Vulcanisaeta*. Journal of Bacteriology, May 2011, vol. 193, No. 9, p. 2355-2356.

(Continued)

*Primary Examiner* — Anand U Desai
(74) *Attorney, Agent, or Firm* — Young & Thompson

(57) ABSTRACT

Provided is a mutated hyperthermophilic PTE having a lactonase activity derived from a hyperthermophilic phosphotriesterase corresponding to the consensus sequence of SEQ ID NO: 1, the mutated PTE including the at least one mutation chosen amongst 55 putative positions and the mutated PTE having enhanced properties. Also provided are compositions including the mutated hyperthermophilic PTE and the uses thereof, notably as bioscavenger of organophosphate compounds or as quorum quencher of the bacteria using lactones to communicate.

15 Claims, 1 Drawing Sheet
Specification includes a Sequence Listing.

(56) References Cited

OTHER PUBLICATIONS

Morten Hentzer et al., (2003) Attenuation of Pseudomonas aeruginosa virulence by quorum sensing inhibitors. The EMBO Journal. vol. 22, No. 15, pp. 3803-3815.

Luigia Merone et al.: "Improving the promiscuous nerve agent hydrolase activity of a thermostable archaeal lactonase.", Bioresource Technology Dec. 2010, vol. 101, No. 23, pp. 9204-9212, XP002717427.

Fang Ma et al., (2009) Heterologous expression of human paraoxonases in Pseudomonas aeruginosa inhibits biofilm formation and decreases antibiotic resistance. Appl Microbiol Biotechmol. 83: 135-141.

Konstantinos Mavromatis et al., (2010) Complete genome sequence of Vulcanisaeta distributa type strain (IC-017T). Standards in Genomic Sciences. 3: 117-125.

Suzanne A. Mckeon et al., Functional Quorum Sensing Systems are Maintained during Chronic Burkholderia cepacia Complex Infections in Patients with Cystic Fibrosis. Quorum Sensing in Bcc Chronic CF Isolates. JID 2010: 203 (Feb. 1) p. 383-392.

Roman Popat et al., The social behaviours of bacterial pathogens. British Medical Bulletin 2008; 87: 63-75.

Lily Raven et al., (1993) Human Butyrylcholinesterase as a General Prophylactic Antidote for Nerve Agent Toxicity. Biochemical Pharmacology, vol. 45, No. 12, pp. 2465-2474.

Yumiko Sakuragi et al., Quorum-Sensing Regulation of the Biofilm Matrix Genes (pel) of Pseudomonas aeruginosa. Journal of Bacteriology, Jul. 2007, vol. 189, No. 14, p. 5383-5386.

Danielle M. Stacy et al., Attenuation of quorum sensing in the pathogen Acinetobacter baumannii using non-native N-acyl homoserine lactones. National Institutes of Health. ACS Chem Biol. Author manuscript; Oct. 19, 2013, p. 1-20.

XP-002717425, http://ibis/exam/dbfetch.jsp?id=UNIPROT:F0QXN6 (May 12, 2013).

Guishan Zhang et al., Acyl homoserine lactone-based quorum sensing in a methanogenic archaeon. The ISME Journal (2012) 6, 1336-1344.

\* cited by examiner ical Bulletin, 87: 63-75). This link

SEQUENCE LISTING

```
<160> NUMBER OF SEQ ID NOS: 255

<210> SEQ ID NO 1
<211> LENGTH: 316
<212> TYPE: PRT
<213> ORGANISM: Vulcanisaeta moutnovskia

<400> SEQUENCE: 1

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270
```

Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
        290                 295                 300

Leu Ile Asp Asn Pro Arg Arg Leu Phe Thr Gly Arg
305                 310                 315

<210> SEQ ID NO 2
<211> LENGTH: 948
<212> TYPE: DNA
<213> ORGANISM: Vulcanisaeta moutnovskia

<400> SEQUENCE: 2

```
atggtgcgta ttagcattgc cggtggtaat gaaattgatc cgggtagcat gggtctgacc     60
ctgtttcatg aacatctgcg tctgattacc gaagttgttc gttggaattg gcctcatctg    120
tataacgaag atgaagaact gaaacgtgca attgatgcag ttaacgcagc aaaaaatac     180
ggcgtgaaaa ccattattga tctgaccgtt gcaggtattg gttgtgatgt cgctttaat     240
gaaaaagttg caaaagccac cggtgtgaac attattatgg caccggtttt ttatacctat    300
accgaaatcc cgttctattt caaaaaccgt ggtattgata gcctggttga tgcctttgtt    360
catgatatta ccattggtat tcagggcacc aatacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa agcagcctg    540
gatctgatcc gcattttcaa gaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgatt ggtatccgcc tgaagttgtg cgtagcaccg ttccggattg gaccatgacc    840
ctgattttg agaaagttat tccgcgtatg cgtagcgaag gtattacgga gaacaaatt    900
aatcgcgtgc tgattgataa tccgcgtcgt ctgtttaccg gtcgttaa                948
```

<210> SEQ ID NO 3
<211> LENGTH: 315
<212> TYPE: PRT
<213> ORGANISM: Vulcanisaeta moutnovskia

<400> SEQUENCE: 3

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln

```
                    115                 120                 125
Gly Thr Asn Thr Arg Ala Ala Phe Val Lys Ala Val Ile Asp Ser Ser
                130                 135                 140
Gly Leu Thr Lys Asp Val Glu Met Ala Ile Arg Ala Ala Lys Ala
145                 150                 155                 160
His Ile Lys Thr Asp Val Pro Ile Ile Thr His Ser Phe Val Gly Asn
                165                 170                 175
Lys Ser Ser Leu Asp Leu Ile Arg Ile Phe Lys Glu Glu Gly Val Asp
                180                 185                 190
Leu Ala Arg Thr Val Ile Gly His Val Gly Asp Thr Asp Asp Ile Ser
                195                 200                 205
Phe Ile Glu Gln Ile Leu Arg Glu Gly Ala Phe Ile Gly Leu Asp Arg
                210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Ser His
                245                 250                 255
Asp Tyr Cys Pro Thr Ile Asp Trp Tyr Pro Glu Val Val Arg Ser
                260                 265                 270
Thr Val Pro Asp Trp Thr Met Thr Leu Ile Phe Glu Lys Val Ile Pro
                275                 280                 285
Arg Met Arg Ser Glu Gly Ile Thr Glu Glu Gln Ile Asn Arg Val Leu
                290                 295                 300
Ile Asp Asn Pro Arg Arg Leu Phe Thr Gly Arg
305                 310                 315

<210> SEQ ID NO 4
<211> LENGTH: 948
<212> TYPE: DNA
<213> ORGANISM: Vulcanisaeta moutnovskia

<400> SEQUENCE: 4
atggtgcgta ttagcattgc cggtggtaat gaaattgatc cgggtagcat gggtctgacc      60
ctgtttcatg aacatctgcg tctgattacc gaagttgttc gttggaattg cctcatctg     120
tataacgaag atgaagaact gaaacgtgca attgatgcag ttaacgcagc caaaaaatac     180
ggcgtgaaaa ccattattga tctgaccgtt gcaggtattg ttgtgatgt tcgctttaat     240
gaaaaagttg caaaagccac cggtgtgaac attattatgg caccggtttt ttatacctat     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa agcagcctg     540
gatctgatcc gcattttcaa agaagaaggc gttgatctgg cacgtaccgt tattggtcat     600
gttggtgata ccgatgatat cagctttatt gagcagattc tgcgtgaagg tgcatttat     660
ggtctggatc gttttggcct ggatatttat ctgccgctgg ataaacgtgt taaaaccgca     720
attgaactga ttaaacgcgg ttggattgat cagctgctgc tgagccatga ttattgtccg     780
accattgatt tttatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                  948
```

<210> SEQ ID NO 5
<211> LENGTH: 315
<212> TYPE: PRT
<213> ORGANISM: Vulcanisaeta moutnovskia

<400> SEQUENCE: 5

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Phe Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 6
<211> LENGTH: 948
<212> TYPE: DNA
<213> ORGANISM: Vulcanisaeta moutnovskia

<400> SEQUENCE: 6
atggtgcgta ttagcattgc cggtggtaat gaaattgatc cgggtagcat gggtctgacc    60
ctgtttcatg aacatctgcg tctgattacc gaagttgttc gttggaattg gcctcatctg   120

-continued

```
tataacgaag atgaagaact gaaacgtgca attgatgcag ttaacgcagc caaaaatac    180
ggcgtgaaaa ccattattga tctgaccgtt gcaggtattg ttgtgatgt tcgctttaat    240
gaaaaagttg caaaagccac cggtgtgaac attattatgg caccggtttt ttatacctat    300
accgaaatcc cgttctattt caaaaaccgt ggtattgata gcctggttga tgcctttgtt    360
catgatatta ccattggtat tcagggcacc aatacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa aagcagcctg    540
gatctgatcc gcattttcaa agaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgata tgtatccgcc tgaagttgtg cgtagcaccg ttccggattg gaccatgacc    840
ctgatttttg agaaagttat tccgcgtatg cgtagcgaag gtattacgga agaacaaatt    900
aatcgcgtgc tgattgataa tccgcgtcgt ctgtttaccg gtcgttaa                 948
```

<210> SEQ ID NO 7
<211> LENGTH: 315
<212> TYPE: PRT
<213> ORGANISM: Vulcanisaeta moutnovskia

<400> SEQUENCE: 7

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
```

```
                225                 230                 235                 240
Ile Glu Leu Ile Lys Arg Gly Trp Ile Asp Gln Leu Leu Ser His
                    245                 250                 255

Asp Tyr Cys Pro Thr Ile Asp Met Tyr Pro Glu Val Val Arg Ser
                260                 265                 270

Thr Val Pro Asp Trp Thr Met Thr Leu Ile Phe Glu Lys Val Ile Pro
                275                 280                 285

Arg Met Arg Ser Glu Gly Ile Thr Glu Gln Ile Asn Arg Val Leu
            290                 295                 300

Ile Asp Asn Pro Arg Arg Leu Phe Thr Gly Arg
305                 310                 315

<210> SEQ ID NO 8
<211> LENGTH: 948
<212> TYPE: DNA
<213> ORGANISM: Vulcanisaeta moutnovskia

<400> SEQUENCE: 8
atggtgcgta ttagcattgc cggtggtaat gaaattgatc cgggtagcat gggtctgacc        60
ctgtttcatg aacatctgcg tctgattacc gaagttgttc gttggaattg gcctcatctg       120
tataacgaag atgaagaact gaaacgtgca attgatgcag ttaacgcagc caaaaaatac       180
ggcgtgaaaa ccattattga tctgaccgtt gcaggtattg gttgtgatgt cgctttaat        240
gaaaaagttg caaaagccac cggtgtgaac attattatgg caccggtttt ttatacctat       300
accgaaatcc cgttctattt caaaaaccgt ggtattgata gcctggttga tgcctttgtt       360
catgatatta ccattggtat tcagggcacc aatacccgtg cagcatttgt taaagcagtg       420
attgatagca gcggtctgac caaagatgtt gaaatggcaa ttcgtgcagc agcaaaagca       480
catatcaaaa ccgatgttcc gattatcacc catagctttg ttggtaataa agcagcctg        540
gatctgatcc gcatttttcaa agaagaaggc gttgatctgg cacgtaccgt tattggtcat       600
gttggtgata ccgatgatat cagctttatt gagcagattc tgcgtgaagg tgcatttatt       660
ggtctggatc gttttggcct ggatatttat ctgccgctgg ataaacgtgt taaaaccgca       720
attgaactga ttaaacgcgg ttggattgat cagctgctgc tgagccatga ttattgtccg       780
accattgatc tgtatccgcc tgaagttgtg cgtagcaccg ttccggattg gaccatgacc       840
ctgatttttg agaagttat tccgcgtatg cgtagcgaag gtattacgga agaacaaatt       900
aatcgcgtgc tgattgataa tccgcgtcgt ctgtttaccg gtcgttaa                    948

<210> SEQ ID NO 9
<211> LENGTH: 315
<212> TYPE: PRT
<213> ORGANISM: Vulcanisaeta moutnovskia

<400> SEQUENCE: 9

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
                20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
        50                  55                  60

Ile Ile Asp Leu Thr Val Ala Gly Ile Gly Cys Asp Val Arg Phe Asn
65                  70                  75                  80
```

```
Glu Lys Val Ala Lys Ala Thr Gly Val Asn Ile Ile Met Gly Thr Gly
                 85                  90                  95
Phe Tyr Thr Tyr Thr Glu Ile Pro Phe Tyr Phe Lys Asn Arg Gly Ile
            100                 105                 110
Asp Ser Leu Val Asp Ala Phe Val His Asp Ile Thr Ile Gly Ile Gln
            115                 120                 125
Gly Thr Asn Thr Arg Ala Ala Phe Val Lys Ala Val Ile Asp Ser Ser
130                 135                 140
Gly Leu Thr Lys Asp Val Glu Met Ala Ile Arg Ala Ala Ala Lys Ala
145                 150                 155                 160
His Ile Lys Thr Asp Val Pro Ile Ile Thr His Ser Phe Val Gly Asn
                165                 170                 175
Lys Ser Ser Leu Asp Leu Ile Arg Ile Phe Lys Glu Glu Gly Val Asp
            180                 185                 190
Leu Ala Arg Thr Val Ile Gly His Val Gly Asp Thr Asp Asp Ile Ser
            195                 200                 205
Phe Ile Glu Gln Ile Leu Arg Glu Gly Ala Phe Ile Gly Leu Asp Arg
210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Ser His
                245                 250                 255
Asp Tyr Cys Pro Thr Ile Asp Leu Tyr Pro Pro Glu Val Val Arg Ser
                260                 265                 270
Thr Val Pro Asp Trp Thr Met Thr Leu Ile Phe Glu Lys Val Ile Pro
            275                 280                 285
Arg Met Arg Ser Glu Gly Ile Thr Glu Glu Gln Ile Asn Arg Val Leu
290                 295                 300
Ile Asp Asn Pro Arg Arg Leu Phe Thr Gly Arg
305                 310                 315

<210> SEQ ID NO 10
<211> LENGTH: 948
<212> TYPE: DNA
<213> ORGANISM: Vulcanisaeta moutnovskia

<400> SEQUENCE: 10
atggtgcgta ttagcattgc cggtggtaat gaaattgatc cgggtagcat gggtctgacc    60
ctgtttcatg aacatctgcg tctgattacc gaagttgttc gttggaattg cctcatctg   120
tataacgaag atgaagaact gaaacgtgca attgatgcag ttaacgcagc caaaaaatac   180
ggcgtgaaaa ccattattga tctgaccgtt gcaggtattg ttgtgatgt tcgctttaat   240
gaaaaagttg caaaagccac cggtgtgaac attattatgg gcaccggttt ttatacctat   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattataccc atagctttg ttggtaataa agcagcctg   540
gatctgatcc gcattttcaa agaagaaggc gttgatctgg cacgtaccgt tattggtcat   600
gttggtgata ccgatgatat cagcttt att gagcagattc tgcgtgaagg tgcatttatt   660
ggtctggatc gttttggcct ggatatttat ctgccgctgg ataaacgtgt taaaaccgca   720
attgaactga ttaaacgcgg ttggattgat cagctgctgc tgagccatga ttattgtccg   780
```

```
accattgatg cgtatccgcc tgaagttgtg cgtagcaccg ttccggattg gaccatgacc    840 ctgattttg agaaagttat tccgcgtatg cgtagcgaag gtattacgga agaacaaatt    900
aatcgcgtgc tgattgataa tccgcgtcgt ctgtttaccg gtcgttaa                948
```

<210> SEQ ID NO 11
<211> LENGTH: 315
<212> TYPE: PRT
<213> ORGANISM: Vulcanisaeta moutnovskia

<400> SEQUENCE: 11

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Leu Lys
        35                  40                  45

Arg Ala Ile Asp Ala Val Asn Ala Ala Lys Lys Tyr Gly Val Lys Thr
50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Ala Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315
```

<210> SEQ ID NO 12
<211> LENGTH: 948
<212> TYPE: DNA

<213> ORGANISM: Vulcanisaeta moutnovskia

<400> SEQUENCE: 12

```
atggtgcgta ttagcattgc cggtggtaat gaaattgatc cgggtagcat gggtctgacc    60
ctgtttcatg aacatctgcg tctgattacc gaagttgttc gttggaattg gcctcatctg   120
tataacgaag atgaagaact gaaacgtgca attgatgcag ttaacgcagc caaaaaatac   180
ggcgtgaaaa ccattattga tctgaccgtt gcaggtattg gttgtgatgt tcgctttaat   240
gaaaaagttg caaaagccac cggtgtgaac attattatgg gcaccggttt ttatacctat   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa aagcagcctg   540
gatctgatcc gcattttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatttat ctgccgctgg ataaacgtgt taaaaccgca   720
attgaactga ttaaacgcgg ttggattgat cagctgctgc tgagccatga ttattgtccg   780
accattgata tttatccgcc tgaagttgtg cgtagcaccg ttccggattg gaccatgacc   840
ctgattttttg agaagttat ccgcgtatg cgtagcgaag gtattacgga agaacaaatt   900
aatcgcgtgc tgattgataa tccgcgtcgt ctgtttaccg gtcgttaa               948
```

<210> SEQ ID NO 13
<211> LENGTH: 315
<212> TYPE: PRT
<213> ORGANISM: Vulcanisaeta moutnovskia

<400> SEQUENCE: 13

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

```
Leu Ala Arg Thr Val Ile Gly His Val Gly Asp Thr Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Ile Tyr Pro Pro Glu Val Val Arg Ser
                260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Gln Ile Asn Arg Val Leu
    290                 295                 300

Ile Asp Asn Pro Arg Arg Leu Phe Thr Gly Arg
305                 310                 315

<210> SEQ ID NO 14
<211> LENGTH: 948
<212> TYPE: DNA
<213> ORGANISM: Vulcanisaeta moutnovskia

<400> SEQUENCE: 14
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaact gaaacgtgca attgatgcag ttaacgcagc caaaaaatac     180
ggcgtgaaaa ccattattga tctgaccgtt gcaggtattg ttgtgatgt cgctttaat      240
gaaaaagttg caaaagccac cggtgtgaac attattatgg gcaccggttt ttatacctat     300
accgaaatcc cgttctattt caaaaaccgt ggtattgata gcctggttga tgcctttgtt     360
catgatatta ccattggtat tcagggcacc aataccccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa agcagcctg     540
gatctgatcc gcattttcaa agaagaaggc gttgatctgg cacgtaccgt tattggtcat     600
gttggtgata ccgatgatat cagctttatt gagcagattc tgcgtgaagg tgcatttat      660
ggtctggatc gttttggcct ggatatttat ctgccgctgg ataaacgtgt taaaaccgca     720
attgaactga ttaaacgcgg ttggattgat cagctgctgc tgagccatga ttattgtccg     780
accattgatg tttatccgcc tgaagttgtg cgtagcaccg ttccggattg gaccatgacc     840
ctgattttgg agaagttat tccgcgtatg cgtagcgaag gtattacgga agaacaaatt     900
aatcgcgtgc tgattgataa tccgcgtcgt ctgtttaccg gtcgttaa              948

<210> SEQ ID NO 15
<211> LENGTH: 315
<212> TYPE: PRT
<213> ORGANISM: Vulcanisaeta moutnovskia

<400> SEQUENCE: 15

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30
```

Val Arg Trp Asn Trp Pro His Leu Tyr Asn Glu Asp Glu Leu Lys
 35                  40                  45

Arg Ala Ile Asp Ala Val Asn Ala Ala Lys Lys Tyr Gly Val Lys Thr
 50                  55                  60

Ile Ile Asp Leu Thr Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
            195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Val Tyr Pro Pro Glu Val Val Arg Ser
            260                 265                 270

Thr Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 16
<211> LENGTH: 948
<212> TYPE: DNA
<213> ORGANISM: Vulcanisaeta moutnovskia

<400> SEQUENCE: 16
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaact gaaacgtgca attgatgcag ttaacgcagc caaaaaatac     180
ggcgtgaaaa ccattattga tctgaccgtt gcaggtattg gttgtgatgt cgctttaat      240 gaaaaagttg caaaagccac cggtgtgaac attattatgg caccggtttt tataccat      300 accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa aagcagcctg     540

```
gatctgatcc gcattttcaa agaagaaggc gttgatctgg cacgtaccgt tattggtcat      600
gttggtgata ccgatgatat cagctttatt gagcagattc tgcgtgaagg tgcatttatt      660
ggtctggatc gttttggcct ggatatttat ctgccgctgg ataaacgtgt taaaaccgca      720
attgaactga ttaaacgcgg ttggattgat cagctgctgc tgagccatga ttattgtccg      780
accattgata cctatccgcc tgaagttgtg cgtagcaccg ttccggattg gaccatgacc      840 ctgattttttg agaaagttat tccgcgtatg cgtagcgaag gtattacgga agaacaaatt      900
aatcgcgtgc tgattgataa tccgcgtcgt ctgtttaccg gtcgttaa                   948
```

<210> SEQ ID NO 17
<211> LENGTH: 315
<212> TYPE: PRT
<213> ORGANISM: Vulcanisaeta moutnovskia
<400> SEQUENCE: 17

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300
```

Ile Asp Asn Pro Arg Arg Leu Phe Thr Gly Arg
305                 310                 315

<210> SEQ ID NO 18
<211> LENGTH: 948
<212> TYPE: DNA
<213> ORGANISM: Vulcanisaeta moutnovskia

<400> SEQUENCE: 18

```
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaact gaaacgtgca attgatgcag ttaacgcagc caaaaaatac     180
ggcgtgaaaa ccattattga tctgaccgtt gcaggtattg gttgtgatgt tcgctttaat     240
gaaaaagttg caaaagccac cggtgtgaac attattatgg gcaccggttt ttatacctat     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc atagctttg ttggtaataa aagcagcctg     540
gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcct ggatatttat ctgccgctgg ataaacgtgt taaaaccgca     720
attgaactga ttaaacgcgg ttggattgat cagctgctgc tgagccatga ttattgtccg     780
accattgatt gctatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                  948
```

<210> SEQ ID NO 19
<211> LENGTH: 315
<212> TYPE: PRT
<213> ORGANISM: Vulcanisaeta moutnovskia

<400> SEQUENCE: 19

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
            165                 170                 175

Lys Ser Ser Leu Asp Leu Ile Arg Ile Phe Lys Glu Glu Gly Val Asp
        180                 185                 190

Leu Ala Arg Thr Val Ile Gly His Val Gly Asp Thr Asp Asp Ile Ser
    195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Cys Tyr Pro Pro Glu Val Val Arg Ser
                260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 20
<211> LENGTH: 948
<212> TYPE: DNA
<213> ORGANISM: Vulcanisaeta moutnovskia

<400> SEQUENCE: 20
atggtgcgta ttagcattgc cggtggtaat gaaattgatc cgggtagcat gggtctgacc      60
ctgtttcatg aacatctgcg tctgattacc gaagttgttc gttggaattg cctcatctg     120 tataacgaag atgaagaatt gaaacgtgca attgatgcag ttaacgcagc caaaaaatac     180
ggcgtgaaaa ccattattga tctgaccgtt gcaggtattg ttgtgatgt tcgctttaat     240 gaaaaagttg caaaagccac cggtgtgaac attattatgg caccggtttt ttatacctat     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc atagctttg ttggtaataa agcagcctg     540 gatctgatcc gcattttcaa agaagaaggc gttgatctgg cacgtaccgt tattggtcat     600
gttggtgata ccgatgatat cagcttatt gagcagattc tgcgtgaagg tgcatttatt     660
ggtctggatc gttttggcct ggatatttat ctgccgctgg ataaacgtgt taaaaccgca     720
attgaactga ttaaacgcgg ttggattgat cagctgctgc tgagccatga ttatctgccg     780
acctttgatg catatccgcc tgaagttgtg cgtagcaccg ttccggattg gaccatgacc     840 ctgattttg agaaagttat tccgcgtatg cgtagcgaag gtattacgga agaacaaatt     900
aatcgcgtgc tgattgataa tccgcgtcgt ctgtttaccg gtcgttaa               948

<210> SEQ ID NO 21
<211> LENGTH: 315
<212> TYPE: PRT
<213> ORGANISM: Vulcanisaeta moutnovskia

<400> SEQUENCE: 21

| | | | | | | | | | | | | | | |
|---|---|---|---|---|---|---|---|---|---|---|---|---|---|---|
|Met|Val|Arg|Ile|Ser|Ile|Ala|Gly|Gly|Asn|Glu|Ile|Asp|Pro|Gly|Ser|
|1| | | |5| | | | |10| | | | |15|

Met Gly Leu Thr Leu Phe His Glu His Leu Arg Leu Ile Thr Glu Val
              20                         25                     30

Val Arg Trp Asn Trp Pro His Leu Tyr Asn Glu Asp Glu Glu Leu Lys
        35                        40                        45

Arg Ala Ile Asp Ala Val Asn Ala Ala Lys Lys Tyr Gly Val Lys Thr
50                          55                        60

Ile Ile Asp Leu Thr Val Ala Gly Ile Gly Cys Asp Val Arg Phe Asn
65                    70                    75                    80

Glu Lys Val Ala Lys Ala Thr Gly Val Asn Ile Ile Met Gly Thr Gly
              85                        90                    95

Phe Tyr Thr Tyr Thr Glu Ile Pro Phe Tyr Phe Lys Asn Arg Gly Ile
            100                      105                  110

Asp Ser Leu Val Asp Ala Phe Val His Asp Ile Thr Ile Gly Ile Gln
        115                      120                  125

Gly Thr Asn Thr Arg Ala Ala Phe Val Lys Ala Val Ile Asp Ser Ser
130                        135                    140

Gly Leu Thr Lys Asp Val Glu Met Ala Ile Arg Ala Ala Ala Lys Ala
145                    150                    155                  160

His Ile Lys Thr Asp Val Pro Ile Ile Thr His Ser Phe Val Gly Asn
              165                    170                  175

Lys Ser Ser Leu Asp Leu Ile Arg Ile Phe Lys Glu Glu Gly Val Asp
            180                      185                  190

Leu Ala Arg Thr Val Ile Gly His Val Gly Asp Thr Asp Asp Ile Ser
        195                      200                  205

Phe Ile Glu Gln Ile Leu Arg Glu Gly Ala Phe Ile Gly Leu Asp Arg
210                        215                    220

Phe Gly Leu Asp Ile Tyr Leu Pro Leu Asp Lys Arg Val Lys Thr Ala
225                    230                    235                  240

Ile Glu Leu Ile Lys Arg Gly Trp Ile Asp Gln Leu Leu Ser His
              245                    250                  255

Asp Tyr Leu Pro Thr Phe Asp Ala Tyr Pro Pro Glu Val Val Arg Ser
            260                      265                  270

Thr Val Pro Asp Trp Thr Met Thr Leu Ile Phe Glu Lys Val Ile Pro
        275                      280                  285

Arg Met Arg Ser Glu Gly Ile Thr Glu Glu Gln Ile Asn Arg Val Leu
290                        295                    300

Ile Asp Asn Pro Arg Arg Leu Phe Thr Gly Arg
305                    310                    315

<210> SEQ ID NO 22
<211> LENGTH: 948
<212> TYPE: DNA
<213> ORGANISM: Vulcanisaeta moutnovskia

<400> SEQUENCE: 22
atggtgcgta ttagcattgc cggtggtaat gaaattgatc cgggtagcat gggtctgacc    60
ctgtttcatg aacatctgcg tgcaattacc gaagttgttc gttggaattg gcctcatctg  120
tataacgaag atgaagaatt gaaacgtgca attgatgcag ttaacgcagc caaaaaatac  180
ggcgtgaaaa ccattattga tctgaccgtt gcaggtattg ttgtgatgt tcgctttaat  240 gaaaaagttg caaaagccac cggtgtgaac attattatgg caccggtttt ttggacctat  300

-continued

```
accgaaatcc cgttctattt caaaaaccgt ggtattgata gcctggttga tgcctttgtt    360
catgatatta ccattggtat tcagggcacc aatacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa agcagcctg    540
gatctgatcc gcattttcaa agaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatgtat ctgccgctgg ataaacgtgt taaaaccgca    720
attgaactga ttaaacgcgg ttggattgat cagctgctgc tgagccatga ttattgtccg    780
accattgata tgtatccgcc tgaagttgtg cgtagcaccg ttccggattg accatgacc    840
ctgattttg agaaagttat tccgcgtatg cgtagcgaag gtattacgga gaacaaatt    900
aatcgcgtgc tgattgataa tccgcgtcgt ctgtttaccg gtcgttaa               948
```

<210> SEQ ID NO 23
<211> LENGTH: 315
<212> TYPE: PRT
<213> ORGANISM: Vulcanisaeta moutnovskia

<400> SEQUENCE: 23

```
Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Met Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255
```

Asp Tyr Cys Pro Thr Ile Asp Met Tyr Pro Glu Val Val Arg Ser
              260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
        290                 295                 300

Ile Asp Asn Pro Arg Arg Leu Phe Thr Gly Arg
305                 310                 315

<210> SEQ ID NO 24
<211> LENGTH: 948
<212> TYPE: DNA
<213> ORGANISM: Vulcanisaeta moutnovskia

<400> SEQUENCE: 24

```
atggtgcgta ttagcattgc cggtggtaat gaaattgatc cgggtagcat gggtctgacc    60
ctgtttcatg aacatctgcg tgcaattacc gaagttgttc gttggaattg gcctcatctg   120
tataacgaag atgaagaatt gaaacgtgca attgatgcag ttaacgcagc caaaaaatac   180
ggcgtgaaaa ccattattga tctgaccgtt gcaggtattg gttgtgatgt cgctttaat    240
gaaaaagttg caaaagccac cggtgtgaac attattatgg gcaccggttt ttggacctat   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa agcagcctg    540
gatctgatcc gcattttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatttat ctgccgctgg ataaacgtgt taaaaccgca   720
attgaactga ttaaacgcgg ttggattgat cagctgctgc tgagccatga ttattgtccg   780
accattgatc tgtatccgcc tgaagttgtg cgtagcaccg ttccggattg gaccacgacc   840
ctgatttttg agaaagttat tccgcgtatg cgtagcgaag gtattacgga agaacaaatt   900
aatcgcgtgc tgattgataa tccgcgtcgt ctgtttaccg gtcgttaa                948
```

<210> SEQ ID NO 25
<211> LENGTH: 315
<212> TYPE: PRT
<213> ORGANISM: Vulcanisaeta moutnovskia

<400> SEQUENCE: 25

Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Tyr Thr Glu Ile Pro Phe Tyr Phe Lys Asn Arg Gly Ile

```
                100                 105                 110
Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
            130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
            195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Leu Tyr Pro Pro Glu Val Val Arg Ser
                260                 265                 270

Thr Val Pro Asp Trp Thr Thr Thr Leu Ile Phe Glu Lys Val Ile Pro
            275                 280                 285

Arg Met Arg Ser Glu Gly Ile Thr Glu Glu Gln Ile Asn Arg Val Leu
            290                 295                 300

Ile Asp Asn Pro Arg Arg Leu Phe Thr Gly Arg
305                 310                 315

<210> SEQ ID NO 26
<211> LENGTH: 948
<212> TYPE: DNA
<213> ORGANISM: Vulcanisaeta moutnovskia

<400> SEQUENCE: 26
atggtgcgta ttagcattgc cggtggtaat gaaattgatc cgggtagcat gggtctgacc        60
ctgtttcatg aacatctgcg tctgattacc gaagttgttc gttggaattg cctcatctg       120 tataacgaag atgaagaact gaaacgtgca attgatgcag ttaacgcagc caaaaaatac       180
ggcgtgaaaa ccattattga tctgaccgtt gcaggtattg ttgtgatgt cgctttaat       240 gaaaaagttg caaaagccac cggtgtgaac attattatgg caccggtttt ttatacctat       300
accgaaatcc cgttctattt caaaaaccgt ggtattgata gcctggttga tgcctttgtt       360
catgatatta ccattggtat tcagggcacc aatacccgtg cagcatttgt taaagcagtg       420
attgatagca gcggtctgac caaagatgtt gaaatggcaa ttcgtgcagc agcaaaagca       480
catatcaaaa ccgatgttcc gattatcacc catagctttg ttggtaataa agcagcctg       540 gatctgatcc gcatttttca agaagaaggc gttgatctgg cacgtaccgt tattggtcat       600
gttggtgata ccgatgatat cagctttatt gagcagattc tgcgtgaagg tgcatttatt       660
ggtctggatc gttttggcct ggatatttat ctgccgctgg ataaacgtgt taaaaccgca       720
attgaactga ttaaacgcgg ttggattgat cagctgctgc tgagccatga ttatgctccg       780
accattgata tgtatccgcc tgaagttgtg cgtagcaccg ttccggattg gaccacgacc       840 ctgattttg agaaagttat tccgcgtatg cgtagcgaag gtattacgga agaacaaatt       900
```
aatcgcgtgc tgattgataa tccgcgtcgt ctgtttaccg gtcgttaa            948

<210> SEQ ID NO 27
<211> LENGTH: 315
<212> TYPE: PRT
<213> ORGANISM: Vulcanisaeta moutnovskia

<400> SEQUENCE: 27

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Ala Pro Thr Ile Asp Met Tyr Pro Pro Glu Val Val Arg Ser
            260                 265                 270

Thr Val Pro Asp Trp Thr Thr Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315
```

<210> SEQ ID NO 28
<211> LENGTH: 948
<212> TYPE: DNA
<213> ORGANISM: Vulcanisaeta moutnovskia

<400> SEQUENCE: 28
atggtgcgta ttagcattgc cggtggtaat gaaattgatc cgggtagcat gggtctgacc            60

```
ctgtttcatg aacatctgcg tgcaattacc gaagttgttc gttggaattg gcctcatctg    120
tataacgaag atgaagaatt gaaacgtgca attgatgcag ttaacgcagc caaaaaatac    180
ggcgtgaaaa ccattattga tctgaccgtt gcaggtattg ttgtgatac ccgctttaat     240
gaaaagttg caaagccac cggtgtgaac attattatgg gcaccggttt ttggaccttt      300
accgaaatcc cgttctattt caaaaaccgt ggtattgata gcctggttga tgcctttgtt    360
catgatatta ccattggtat tcagggcacc ccgacccgtg cagcatttgt aaagcagtg     420
attgatagca gcggtctgac caaagatgtt gaaatggcaa ttcgtgcagc agcaaaagca    480
catatcaaaa ccgatgttcc gattatcacc catagctttg ttggtaataa aagcagcctg    540
gatctgatcc gcattttcaa agaagaaggc gttgatctgg cacgtaccgt tattggtcat    600
gttggtgata ccgatgatat cagcttatt gagcagattc tgcgtgaagg tgcatttatt    660
ggtctggatc gttttggcgt ggatatttat ctgccgctgg ataaacgtgt taaaaccgca    720
attgaactga ttaaacgcgg ttggattgat cagctgctgc tgagccatga ttattgtccg    780
accattgatt ggtatccgcc tgaagttgtg cgtagcaccg ttccggattg gaccatgacc    840
ctgatttttg agaaagttat tccgcgtatg cgtagcgaag gtattacgga gaacaaatt    900
aatcgcgtgc tgattgataa tccgcgtcgt ctgtttaccg gtcgttaa                 948
```

<210> SEQ ID NO 29
<211> LENGTH: 315
<212> TYPE: PRT
<213> ORGANISM: Vulcanisaeta moutnovskia

<400> SEQUENCE: 29

Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Thr Arg Phe Asn
65                  70                  75                  80

Glu Lys Val Ala Lys Ala Thr Gly Val Asn Ile Ile Met Gly Thr Gly
                85                  90                  95

Phe Trp Thr Phe Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Pro Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg

```
Phe Gly Val Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 30
<211> LENGTH: 948
<212> TYPE: DNA
<213> ORGANISM: Vulcanisaeta moutnovskia

<400> SEQUENCE: 30
atggtgcgta ttagcattgc cggtggtaat gaaattgatc cgggtagcat gggtctgacc      60
ctgtttcatg aacatctgcg tctgattacc gaagttgttc gttggaattg cccccatctg     120
tataacgaag atgaagaatt gaaacgtgca attgatgcag ttaacgcagc caaaaaatac     180
ggcgtgaaaa ccattattga tctgaccgtt gcaggtattg ttgtgatgt cgctttaat      240 gaaaagttg caaaagccac cggtgtgaac attattatgg gcaccggttt ttatacctt      300 accgaaatcc cgttctattt caaaaaccgt ggtattgata gcctggttga tgcctttgtt     360
catgatttaa ccattggtat tcagggcacc aatacccgtg cagcatttgt taaagcagtg     420
attgatagca gcggtctgac caaagatgtt gaaatggcca ttcgtgcagc agcaaaagca     480
catatcaaaa ccgatgttcc gattatcacc catagctttg ttggtaataa agcagcctg      540 gatctgatcc gcatttttcaa agaagaaggc gttgatctgg cacgtaccgt tattggtcat     600
gttggtgata ccgatgatat cagctttatt gagcagattc tgcgtgaagg tgcatttat      660 ggtctggatc gttttggcct ggatatgtct ctgccgctgg ataaacgtgt taaaaccgca     720
attgaactga ttaaacgcgg ttggattgat cagctgctgc tgagccatga ttattgtccg     780
accattgatc tgtatccgcc tgaagttgtg cgtagcaccg ttccggattg gaccatgacc     840
ctgatttttg agaaagttat tccgcgtatg cgtagcgaag gtattaccga agaacaaatt     900
aatcgcgtgc tgattgataa tccgcgtcgt ctgtttaccg gtcgttaa                  948

<210> SEQ ID NO 31
<211> LENGTH: 315
<212> TYPE: PRT
<213> ORGANISM: Vulcanisaeta moutnovskia

<400> SEQUENCE: 31

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60
```

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Phe Thr Glu Ile Pro Phe Tyr Phe Lys Asn Arg Gly Ile
            100                 105                 110

Asp Ser Leu Val Asp Ala Phe Val His Asp Leu Thr Ile Gly Ile Gln
        115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Met Ser Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Leu Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 32
<211> LENGTH: 948
<212> TYPE: DNA
<213> ORGANISM: Vulcanisaeta moutnovskia

<400> SEQUENCE: 32
atggtgcgta ttagcattgc cggtggtaat gaaattgatc cgggtagcat gggtctgacc      60
ctgtttcatg aacatctgcg tctgattacc gaagttgttc gttggaattg cccccatctg     120
tataacgaag atgaagaatt gaaacgtgca attgatgcag ttaacgcagc caaaaaatac     180
ggcgtgaaaa ccattattga tctgagtgtt gcaggtattg ttgtgatgt cgctttaat      240 gaaaaagttg caaagccac cggtgtgaac attattatgg gcaccggttt ttatacctat     300
accgaaatcc cgttctattt caaaaaccgt ggtattgata gcctggttga tgcctttgtt     360
catgatatta ccattggtat tcagggcacc ccgacccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa agcagcctg     540 gatctgatcc gcatttttcaa agaagaaggc gttgatctgg cacgtaccgt tattggtcat     600
gttggtgata ccgatgatat cagctttatt gagcagattc tgcgtgaagg tgcatttatt     660

```
ggtctggatc gttttggcct ggatatgtct ctgccgctgg ataaacgtgt taaaaccgca      720
attgaactga ttaaacgcgg ttggattgat cagctgctgc tgagccatga ttattgtccg      780
accattgata tgtatccgcc tgaagttgtg cgtagcccgg ttccggattg gaccatgacc      840 ctgattttttg agaaagttat tccgcgtatg cgtagcgaag gtattacgga agaacaaatt      900
aatcgcgtgc tgattgataa tccgcgtcgt ctgtttaccg gtcgttaa                   948
```

<210> SEQ ID NO 33
<211> LENGTH: 315
<212> TYPE: PRT
<213> ORGANISM: Vulcanisaeta moutnovskia

<400> SEQUENCE: 33

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
                20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
        50                  55                  60

Ile Ile Asp Leu Ser Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Pro Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
                180                 185                 190

Leu Ala Arg Thr Val Ile Gly His Val Gly Asp Thr Asp Asp Ile Ser
            195                 200                 205

Phe Ile Glu Gln Ile Leu Arg Glu Gly Ala Phe Ile Gly Leu Asp Arg
        210                 215                 220

Phe Gly Leu Asp Met Ser Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Met Tyr Pro Pro Glu Val Val Arg Ser
                260                 265                 270

Pro Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
        290                 295                 300

Ile Asp Asn Pro Arg Arg Leu Phe Thr Gly Arg
305                 310                 315
```

<210> SEQ ID NO 34
<211> LENGTH: 948
<212> TYPE: DNA
<213> ORGANISM: Vulcanisaeta moutnovskia

<400> SEQUENCE: 34

```
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaatt gaaacgtgca attgatgcag ttaacgcagc caaaaatac      180
ggcgtgaaaa ccattattga tctgagtgtt gcaggtattg gttgtgatac cgctttaat     240
gaaaaagttg caaagccac cggtgtgaac attattatgg gcaccggttt ttggaccttt      300
accgaaatcc cgttctattt caaaaaccgt ggtattgata gcctggttga tgcctttgtt     360
catgatatta ccattggtat tcagggcacc aatacccgtg cagcatttgt aaagcagtg      420
attgatagca gcggtctgac caaagatgtt gaaatggcaa ttcgtgcagc agcaaaagca     480
catatcaaaa ccgatgttcc gattatcacc atagctttg ttggtaataa aagcagcctg      540
gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcct ggatatgtat ctgccgctgg ataaacgtgt taaaaccgca     720
attgaactga ttaaacgcgg ttggattgat cagctgctgc tgagccatga ttattgtccg     780
accattgatc tgtatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                  948
```

<210> SEQ ID NO 35
<211> LENGTH: 315
<212> TYPE: PRT
<213> ORGANISM: Vulcanisaeta moutnovskia

<400> SEQUENCE: 35

```
Met Val Arg Ile Ser Ile Ala Gly Gly Asn Glu Ile Asp Pro Gly Ser
1               5                   10                  15
Met Gly Leu Thr Leu Phe His Glu His Leu Arg Leu Ile Thr Glu Val
                20                  25                  30
Val Arg Trp Asn Trp Pro His Leu Tyr Asn Glu Asp Glu Glu Leu Lys
            35                  40                  45
Arg Ala Ile Asp Ala Val Asn Ala Ala Lys Lys Tyr Gly Val Lys Thr
        50                  55                  60
Ile Ile Asp Leu Ser Val Ala Gly Ile Gly Cys Asp Thr Arg Phe Asn
65                  70                  75                  80
Glu Lys Val Ala Lys Ala Thr Gly Val Asn Ile Ile Met Gly Thr Gly
                85                  90                  95
Phe Trp Thr Phe Thr Glu Ile Pro Phe Tyr Phe Lys Asn Arg Gly Ile
            100                 105                 110
Asp Ser Leu Val Asp Ala Phe Val His Asp Ile Thr Ile Gly Ile Gln
        115                 120                 125
Gly Thr Asn Thr Arg Ala Ala Phe Val Lys Ala Val Ile Asp Ser Ser
    130                 135                 140
Gly Leu Thr Lys Asp Val Glu Met Ala Ile Arg Ala Ala Ala Lys Ala
145                 150                 155                 160
His Ile Lys Thr Asp Val Pro Ile Ile Thr His Ser Phe Val Gly Asn
                165                 170                 175
```

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Ile Ser
        195                 200                 205

Phe Ile Glu Gln Ile Leu Arg Glu Gly Ala Phe Ile Gly Leu Asp Arg
210                 215                 220

Phe Gly Leu Asp Met Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Leu Tyr Pro Pro Glu Val Val Arg Ser
            260                 265                 270

Thr Val Pro Asp Trp Thr Met Thr Leu Ile Phe Glu Lys Val Ile Pro
                275                 280                 285

Arg Met Arg Ser Glu Gly Ile Thr Glu Glu Gln Ile Asn Arg Val Leu
            290                 295                 300

Ile Asp Asn Pro Arg Arg Leu Phe Thr Gly Arg
305                 310                 315

<210> SEQ ID NO 36
<211> LENGTH: 948
<212> TYPE: DNA
<213> ORGANISM: Vulcanisaeta moutnovskia

<400> SEQUENCE: 36
atggtgcgta ttagcattgc cggtgaaaat gaaattgatc cgggtagcat gggtctgacc      60
ctgtttcatg aacatctgcg tctgattacc gaagttgttc gttggaattg cctcatctg     120
tataacgaag atgaagaact gaaacgtgca attgatgcag ttaacgcagc caaaaaatac     180
ggcgtgaaaa ccattattga tctgaccgtt gcaggtattg ttgtgatgt cgctttaat     240
gaaaaagttg caaagccac cggtgtgaac attattatgg caccggttt ttggacctt     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc atagctttg ttggtaataa aagcagcctg     540
gatctgatcc gcatttttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcct ggatatgtat ctgccgctgg ataaacgtgt taaaaccgca     720
attgaactga ttaaacgcgg ttggattgat cagctgctgc tgagccatga ttattgtccg     780
accattgatt ggtatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                 948

<210> SEQ ID NO 37
<211> LENGTH: 315
<212> TYPE: PRT
<213> ORGANISM: Vulcanisaeta moutnovskia

<400> SEQUENCE: 37

Met Val Arg Ile Ser Ile Ala Gly Glu Asn Glu Ile Asp Pro Gly Ser
1               5                   10                  15

```
Met Gly Leu Thr Leu Phe His Glu His Leu Arg Leu Ile Thr Glu Val
             20                  25                  30
Val Arg Trp Asn Trp Pro His Leu Tyr Asn Glu Asp Glu Leu Lys
         35                  40                  45
Arg Ala Ile Asp Ala Val Asn Ala Ala Lys Lys Tyr Gly Val Lys Thr
 50                  55                  60
Ile Ile Asp Leu Thr Val Ala Gly Ile Gly Cys Asp Val Arg Phe Asn
 65                  70                  75                  80
Glu Lys Val Ala Lys Ala Thr Gly Val Asn Ile Met Gly Thr Gly
             85                  90                  95
Phe Trp Thr Phe Thr Glu Ile Pro Phe Tyr Phe Lys Asn Arg Gly Ile
             100                 105                 110
Asp Ser Leu Val Asp Ala Phe Val His Asp Ile Thr Ile Gly Ile Gln
             115                 120                 125
Gly Thr Asn Thr Arg Ala Ala Phe Val Lys Ala Val Ile Asp Ser Ser
             130                 135                 140
Gly Leu Thr Lys Asp Val Glu Met Ala Ile Arg Ala Ala Ala Lys Ala
145                 150                 155                 160
His Ile Lys Thr Asp Val Pro Ile Ile Thr His Ser Phe Val Gly Asn
             165                 170                 175
Lys Ser Ser Leu Asp Leu Ile Arg Ile Phe Lys Glu Glu Gly Val Asp
             180                 185                 190
Leu Ala Arg Thr Val Ile Gly His Val Gly Asp Thr Asp Asp Ile Ser
             195                 200                 205
Phe Ile Glu Gln Ile Leu Arg Glu Gly Ala Phe Ile Gly Leu Asp Arg
 210                 215                 220
Phe Gly Leu Asp Met Tyr Leu Pro Leu Asp Lys Arg Val Lys Thr Ala
225                 230                 235                 240
Ile Glu Leu Ile Lys Arg Gly Trp Ile Asp Gln Leu Leu Leu Ser His
             245                 250                 255
Asp Tyr Cys Pro Thr Ile Asp Trp Tyr Pro Pro Glu Val Val Arg Ser
             260                 265                 270
Thr Val Pro Asp Trp Thr Met Thr Leu Ile Phe Glu Lys Val Ile Pro
             275                 280                 285
Arg Met Arg Ser Glu Gly Ile Thr Glu Glu Gln Ile Asn Arg Val Leu
 290                 295                 300
Ile Asp Asn Pro Arg Arg Leu Phe Thr Gly Arg
305                 310                 315
```

<210> SEQ ID NO 38
<211> LENGTH: 948
<212> TYPE: DNA
<213> ORGANISM: Vulcanisaeta moutnovskia

<400> SEQUENCE: 38

```
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaatt gaaacgtgca attgatgcag ttaacgcagc caaaaaatac     180
ggcgtgaaaa ccattattga tctgaccgtt gcaggtattg ttgtgatgt tcgctttaat     240
gaaaaagttg caaaagccac cggtgtgaac attattatgg caccggtttt ttatacctat     300
accgaaatcc cgttctattt caaaaaccgt ggtattgata gctggttga tgcctttgtt     360
catgatatta ccattggtat tcagggcacc aataccgtg cagcatttgt taaagcagtg     420
```

```
attgatagca gcggtctgac caaagatgtt gaaatggcaa ttcgtgcagc agcaaaagca    480
catatcaaaa ccgatgttcc gattatcacc catagctttg ttggtaataa aagcagcctg    540
gatctgatcc gcattttcaa agaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgatt tttatccgcc tgaagttgtg cgtagcaccg ttccggattg gaccatgacc    840 ctgattttg agaaagttat tccgcgtatg cgtagcgaag gtattaccgga agaacaaatt    900 aatcgcgtgc tgattgataa tccgcgtcgt ctgtttaccg gtcgttaa              948
```

<210> SEQ ID NO 39
<211> LENGTH: 315
<212> TYPE: PRT
<213> ORGANISM: Vulcanisaeta moutnovskia

<400> SEQUENCE: 39

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
                20                  25                  30

Val Arg Trp Asn Trp Pro His Leu Tyr Asn Glu Asp Glu Leu Lys
            35                  40                  45

Arg Ala Ile Asp Ala Val Asn Ala Ala Lys Lys Tyr Gly Val Lys Thr
        50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Phe Tyr Pro Pro Glu Val Val Arg Ser
            260                 265                 270

Thr Val Pro Asp Trp Thr Met Thr Leu Ile Phe Glu Lys Val Ile Pro
        275                 280                 285
```

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 40
<211> LENGTH: 948
<212> TYPE: DNA
<213> ORGANISM: Vulcanisaeta moutnovskia

<400> SEQUENCE: 40

| | | | | | |
|---|---|---|---|---|---|
| atggtgcgta | ttagcattgc | cggtggtaat | gaaattgatc | cgggtagcat | gggtctgacc | 60 |
| ctgtttcatg | aacatctgcg | tctgattacc | gaagttgttc | gttggaattg | gcctcatctg | 120 |
| tataacgaag | atgaagaatt | gaaacgtgca | attgatgcag | ttaacgcagc | caaaaaatac | 180 |
| ggcgtgaaaa | ccattattga | tctgagtgtt | gcaggtattg | gttgtgatgt | tcgctttaat | 240 |
| gaaaaagttg | caaaagccac | cggtgtgaac | attattatgg | gcaccggttt | ttggaccttt | 300 |
| accgaaatcc | cgttctattt | caaaaaccgt | ggtattgata | gcctggttga | tgcctttgtt | 360 |
| catgatatta | ccattggtat | tcagggcacc | ccgacccgtg | cagcatttgt | taaagcagtg | 420 |
| attgatagca | gcggtctgac | caaagatgtt | gaaatggcaa | ttcgtgcagc | agcaaaagca | 480 |
| catatcaaaa | ccgatgttcc | gattataccc | catagctttg | ttggtaataa | aagcagcctg | 540 |
| gatctgatcc | gcatttttcaa | agaagaaggc | gttgatctgg | cacgtaccgt | tattggtcat | 600 |
| gttggtgata | ccgatgatat | cagctttatt | gagcagattc | tgcgtgaagg | tgcatttatt | 660 |
| ggtctggatc | gttttggcct | ggatatgtat | ctgccgctgg | ataaacgtgt | taaaaccgca | 720 |
| attgaactga | ttaaacgcgg | ttggattgat | cagctgctgc | tgagccatga | ttattgtccg | 780 |
| accattgatt | ggtatccgcc | tgaagttgtg | cgtagcaccg | ttccggattg | gaccatgacc | 840 |
| ctgattttttg | agaaagttat | tccgcgtatg | cgtagcgaag | gtattacgga | agaacaaatt | 900 |
| aatcgcgtgc | tgattgataa | tccgcgtcgt | ctgtttaccg | gtcgttaa | | 948 |

<210> SEQ ID NO 41
<211> LENGTH: 315
<212> TYPE: PRT
<213> ORGANISM: Vulcanisaeta moutnovskia

<400> SEQUENCE: 41

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Ser Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Phe Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

```
Gly Thr Pro Thr Arg Ala Ala Phe Val Lys Ala Val Ile Asp Ser Ser
            130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
                180                 185                 190

Leu Ala Arg Thr Val Ile Gly His Val Gly Asp Thr Asp Ile Ser
            195                 200                 205

Phe Ile Glu Gln Ile Leu Arg Glu Gly Ala Phe Ile Gly Leu Asp Arg
210                 215                 220

Phe Gly Leu Asp Met Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Val Arg Ser
                260                 265                 270

Thr Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 42
<211> LENGTH: 948
<212> TYPE: DNA
<213> ORGANISM: Vulcanisaeta moutnovskia

<400> SEQUENCE: 42
atggtgcgta ttagcattgc cggtggtaat gaaattgatc cgggtagcat gggtctgacc      60
ctgtttcatg aacatctgcg tgcaattacc gaagttgttc gttggaattg ccctcatctg     120
tataacgaag atgaagaact gaaacgtgca attgatgcag ttaacgcagc caaaaaatac     180
ggcgtgaaaa ccattattga tctgaccgtt gcaggtattg gttgtgatgt cgctttaat      240
gaaaaagttg caaagccac cggtgtgaac attattatgg gcaccggttt ttatacctat     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa agcagcctg      540
gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcgt ggatatttat ctgccgctgg ataaacgtgt taaaaccgca     720
attgaactga ttaaacgcgg ttggattgat cagctgctgc tgagccatga ttattgtccg     780
accattgatc tgtatccgcc tgaagttgtg cgtagcaccg ttccggattg gaccatgacc     840
ctaattttgt agaaagttat ccgcgtatgc gtagcgaag gtattacgga agaacaaatt     900
aatcgcgtgc tgattgataa tccgcgtcgt ctgtttaccg gtcgttaa                  948

<210> SEQ ID NO 43
<211> LENGTH: 315
```

<212> TYPE: PRT
<213> ORGANISM: Vulcanisaeta moutnovskia

<400> SEQUENCE: 43

Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Val Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Leu Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 44
<211> LENGTH: 948
<212> TYPE: DNA
<213> ORGANISM: Vulcanisaeta moutnovskia

<400> SEQUENCE: 44
atggtgcgta ttagcattgc cggtggtaat gaaattgatc cgggtagcat gggtctgacc    60
ctgtttcatg aacatctgcg tctgattacc gaagttgttc gttggaattg gcctcatctg   120
tataacgaag atgaagaatt gaaacgtgca attgatgcag ttaacgcagc caaaaaatac   180

```
ggcgtgaaaa ccattattga tgtgagtgtt gcaggtattg gttgtgatgt tcgctttaat   240
gaaaaagttg caaaagccac cggtgtgaac attattatgg gcaccggttt ttggaccttt   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gagatggcaa ttcgtgcagc agcaaaagca   480
catatcaaaa ccgatgttcc gattatcacc catagctttg ttggtaataa aagcagcctg   540
gatctgatcc gcattttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatgtat ctgccgctgg ataaacgtgt taaaaccgca   720
attgaactga ttaaacgcgg ttggattgat cagctgctgc tgagccatga ttatgctccg   780
accattgatc tgtatccgcc tgaagttgtg cgtagcaccg ttccggattg gaccacgacc   840 ctgattttg agaaagttat tccgcgtatg cgtagcgaag gtattacgga agaacaaatt   900
aatcgcgtgc tgattgataa tccgcgtcgt ctgtttaccg gtcgttaa                948
```

<210> SEQ ID NO 45
<211> LENGTH: 315
<212> TYPE: PRT
<213> ORGANISM: Vulcanisaeta moutnovskia

<400> SEQUENCE: 45

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
                20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
        50                  55                  60

Ile Ile Asp Val Ser Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Phe Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Met Tyr Leu Pro Leu Asp Lys Arg Val Lys Thr Ala
225                 230                 235                 240
```

-continued

```
Ile Glu Leu Ile Lys Arg Gly Trp Ile Asp Gln Leu Leu Leu Ser His
                245                 250                 255

Asp Tyr Ala Pro Thr Ile Asp Leu Tyr Pro Pro Glu Val Val Arg Ser
            260                 265                 270

Thr Val Pro Asp Trp Thr Thr Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315
```

<210> SEQ ID NO 46
<211> LENGTH: 948
<212> TYPE: DNA
<213> ORGANISM: Vulcanisaeta moutnovskia

<400> SEQUENCE: 46

```
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaact gaaacgtgca attgatgcag ttaacgcagc caaaaaatac     180
ggcgtgaaaa ccattattga tctgagtgtt gcaggtattg gttgtgatgt tcgctttaat     240
gaaaaagttg caaaagccac cggtgtgaac attattatgg gcaccggttt ttggaccttt     300
accgaaatcc cgttctattt caaaaaccgt ggtattgata gcctggttga tgcctttgtt     360
catgatatta ccattggtat tcagggcacc ccgacccgtg cagcatttgt taaagcagtg     420
attgatagca gcggtctgac caaagatgtt gaaatggcaa ttcgtgcagc agcaaaagca     480
catatcaaaa ccaatgttcc gattataacc catagctttg ttggtaataa agcagcctg     540
gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcgt ggatatttat ctgccgctgg ataaacgtgt taaaaccgca     720
attgaactga ttaaacgcgg ttggattgat cagctgctgc tgagccatga ttattgtccg     780
accattgata tgtatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                  948
```

<210> SEQ ID NO 47
<211> LENGTH: 315
<212> TYPE: PRT
<213> ORGANISM: Vulcanisaeta moutnovskia

<400> SEQUENCE: 47

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Ser Val Ala Gly Ile Gly Cys Asp Val Arg Phe Asn
65                  70                  75                  80

Glu Lys Val Ala Lys Ala Thr Gly Val Asn Ile Ile Met Gly Thr Gly
```

85                  90                  95
Phe Trp Thr Phe Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Pro Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala
145                 150                 155                 160

His Ile Lys Thr Asn Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Val Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Met Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
        290                 295                 300

Ile Asp Asn Pro Arg Arg Leu Phe Thr Gly Arg
305                 310                 315

<210> SEQ ID NO 48
<211> LENGTH: 948
<212> TYPE: DNA
<213> ORGANISM: Vulcanisaeta moutnovskia

<400> SEQUENCE: 48
atggtgcgta ttagcattgc cggtggtaat gaaattgatc cgggtagcat gggtctgacc      60
ctgtttcatg aacatctgcg tctgattacc gaagttgttc gttggaattg ccccatctg     120 tataacgaag atgaagaatt gaaacgtgca attgatgcag ttaacgcagc caaaaaatac    180
ggcgtgaaaa ccattattga tctgagtgtt gcaggtattg ttgtgatgt tcgctttaat     240 gaaaaagttg caaagccac cggtgtgaac attattatgg caccggttt ttggaccttt     300 accgaaatcc cgttctattt caaaaaccgt ggtattgata gcctggttga tgcctttgtt    360
catgatatta ccattggtat tcagggcacc ccgacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa agcagcctg    540 gatctgatcc gcattttcaa agaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgatt ggtatccgcc tgaagttgtg cgtagcaccg ttccggattg gaccatgacc    840

```
ctgatttttg agaaagttat tccgcgtatg cgtagcgaag gtattacgga agaacaaatt    900
aatcgcgtgc tgattgataa tccgcgtcgt ctgtttaccg gtcgttaa              948
```

<210> SEQ ID NO 49
<211> LENGTH: 315
<212> TYPE: PRT
<213> ORGANISM: Vulcanisaeta moutnovskia

<400> SEQUENCE: 49

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Ser Val Ala Gly Ile Gly Cys Asp Val Arg Phe Asn
65                  70                  75                  80

Glu Lys Val Ala Lys Ala Thr Gly Val Asn Ile Met Gly Thr Gly
                85                  90                  95

Phe Trp Thr Phe Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Pro Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315
```

<210> SEQ ID NO 50
<211> LENGTH: 948
<212> TYPE: DNA
<213> ORGANISM: Vulcanisaeta moutnovskia

```
<400> SEQUENCE: 50
atggtgcgta ttagcattgc cggtggtaat gaaattgatc cgggtagcat gggtctgacc      60
ctgtttcatg aacatctgcg tgcaattacc gaagttgttc gttggaattg gcctcatctg     120
tataacgaag atgaagaatt gaaacgtgca attgatgcag ttaacgcagc caaaaaatac     180
ggcgtgaaaa ccattattga tctgaccgtt gcaggtattg gttgtgatgt tcgctttaat     240
gaaaaagttg caaagccac cggtgtgaac attattatgg gcaccggttt ttggaccttt      300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattatcacc catagctttg ttggtaataa agcagcctg     540 gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcgt ggatatttat ctgccgctgg ataaacgtgt taaaaccgca     720
attgaactga ttaaacgcgg ttggattgat cagctgctgc tgagccatga ttattgtccg     780
accattgatt ggtatccgcc tgaagttgtg cgtagcaccg ttccggattg gaccatgacc     840 ctgattttg agaaagttat tccgcgtatg cgtagcgaag gtattacgga gaacaaatt     900 aatcgcgtgc tgattgataa tccgcgtcgt ctgtttaccg gtcgttaa                 948

<210> SEQ ID NO 51
<211> LENGTH: 315
<212> TYPE: PRT
<213> ORGANISM: Vulcanisaeta moutnovskia

<400> SEQUENCE: 51

Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Phe Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
```

```
                195                 200                 205
Phe Ile Glu Gln Ile Leu Arg Glu Gly Ala Phe Ile Gly Leu Asp Arg
    210                 215                 220

Phe Gly Val Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Glu Val Val Arg Ser
                260                 265                 270

Thr Val Pro Asp Trp Thr Met Thr Leu Ile Phe Glu Lys Val Ile Pro
                275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 52
<211> LENGTH: 948
<212> TYPE: DNA
<213> ORGANISM: Vulcanisaeta moutnovskia

<400> SEQUENCE: 52
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaatt gaaacgtgca attgatgcag ttaacgcagc caaaaaatac     180
ggcgtgaaaa ccattattga tctgagtgtt gcaggtattg gttgtgatgt tcgctttaat     240
gaaaaagttg caaaagccac cggtgtgaac attattatgg gcaccggttt ttggaccttt     300
accgaaatcc cgttctattt caaaaaccgt ggtattgata gcctggttga tgcctttgtt     360
catgatatta ccattggtat tcagggcacc ccgacccgtg cagcatttgt taaagcagtg     420
attgatagca gcggtctgac caaagatgtt gaaatggcaa ttcgtgcagc agcaaaagca     480
catatcaaaa ccgatgttcc gattataacc catagctttg ttggtaataa aagcagcctg     540
gatctgatcc gcatttttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcct ggatatgtat ctgccgctgg ataaacgtgt taaaaccgca     720
attgaactga ttaaacgcgg ttggattgat cagctgctgc tgagccatga ttattgtccg     780
accattgatt ggtatccgcc tgaagttgtg cgtagcaccg ttccggattg gaccatgacc     840
ctgattttg agaaagttat tccgcgtatg cgtagcgaag gtattacgga agaacaaatt     900
aatcgcgtgc tgattgataa tccgcgtcgt ctgtttaccg gtcgttaa                   948

<210> SEQ ID NO 53
<211> LENGTH: 315
<212> TYPE: PRT
<213> ORGANISM: Vulcanisaeta moutnovskia

<400> SEQUENCE: 53

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45
```

-continued

```
Arg Ala Ile Asp Ala Val Asn Ala Ala Lys Lys Tyr Gly Val Lys Thr
 50                  55                  60

Ile Ile Asp Leu Ser Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Trp Thr Phe Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Pro Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Met Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 54
<211> LENGTH: 948
<212> TYPE: DNA
<213> ORGANISM: Vulcanisaeta moutnovskia

<400> SEQUENCE: 54
atggtgcgta ttagcattgc cggtggtaat gaaattgatc cgggtagcat gggtctgacc    60
ctgtttcatg aacatctgcg tgcaattacc gaagttgttc gttggaattg gcctcatctg   120
tataacgaag atgaagaatt gaaacgtgca attgatgcag ttaacgcagc caaaaaatac   180
ggcgtgaaaa ccattattga tctgagtgtt gcaggtattg gttgtgatgt tcgctttaat   240
gaaaaagttg caaaagccac cggtgtgaac attattatgg gcaccggttt ttggacctat   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa agcagcctg    540 gatctgatcc gcatttttcaa agaagaaggc gttgatctgg cacgtaccgt tattggtcat   600
```

```
gttggtgata ccgatgatat cagctttatt gagcagattc tgcgtgaagg tgcatttatt    660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgatc tgtatccgcc tgaagttgtg cgtagcaccg ttccggattg gaccatgacc    840
ctgatttttg agaaagttat tccgcgtatg cgtagcgaag gtattacgga agaacaaatt    900
aatcgcgtgc tgattgataa tccgcgtcgt ctgtttaccg gtcgttaa                 948
```

<210> SEQ ID NO 55
<211> LENGTH: 315
<212> TYPE: PRT
<213> ORGANISM: Vulcanisaeta moutnovskia

<400> SEQUENCE: 55

```
Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Ser Val Ala Gly Ile Gly Cys Asp Val Arg Phe Asn
65                  70                  75                  80

Glu Lys Val Ala Lys Ala Thr Gly Val Asn Ile Met Gly Thr Gly
            85                  90                  95

Phe Trp Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
            165                 170                 175

Lys Ser Ser Leu Asp Leu Ile Arg Ile Phe Lys Glu Glu Gly Val Asp
        180                 185                 190

Leu Ala Arg Thr Val Ile Gly His Val Gly Asp Thr Asp Asp Ile Ser
    195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
            245                 250                 255

Asp Tyr Cys Pro Thr Ile Asp Leu Tyr Pro Pro Glu Val Val Arg Ser
        260                 265                 270

Thr Val Pro Asp Trp Thr Met Thr Leu Ile Phe Glu Lys Val Ile Pro
    275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
```

<210> SEQ ID NO 56
<211> LENGTH: 948
<212> TYPE: DNA
<213> ORGANISM: Vulcanisaeta moutnovskia

<400> SEQUENCE: 56

```
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaatt gaaacgtgca atagatgcag ttaacgcagc caaaaaatac     180
ggcgtgaaaa ccattattga tctgaccgtt gcaggtattg gttgtgatgt tcgctttaat     240
gaaaaagttg caaaagccac cggtgtgaac attattatgg gcaccggttt ttatacctat     300
accgaaatcc cgttctattt caaaaaccgt ggtattgata gcctggttga tgcctttgtt     360
catgatatta ccattggtat tcagggcacc aatacccgtg cagcatttgt taaagcagtg     420
attgatagca gcggtctgac caaagatgtt gaaatggcaa ttcgtgcagc agcaaaagca     480
catatcaaaa ccgatgttcc gattataccc catagctttg ttggtaataa aagcagcctg     540
gatctgatcc gcattttcaa agaagaaggc gttgatctgg cacgtaccgt tattggtcat     600
gttggtgata ccgatgatat cagctttatt gagcagattc tgcgtgaagg tgcatttatt     660
ggtctggatc gttttggcct ggatatttat ctgccgctgg ataaacgtgt taaaaccgca     720
attgaactga ttaaacgcgg ttggattgat cagctgctgc tgagccatga ttattgtccg     780
accattgatt gttatccgcc tgaagttgtg cgtagcaccg ttccggattg gaccatgacc     840
atgatttttg agaaagttat tccgcgtatg cgtagcgaag gtattacgga agaacaaatt     900
aatcgcgtgc tgattgataa tccgcgtcgt ctgtttaccg gtcgttaa                  948
```

<210> SEQ ID NO 57
<211> LENGTH: 315
<212> TYPE: PRT
<213> ORGANISM: Vulcanisaeta moutnovskia

<400> SEQUENCE: 57

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160
```

-continued

```
His Ile Lys Thr Asp Val Pro Ile Ile Thr His Ser Phe Val Gly Asn
            165                 170                 175
Lys Ser Ser Leu Asp Leu Ile Arg Ile Phe Lys Glu Glu Gly Val Asp
        180                 185                 190
Leu Ala Arg Thr Val Ile Gly His Val Gly Asp Thr Asp Asp Ile Ser
    195                 200                 205
Phe Ile Glu Gln Ile Leu Arg Glu Gly Ala Phe Ile Gly Leu Asp Arg
210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Leu Ser His
                245                 250                 255
Asp Tyr Cys Pro Thr Ile Asp Cys Tyr Pro Pro Glu Val Val Arg Ser
            260                 265                 270
Thr Val Pro Asp Trp Thr Met Thr Met Ile Phe Glu Lys Val Ile Pro
        275                 280                 285
Arg Met Arg Ser Glu Gly Ile Thr Glu Glu Gln Ile Asn Arg Val Leu
    290                 295                 300
Ile Asp Asn Pro Arg Arg Leu Phe Thr Gly Arg
305                 310                 315
```

<210> SEQ ID NO 58
<211> LENGTH: 948
<212> TYPE: DNA
<213> ORGANISM: Vulcanisaeta moutnovskia

<400> SEQUENCE: 58

```
atggtgcgta ttagcattgc cggtggtaat gaaattgatc cgggtagcat gggtctgacc    60
ctgtttcatg aacatctgcg tctgattacc gaagttgttc gttggaattg gcctcatctg   120
tataacgaag atgaagaatt gaaacgtgca attgatgcag ttaacgcagc caaaaaatac   180
ggcgtgaaaa ccattattga tctgaccgtt gcaggtattg gttgtgatgt tcgctttaat   240
gaaaaagttg caaaagccac cggtgtgaac attattatgg caccggtttt ttatacctat   300
accgaaatcc cgttctattt caaaaaccgt ggtattgata gcctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa agcagcctg    540
gatctgatcc gcattttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatttat ctgccgctgg ataaacgtgt taaaaccgca   720
attgaactga ttaaacgcgg ttggattgat cagctgctgc tgagccatga ttattgtccg   780
accattgatt gctatccgcc tgaagttgtg cgtagcacca ccccggattg gaccatgacc   840
ctgattttg agaaagttat tccgcgtatg cgtagcgaag gtattacgga agaacaaatt   900
aatcgcgtgc tgattgataa tccgcgtcgt ctgtttaccg gtcgttaa              948
```

<210> SEQ ID NO 59
<211> LENGTH: 315
<212> TYPE: PRT
<213> ORGANISM: Vulcanisaeta moutnovskia

<400> SEQUENCE: 59

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
                35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Val Arg Ser
            260                 265                 270

Thr Thr Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 60
<211> LENGTH: 948
<212> TYPE: DNA
<213> ORGANISM: Vulcanisaeta moutnovskia

<400> SEQUENCE: 60
atggtgcgta ttagcattgc cggtggtaat gaaattgatc cgggtagcat gggtctgacc      60
ctgtttcatg aacatctgcg tctgattacc gaagttgttc gttggaattg gcctcatctg     120
tataacgaag atgaagaatt gaaacgtgca attgatgcag ttaacgcagc caaaaaatac     180
ggcgtgaaaa ccattattga tctgaccgtt gcaggtattg gttgtgatgt tcgctttaat     240
gaaaaagttg caaaagccac cggtgtgaac attattatgg caccggtttt ttatacctat     300
accgaaatcc cgttctattt caaaaaccgt ggtattgata gcctggttga tgcctttgtt     360
```

```
catgatatta ccattggtat tcagggcacc aatacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa agcagcctg     540 gatctgatcc gcattttcaa agaagaaggc gttgatctgg cacgtaccgt tattggtcat    600
gttggtgata ccgatgatat cagctttatt gagcagattc tgcgtgaagg tgcatttatt    660
ggtctggatc gttttggcct ggatatttat ctgccgctgg ataaacgtgt taaaaccgct    720
attgaactga ttaaacgcgg ttggattgat cagctgctgc tgagccatga ttattgtccg    780
accattgatt ggtatccgcc tgaagttgtg cgtagcccgg ttccggattg gaccatgacc    840 ctgattttg agaaagttat tccgcgtatg cgtagcgaag tattacggga agaacaaatt     900
aatcgcgtgc tgattgataa tccgcgtcgt ctgtttaccg gtcgttaa                 948
```

<210> SEQ ID NO 61
<211> LENGTH: 315
<212> TYPE: PRT
<213> ORGANISM: Vulcanisaeta moutnovskia

<400> SEQUENCE: 61

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Val Arg Ser
            260                 265                 270
```

Pro Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 62
<211> LENGTH: 948
<212> TYPE: DNA
<213> ORGANISM: Vulcanisaeta moutnovskia

<400> SEQUENCE: 62
atggtgcgta ttagcattgc cggtggtaat gaaattgatc cgggtagcat gggtctgacc    60
ctgtttcatg aacatctgcg tctgattacc gaagttgttc gttggaattg gcctcatctg   120
tataacgaag atgaagaatt gaaacgtgca attgatgcag ttaacgcagc caaaaaatac   180
ggcgtgaaaa ccattattga tctgaccgtt gcaggtattg gttgtgatgt tcgctttaat   240
gaaaaagttg caaaagccac cggtgtgaac attattatgg gcaccggttt ttatacctat   300
accgaaatcc cgttctattt caaaaaccgt ggtattgata gcctggttga tgcctttatt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc atagctttg ttggtaataa agcagcctg    540
gatctgatcc gcattttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatttat ccgccgctgg ataaacgtgt taaaaccgca   720
attgaactga ttaaacgcgg ttggattgat cagctgctgc tgagccatga ttattgtccg   780
accattgatt ggtatccgcc tgaagttgtg cgtagcaccg ttccggattg gaccatgacc   840
ctgattttg agaaagttat tccgcgtatg cgtagcgaag gtattagcga gaacaaatt    900
aatcgcgtgc tgattgataa tccgcgtcgt ctgtttaccg gtcgttaa              948

<210> SEQ ID NO 63
<211> LENGTH: 315
<212> TYPE: PRT
<213> ORGANISM: Vulcanisaeta moutnovskia

<400> SEQUENCE: 63

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Ile His Asp Ile Thr Ile Gly Ile Gln
            115                 120                 125

Gly Thr Asn Thr Arg Ala Ala Phe Val Lys Ala Val Ile Asp Ser Ser
        130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Pro Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Ser Glu Glu Gln Ile Asn Arg Val Leu
    290                 295                 300

Ile Asp Asn Pro Arg Arg Leu Phe Thr Gly Arg
305                 310                 315

<210> SEQ ID NO 64
<211> LENGTH: 948
<212> TYPE: DNA
<213> ORGANISM: Vulcanisaeta moutnovskia

<400> SEQUENCE: 64

```
atggtgcgta ttagcattgc cggtggtaat gaaattgatc cgggtagcat gggtctgacc    60
ctgtttcatg aacatctgcg tctgattacc gaagttgttc gttggaattg gcctcatctg   120
tataacgaag atgaagaatt gaaacgtgca attgatgcag ttaacgcagc caaaaaatac   180
ggcgtgaaaa ccattattga tctgaccgtt gcaggtattg ttgtgatgt tcgctttaat   240
gaaaaagttg caaagccac cggtgtgaac attattatgg caccggtttt ttatacctat   300
accgaaatcc cgttctattt caaaaaccgt ggtattgata gcctggttga tgcctttatt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa agcagcctg   540
gatctgatcc gcattttcaa agaagaaggc gttgatctgg cacgtaccgt tattggtcat   600
gttggtgata cagatgatat cagctttatt gagcagattc tgcgtgaagg tgcatttatt   660
ggtctagatc gttttggcct ggatatttat ctgccgctgg ataaacgtgt taaaaccgca   720
attgaactga ttaaacgcgg ttggattgat cagctgctgc tgagccatga ttattgtccg   780
accattgatt ggtatccgcc tgaagttgtg cgtagcaccg ttcctgattg gaccatgacc   840
ctgattttg agaagttat tccgcgtatg cgtagcgaag gtattacgga agaacaaatt   900
aatcgcgtgc tgattgataa tccgcgtcgt ctgtttaccg gtcgttaa             948
```

<210> SEQ ID NO 65
<211> LENGTH: 315
<212> TYPE: PRT
<213> ORGANISM: Vulcanisaeta moutnovskia

<400> SEQUENCE: 65

```
Met Val Arg Ile Ser Ile Ala Gly Gly Asn Glu Ile Asp Pro Gly Ser
1               5                   10                  15
Met Gly Leu Thr Leu Phe His Glu His Leu Arg Leu Ile Thr Glu Val
            20                  25                  30
Val Arg Trp Asn Trp Pro His Leu Tyr Asn Glu Asp Glu Glu Leu Lys
        35                  40                  45
Arg Ala Ile Asp Ala Val Asn Ala Ala Lys Lys Tyr Gly Val Lys Thr
    50                  55                  60
Ile Ile Asp Leu Thr Val Ala Gly Ile Gly Cys Asp Val Arg Phe Asn
65                  70                  75                  80
Glu Lys Val Ala Lys Ala Thr Gly Val Asn Ile Ile Met Gly Thr Gly
                85                  90                  95
Phe Tyr Thr Tyr Thr Glu Ile Pro Phe Tyr Phe Lys Asn Arg Gly Ile
            100                 105                 110
Asp Ser Leu Val Asp Ala Phe Ile His Asp Ile Thr Ile Gly Ile Gln
        115                 120                 125
Gly Thr Asn Thr Arg Ala Ala Phe Val Lys Ala Val Ile Asp Ser Ser
    130                 135                 140
Gly Leu Thr Lys Asp Val Glu Met Ala Ile Arg Ala Ala Ala Lys Ala
145                 150                 155                 160
His Ile Lys Thr Asp Val Pro Ile Ile Thr His Ser Phe Val Gly Asn
                165                 170                 175
Lys Ser Ser Leu Asp Leu Ile Arg Ile Phe Lys Glu Glu Gly Val Asp
            180                 185                 190
Leu Ala Arg Thr Val Ile Gly His Val Gly Asp Thr Asp Asp Ile Ser
        195                 200                 205
Phe Ile Glu Gln Ile Leu Arg Glu Gly Ala Phe Ile Gly Leu Asp Arg
    210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Leu Ser His
                245                 250                 255
Asp Tyr Cys Pro Thr Ile Asp Trp Tyr Pro Pro Glu Val Val Arg Ser
            260                 265                 270
Thr Val Pro Asp Trp Thr Met Thr Leu Ile Phe Glu Lys Val Ile Pro
        275                 280                 285
Arg Met Arg Ser Glu Gly Ile Thr Glu Glu Gln Ile Asn Arg Val Leu
    290                 295                 300
Ile Asp Asn Pro Arg Arg Leu Phe Thr Gly Arg
305                 310                 315
```

<210> SEQ ID NO 66
<211> LENGTH: 948
<212> TYPE: DNA
<213> ORGANISM: Vulcanisaeta moutnovskia

<400> SEQUENCE: 66
atggtgcgta ttagcattgc cggtggtaat gaaattgatc cgggtagcat gggtctgacc    60
ctgtttcatg aacatctgcg tctgattacc gaagttgttc gttggaattg gcctcatctg   120

-continued

```
tataacgaag atgaagaatt gaaacgtgca attgatgcag ttaacgcagc caaaaaatac    180
ggcgtgaaaa ccattattga tctgaccgtt gcaggtattg ttgtgatgt tcgctttaat     240 gaaaaagttg caaagccac cggtgtgaac attattatgg gcaccggttt ttggacctat     300
accgaaatcc cgttctattt caaaaaccgt ggtattgata gcctggttga tgcctttgtt    360
catgatatta ccattggtat tcagggcacc aatacccgtg cagcatttgt taaagcagtg    420
attgatagca gcggtctgac caaagatgtt gaaatggcaa ttcgtgcagc agcaaaagca    480
catatcaaaa ccgatgttcc gattatcacc catagctttg ttggtaataa agcagcctg    540 gatctgatcc gcattttcaa agaagaaggc gttgatctgg cacgtaccgt tattggtcat    600
gttggtgata ccgatgatat cagcttatt gagcagattc tgcgtgaagg tgcatttatt     660
ggtctggatc gttttggcct ggatatttat ctgccgctgg ataaacgtgt taaaaccgca    720
attgaactga ttaaacgcgg ttggattgat cagctgctgc tgagccatga ttattgtccg    780
accattgatt ggtatccgcc tgaagttgtg cgtagcaccg ttccggattg gaccatgacc    840
ctgatttttg agaaagttat tccgcgtatg cgtagcgaag gtattacgga agaacaaatt    900
aatcgcgtgc tgattgataa tccgcgtcgt ctgtttaccg gtcgttaa                948
```

<210> SEQ ID NO 67
<211> LENGTH: 315
<212> TYPE: PRT
<213> ORGANISM: Vulcanisaeta moutnovskia

<400> SEQUENCE: 67

```
Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Trp Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220
```

```
Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
            245                 250                 255

Asp Tyr Cys Pro Thr Ile Asp Trp Tyr Pro Pro Glu Val Val Arg Ser
        260                 265                 270

Thr Val Pro Asp Trp Thr Met Thr Leu Ile Phe Glu Lys Val Ile Pro
    275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 68
<211> LENGTH: 948
<212> TYPE: DNA
<213> ORGANISM: Vulcanisaeta moutnovskia

<400> SEQUENCE: 68
atggtgcgta ttagcattgc cggtggtaat gaaattgatc cgggtagcat gggtctgacc    60
ctgtttcatg aacatctgcg tgcaattacc gaagttgttc gttggaattg gcctcatctg   120
tataacgaag atgaagaatt gaaacgtgca attgatgcag ttaacgcagc caaaaaatac   180
ggcgtgaaaa ccattattga tctgaccgtt gcaggtattg gttgtgatgt cgctttaat   240
gaaaaagttg caaaagccac cggtgtgaac attattatgg caccggtttt ttataccttt   300
accgaaatcc cgttctattt caaaaaccgt ggtattgata gctggttga tgcctttgtt   360
catgatatta ccattggtat tcagggcacc aatacccgtg cagcatttgt taaagcagtg   420
attgatagca gcggtctgac caaagatgtt gaaatggcaa ttcgtgcagc agcaaaagca   480
catatcaaaa ccgatgttcc gattatcacc catagctttg ttggtaataa agcagcctg   540
gatctgatcc gcatttttcaa agaagaaggc gttgatctgg cacgtaccgt tattggtcat   600
gttggtgata ccgatgatat cagctttatt gagcagattc tgcgtgaagg tgcatttatt   660
ggtctggatc gttttggcct ggatatttat ctgccgctgg ataaacgtgt taaaaccgca   720
attgaactga ttaaacgcgg ttggattgat cagctgctgc tgagccatga ttattgtccg   780
accattgatc tgtatccgcc tgaagttgtg cgtagcaccg ttccggattg gaccatgacc   840
ctgattttg agaaagttat tccgcgtatg cgtagcgaag gtattacgga gaacaaatt   900
aatcgcgtgc tgattgataa tccgcgtcgt ctgtttaccg gtcgttaa              948

<210> SEQ ID NO 69
<211> LENGTH: 315
<212> TYPE: PRT
<213> ORGANISM: Vulcanisaeta moutnovskia

<400> SEQUENCE: 69

Met Val Arg Ile Ser Ile Ala Gly Gly Asn Glu Ile Asp Pro Gly Ser
1               5                   10                  15

Met Gly Leu Thr Leu Phe His Glu His Leu Arg Ala Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
```

```
              65                  70                  75                  80
     Glu Lys Val Ala Lys Ala Thr Gly Val Asn Ile Ile Met Gly Thr Gly
                     85                  90                  95

Phe Tyr Thr Phe Thr Glu Ile Pro Phe Tyr Phe Lys Asn Arg Gly Ile
                     100                 105                 110

Asp Ser Leu Val Asp Ala Phe Val His Asp Ile Thr Ile Gly Ile Gln
                     115                 120                 125

Gly Thr Asn Thr Arg Ala Ala Phe Val Lys Ala Val Ile Asp Ser Ser
             130                 135                 140

Gly Leu Thr Lys Asp Val Glu Met Ala Ile Arg Ala Ala Ala Lys Ala
     145                 150                 155                 160

His Ile Lys Thr Asp Val Pro Ile Ile Thr His Ser Phe Val Gly Asn
                     165                 170                 175

Lys Ser Ser Leu Asp Leu Ile Arg Ile Phe Lys Glu Glu Gly Val Asp
                     180                 185                 190

Leu Ala Arg Thr Val Ile Gly His Val Gly Asp Thr Asp Asp Ile Ser
                     195                 200                 205

Phe Ile Glu Gln Ile Leu Arg Glu Gly Ala Phe Ile Gly Leu Asp Arg
             210                 215                 220

Phe Gly Leu Asp Ile Tyr Leu Pro Leu Asp Lys Arg Val Lys Thr Ala
     225                 230                 235                 240

Ile Glu Leu Ile Lys Arg Gly Trp Ile Asp Gln Leu Leu Ser His
                     245                 250                 255

Asp Tyr Cys Pro Thr Ile Asp Leu Tyr Pro Pro Glu Val Val Arg Ser
                     260                 265                 270

Thr Val Pro Asp Trp Thr Met Thr Leu Ile Phe Glu Lys Val Ile Pro
                     275                 280                 285

Arg Met Arg Ser Glu Gly Ile Thr Glu Glu Gln Ile Asn Arg Val Leu
             290                 295                 300

Ile Asp Asn Pro Arg Arg Leu Phe Thr Gly Arg
     305                 310                 315

<210> SEQ ID NO 70
<211> LENGTH: 951
<212> TYPE: DNA
<213> ORGANISM: Vulcanisaeta moutnovskia

<400> SEQUENCE: 70
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg ttttatacc     300 tataccgaaa tcccgttcta tttcaaaaac cgtggtattg atagcctggt tgatgccttt     360
gttcatgata ttaccattgg tattcagggc accaatacc gtgcagcatt tgttaaagca     420
gtgattgata gcagcggtct gaccaaagat gttgaaatgg caattcgtgc agcagcaaaa     480
gcacatatca aaaccgatgt tccgattatc ccatagct tgttggtaa taaaagcagc      540 ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
```

```
gcaattgaac tgattaaacg cggttggatt gatcagctgc tgctgagcca tgattattgt    780
ccgaccattg atttttatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a            951
```

```
<210> SEQ ID NO 71
<211> LENGTH: 316
<212> TYPE: PRT
<213> ORGANISM: Vulcanisaeta moutnovskia

<400> SEQUENCE: 71

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Phe Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 72
<211> LENGTH: 951
```

```
<212> TYPE: DNA
<213> ORGANISM: Vulcanisaeta moutnovskia

<400> SEQUENCE: 72
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc accggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaccgatgt tccgattatc acccatagct tgttggtaa taaaagcagc       540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg atatgtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a              951

<210> SEQ ID NO 73
<211> LENGTH: 316
<212> TYPE: PRT
<213> ORGANISM: Vulcanisaeta moutnovskia

<400> SEQUENCE: 73

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
                100                 105                 110

Ile Asp Ser Leu Val Asp Ala Phe Val His Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
```

```
              180                 185                 190
Asp Leu Ala Arg Thr Val Ile Gly His Val Gly Asp Thr Asp Ile
            195                 200                 205

Ser Phe Ile Glu Gln Ile Leu Arg Glu Gly Ala Phe Ile Gly Leu Asp
210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
            245                 250                 255

His Asp Tyr Cys Pro Thr Ile Asp Met Tyr Pro Pro Glu Val Val Arg
            260                 265                 270

Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
            290                 295                 300

Leu Ile Asp Asn Pro Arg Arg Leu Phe Thr Gly Arg
305                 310                 315

<210> SEQ ID NO 74
<211> LENGTH: 951
<212> TYPE: DNA
<213> ORGANISM: Vulcanisaeta moutnovskia

<400> SEQUENCE: 74
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg atctgtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a            951

<210> SEQ ID NO 75
<211> LENGTH: 316
<212> TYPE: PRT
<213> ORGANISM: Vulcanisaeta moutnovskia

<400> SEQUENCE: 75

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30
```

```
Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 76
<211> LENGTH: 951
<212> TYPE: DNA
<213> ORGANISM: Vulcanisaeta moutnovskia

<400> SEQUENCE: 76
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaaccattat tgatctgacc gttgcaggta ttggttgtga tgttcgcttt     240
aatgaaaaag ttgcaaaagc caccggtgtg aacattatta tgggcaccgg ttttataccc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
```

```
gcacatatca aaaccgatgt tccgattatc acccatagct tgttggtaa taaaagcagc    540 ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatt tatctgccgc tggataaacg tgttaaaacc    720
gcaattgaac tgattaaacg cggttggatt gatcagctgc tgctgagcca tgattattgt    780
ccgaccattg atgcgtatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951
```

<210> SEQ ID NO 77
<211> LENGTH: 316
<212> TYPE: PRT
<213> ORGANISM: Vulcanisaeta moutnovskia

<400> SEQUENCE: 77

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Ala Tyr Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
```

```
                290                 295                 300
Leu Ile Asp Asn Pro Arg Arg Leu Phe Thr Gly Arg
305                 310                 315

<210> SEQ ID NO 78
<211> LENGTH: 951
<212> TYPE: DNA
<213> ORGANISM: Vulcanisaeta moutnovskia

<400> SEQUENCE: 78
atggcggtgc gtattagcat tgccggtggt aatgaaattg atccgggtag catgggtctg     60
accctgtttc atgaacatct gcgtctgatt accgaagttg ttcgttggaa ttggcctcat    120
ctgtataacg aagatgaaga actgaaacgt gcaattgatg cagttaacgc agccaaaaaa    180
tacggcgtga aaccattat  tgatctgacc gttgcaggta ttggttgtga tgttcgcttt    240
aatgaaaaag ttgcaaaagc caccggtgtg aacattatta tgggcaccgg ttttatacc     300 tataccgaaa tcccgttcta tttcaaaaac cgtggtattg atagcctggt tgatgccttt    360
gttcatgata ttaccattgg tattcagggc accaataccc gtgcagcatt tgttaaagca    420
gtgattgata gcagcggtct gaccaaagat gttgaaatgg caattcgtgc agcagcaaaa    480
gcacatatca aaccgatgt  tccgattatc acccatagct tgttggtaa  taaaagcagc    540 ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatt tatctgccgc tggataaacg tgttaaaacc    720
gcaattgaac tgattaaacg cggttggatt gatcagctgc tgctgagcca tgattattgt    780
ccgaccattg atatttatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951

<210> SEQ ID NO 79
<211> LENGTH: 316
<212> TYPE: PRT
<213> ORGANISM: Vulcanisaeta moutnovskia

<400> SEQUENCE: 79

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140
```

```
Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Ile Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 80
<211> LENGTH: 951
<212> TYPE: DNA
<213> ORGANISM: Vulcanisaeta moutnovskia

<400> SEQUENCE: 80
atggcggtgc gtattagcat tgccggtggt aatgaaattg atccgggtag catgggtctg      60
accctgtttc atgaacatct gcgtctgatt ccgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaccgatgt tccgattatc acccatagct tgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg atgtttatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a            951

<210> SEQ ID NO 81
<211> LENGTH: 316
<212> TYPE: PRT
<213> ORGANISM: Vulcanisaeta moutnovskia
```

<400> SEQUENCE: 81

```
Met Ala Val Arg Ile Ser Ile Ala Gly Gly Asn Glu Ile Asp Pro Gly
1               5                   10                  15
Ser Met Gly Leu Thr Leu Phe His Glu His Leu Arg Leu Ile Thr Glu
            20                  25                  30
Val Val Arg Trp Asn Trp Pro His Leu Tyr Asn Glu Asp Glu Glu Leu
        35                  40                  45
Lys Arg Ala Ile Asp Ala Val Asn Ala Ala Lys Lys Tyr Gly Val Lys
    50                  55                  60
Thr Ile Ile Asp Leu Thr Val Ala Gly Ile Gly Cys Asp Val Arg Phe
65                  70                  75                  80
Asn Glu Lys Val Ala Lys Ala Thr Gly Val Asn Ile Ile Met Gly Thr
                85                  90                  95
Gly Phe Tyr Thr Tyr Thr Glu Ile Pro Phe Tyr Phe Lys Asn Arg Gly
            100                 105                 110
Ile Asp Ser Leu Val Asp Ala Phe Val His Asp Ile Thr Ile Gly Ile
        115                 120                 125
Gln Gly Thr Asn Thr Arg Ala Ala Phe Val Lys Ala Val Ile Asp Ser
    130                 135                 140
Ser Gly Leu Thr Lys Asp Val Glu Met Ala Ile Arg Ala Ala Ala Lys
145                 150                 155                 160
Ala His Ile Lys Thr Asp Val Pro Ile Ile Thr His Ser Phe Val Gly
                165                 170                 175
Asn Lys Ser Ser Leu Asp Leu Ile Arg Ile Phe Lys Glu Glu Gly Val
            180                 185                 190
Asp Leu Ala Arg Thr Val Ile Gly His Val Gly Asp Thr Asp Asp Ile
        195                 200                 205
Ser Phe Ile Glu Gln Ile Leu Arg Glu Gly Ala Phe Ile Gly Leu Asp
    210                 215                 220
Arg Phe Gly Leu Asp Ile Tyr Leu Pro Leu Asp Lys Arg Val Lys Thr
225                 230                 235                 240
Ala Ile Glu Leu Ile Lys Arg Gly Trp Ile Asp Gln Leu Leu Leu Ser
                245                 250                 255
His Asp Tyr Cys Pro Thr Ile Asp Val Tyr Pro Pro Glu Val Val Arg
            260                 265                 270
Ser Thr Val Pro Asp Trp Thr Met Thr Leu Ile Phe Glu Lys Val Ile
        275                 280                 285
Pro Arg Met Arg Ser Glu Gly Ile Thr Glu Gln Ile Asn Arg Val
    290                 295                 300
Leu Ile Asp Asn Pro Arg Arg Leu Phe Thr Gly Arg
305                 310                 315
```

<210> SEQ ID NO 82
<211> LENGTH: 951
<212> TYPE: DNA
<213> ORGANISM: Vulcanisaeta moutnovskia

<400> SEQUENCE: 82

```
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
```

-continued

```
aatgaaaaag ttgcaaaagc caccggtgtg aacattatta tgggcaccgg tttttatacc    300
tataccgaaa tcccgttcta tttcaaaaac cgtggtattg atagcctggt tgatgccttt    360
gttcatgata ttaccattgg tattcagggc accaataccc gtgcagcatt tgttaaagca    420
gtgattgata gcagcggtct gaccaaagat gttgaaatgg caattcgtgc agcagcaaaa    480
gcacatatca aaccgatgt  tccgattatc acccatagct tgttggtaa  taaaagcagc    540 ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatt tatctgccgc tggataaacg tgttaaaacc    720
gcaattgaac tgattaaacg cggttggatt gatcagctgc tgctgagcca tgattattgt    780
ccgaccattg atacctatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951
```

<210> SEQ ID NO 83
<211> LENGTH: 316
<212> TYPE: PRT
<213> ORGANISM: Vulcanisaeta moutnovskia

<400> SEQUENCE: 83

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255
```

His Asp Tyr Cys Pro Thr Ile Asp Thr Tyr Pro Pro Glu Val Val Arg
              260                 265                 270

Ser Thr Val Pro Asp Trp Thr Met Thr Leu Ile Phe Glu Lys Val Ile
         275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 84
<211> LENGTH: 951
<212> TYPE: DNA
<213> ORGANISM: Vulcanisaeta moutnovskia

<400> SEQUENCE: 84
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt      240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaccgatgt tccgattatc acccatagct tgttggtaa taaaagcagc       540 ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg attgctatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a              951

<210> SEQ ID NO 85
<211> LENGTH: 316
<212> TYPE: PRT
<213> ORGANISM: Vulcanisaeta moutnovskia

<400> SEQUENCE: 85

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Cys Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 86
<211> LENGTH: 951
<212> TYPE: DNA
<213> ORGANISM: Vulcanisaeta moutnovskia

<400> SEQUENCE: 86
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaccgatgt tccgattatc acccatagct tgttggtaa taaaagcagc     540 ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattatctg     780
ccgacctttg atgcatatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a            951

<210> SEQ ID NO 87
<211> LENGTH: 316
<212> TYPE: PRT
<213> ORGANISM: Vulcanisaeta moutnovskia

<400> SEQUENCE: 87

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Leu Pro Thr Phe Asp Ala Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 88
<211> LENGTH: 951
<212> TYPE: DNA
<213> ORGANISM: Vulcanisaeta moutnovskia

<400> SEQUENCE: 88

```
atggcggtgc gtattagcat tgccggtggt aatgaaattg atccgggtag catgggtctg    60
accctgtttc atgaacatct gcgtgcaatt accgaagttg ttcgttggaa ttggcctcat   120
ctgtataacg aagatgaaga attgaaacgt gcaattgatg cagttaacgc agccaaaaaa   180
tacggcgtga aaaccattat tgatctgacc gttgcaggta ttggttgtga tgttcgcttt   240
aatgaaaaag ttgcaaaagc caccggtgtg aacattatta tgggcaccgg tttttggacc   300
tataccgaaa tcccgttcta tttcaaaaac cgtggtattg atagcctggt tgatgccttt   360
gttcatgata ttaccattgg tattcagggc accaataccc gtgcagcatt tgttaaagca   420
gtgattgata gcagcggtct gaccaaagat gttgaaatgg caattcgtgc agcagcaaaa   480
gcacatatca aaccgatgt tccgattatc acccatagct tgttggtaa taaaagcagc   540
ctggatctga tccgcatttt caaagaagaa ggcgttgatc tggcacgtac cgttattggt   600
catgttggtg ataccgatga tatcagcttt attgagcaga ttctgcgtga aggtgcattt   660
attggtctgg atcgttttgg cctggatatg tatctgccgc tggataaacg tgttaaaacc   720
gcaattgaac tgattaaacg cggttggatt gatcagctgc tgctgagcca tgattattgt   780
ccgaccattg atatgtatcc gcctgaagtt gtgcgtagca ccgttccgga ttggaccatg   840
accctgattt ttgagaaagt tattccgcgt atgcgtagca aggtattac ggaagaacaa   900
attaatcgcg tgctgattga taatccgcgt cgtctgttta ccggtcgtta a            951
```

<210> SEQ ID NO 89
<211> LENGTH: 316
<212> TYPE: PRT
<213> ORGANISM: Vulcanisaeta moutnovskia

<400> SEQUENCE: 89

Met Ala Val Arg Ile Ser Ile Ala Gly Gly Asn Glu Ile Asp Pro Gly
1               5                   10                  15
Ser Met Gly Leu Thr Leu Phe His Glu His Leu Arg Ala Ile Thr Glu
            20                  25                  30
Val Val Arg Trp Asn Trp Pro His Leu Tyr Asn Glu Asp Glu Glu Leu
        35                  40                  45
Lys Arg Ala Ile Asp Ala Val Asn Ala Ala Lys Lys Tyr Gly Val Lys
    50                  55                  60
Thr Ile Ile Asp Leu Thr Val Ala Gly Ile Gly Cys Asp Val Arg Phe
65                  70                  75                  80
Asn Glu Lys Val Ala Lys Ala Thr Gly Val Asn Ile Ile Met Gly Thr
                85                  90                  95
Gly Phe Trp Thr Tyr Thr Glu Ile Pro Phe Tyr Phe Lys Asn Arg Gly
            100                 105                 110
Ile Asp Ser Leu Val Asp Ala Phe Val His Asp Ile Thr Ile Gly Ile
        115                 120                 125
Gln Gly Thr Asn Thr Arg Ala Ala Phe Val Lys Ala Val Ile Asp Ser
    130                 135                 140
Ser Gly Leu Thr Lys Asp Val Glu Met Ala Ile Arg Ala Ala Ala Lys
145                 150                 155                 160
Ala His Ile Lys Thr Asp Val Pro Ile Ile Thr His Ser Phe Val Gly
                165                 170                 175
Asn Lys Ser Ser Leu Asp Leu Ile Arg Ile Phe Lys Glu Glu Gly Val
            180                 185                 190
Asp Leu Ala Arg Thr Val Ile Gly His Val Gly Asp Thr Asp Asp Ile
        195                 200                 205

```
Ser Phe Ile Glu Gln Ile Leu Arg Glu Gly Ala Phe Ile Gly Leu Asp
    210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Met Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Gly Gln Ile Asn Arg Val
    290                 295                 300

Leu Ile Asp Asn Pro Arg Arg Leu Phe Thr Gly Arg
305                 310                 315
```

<210> SEQ ID NO 90
<211> LENGTH: 951
<212> TYPE: DNA
<213> ORGANISM: Vulcanisaeta moutnovskia

<400> SEQUENCE: 90

```
atggcggtgc gtattagcat tgccggtggt aatgaaattg atccgggtag catgggtctg    60
accctgtttc atgaacatct gcgtgcaatt accgaagttg ttcgttggaa ttggcctcat   120
ctgtataacg aagatgaaga attgaaacgt gcaattgatg cagttaacgc agccaaaaaa   180
tacggcgtga aaccattat tgatctgacc gttgcaggta ttggttgtga tgttcgcttt   240
aatgaaaaag ttgcaaaagc caccggtgtg aacattatta tgggcaccgg ttttggacc   300
tataccgaaa tcccgttcta tttcaaaaac cgtggtattg atagcctggt tgatgccttt   360
gttcatgata ttaccattgg tattcagggc accaataccc gtgcagcatt tgttaaagca   420
gtgattgata gcagcggtct gaccaaagat gttgaaatgg caattcgtgc agcagcaaaa   480
gcacatatca aaaccgatgt tccgattatc acccatagct tgttggtaa taaaagcagc   540
ctggatctga tccgcatttt caaagaagaa ggcgttgatc tggcacgtac cgttattggt   600
catgttggtg ataccgatga tatcagcttt attgagcaga ttctgcgtga aggtgcattt   660
attggtctgg atcgttttgg cctggatatt tatctgccgc tggataaacg tgttaaaacc   720
gcaattgaac tgattaaacg cggttggatt gatcagctgc tgctgagcca tgattattgt   780
ccgaccattg atctgtatcc gcctgaagtt gtgcgtagca ccgttccgga ttggaccacg   840
accctgattt tgagaaagt tattccgcgt atgcgtagcg aaggtattac ggaagaacaa   900
attaatcgcg tgctgattga taatccgcgt cgtctgttta ccggtcgtta a           951
```

<210> SEQ ID NO 91
<211> LENGTH: 316
<212> TYPE: PRT
<213> ORGANISM: Vulcanisaeta moutnovskia

<400> SEQUENCE: 91

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
```

```
            50                  55                  60
Thr Ile Ile Asp Leu Thr Val Ala Gly Ile Gly Cys Asp Val Arg Phe
 65                  70                  75                  80

Asn Glu Lys Val Ala Lys Ala Thr Gly Val Asn Ile Ile Met Gly Thr
                 85                  90                  95

Gly Phe Trp Thr Tyr Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
            260                 265                 270

Ser Thr Val Pro Asp Trp Thr Thr Thr Leu Ile Phe Glu Lys Val Ile
        275                 280                 285

Pro Arg Met Arg Ser Glu Gly Ile Thr Glu Glu Gln Ile Asn Arg Val
290                 295                 300

Leu Ile Asp Asn Pro Arg Arg Leu Phe Thr Gly Arg
305                 310                 315

<210> SEQ ID NO 92
<211> LENGTH: 951
<212> TYPE: DNA
<213> ORGANISM: Vulcanisaeta moutnovskia

<400> SEQUENCE: 92
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattata tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaccgatgt tccgattatc acccatagct tgttggtaa taaaagcagc     540 ctggatctga tccgcatttt caaagaagaa ggcgttgatc tggcacgtac cgttattggt     600
catgttggtg ataccgatga tatcagcttt attgagcaga ttctgcgtga aggtgcattt     660
```

-continued

```
attggtctgg atcgttttgg cctggatatt tatctgccgc tggataaacg tgttaaaacc    720
gcaattgaac tgattaaacg cggttggatt gatcagctgc tgctgagcca tgattatgct    780
ccgaccattg atatgtatcc gcctgaagtt gtgcgtagca ccgttccgga ttggaccacg    840
accctgattt ttgagaaagt tattccgcgt atgcgtagcg aaggtattac ggaagaacaa    900
attaatcgcg tgctgattga taatccgcgt cgtctgttta ccggtcgtta a             951
```

<210> SEQ ID NO 93
<211> LENGTH: 316
<212> TYPE: PRT
<213> ORGANISM: Vulcanisaeta moutnovskia

<400> SEQUENCE: 93

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
    195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Ala Pro Thr Ile Asp Met Tyr Pro Pro Glu Val Val Arg
            260                 265                 270

Ser Thr Val Pro Asp Trp Thr Thr Thr Leu Ile Phe Glu Lys Val Ile
    275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 94
<211> LENGTH: 951
<212> TYPE: DNA
<213> ORGANISM: Vulcanisaeta moutnovskia

<400> SEQUENCE: 94

```
atggcggtgc gtattagcat tgccggtggt aatgaaattg atccgggtag catgggtctg      60
accctgtttc atgaacatct gcgtgcaatt accgaagttg ttcgttggaa ttggcctcat     120
ctgtataacg aagatgaaga attgaaacgt gcaattgatg cagttaacgc agccaaaaaa     180
tacggcgtga aaaccattat tgatctgacc gttgcaggta ttggttgtga cacccgcttt     240
aatgaaaaag ttgcaaaagc caccggtgtg aacattatta tgggcaccgg tttttggacc     300
tttaccgaaa tcccgttcta tttcaaaaac cgtggtattg atagcctggt tgatgccttt     360
gttcatgata ttaccattgg tattcagggc accccgaccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct ttgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cgtggatatt tatctgccgc tggataaacg tgttaaaacc     720
gcaattgaac tgattaaacg cggttggatt gatcagctgc tgctgagcca tgattattgt     780
ccgaccattg attggtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a             951
```

<210> SEQ ID NO 95
<211> LENGTH: 316
<212> TYPE: PRT
<213> ORGANISM: Vulcanisaeta moutnovskia

<400> SEQUENCE: 95

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Thr Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Pro Thr Arg Ala Ala Phe Val Lys Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
```

```
                       165                 170                 175
Asn Lys Ser Ser Leu Asp Leu Ile Arg Ile Phe Lys Glu Glu Gly Val
                180                 185                 190

Asp Leu Ala Arg Thr Val Ile Gly His Val Gly Asp Thr Asp Asp Ile
            195                 200                 205

Ser Phe Ile Glu Gln Ile Leu Arg Glu Gly Ala Phe Ile Gly Leu Asp
        210                 215                 220

Arg Phe Gly Val Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 96
<211> LENGTH: 951
<212> TYPE: DNA
<213> ORGANISM: Vulcanisaeta moutnovskia

<400> SEQUENCE: 96

```
atggcggtgc gtattagcat tgccggtggt aatgaaattg atccgggtag catgggtctg        60
accctgtttc atgaacatct gcgtctgatt accgaagttg ttcgttggaa ttggccccat       120
ctgtataacg aagatgaaga attgaaacgt gcaattgatg cagttaacgc agccaaaaaa       180
tacggcgtga aaaccattat tgatctgacc gttgcaggta ttggttgtga tgttcgcttt       240
aatgaaaaag ttgcaaaagc caccggtgtg aacattatta tgggcaccgg ttttatacc       300
tttaccgaaa tcccgttcta tttcaaaaac cgtggtattg atagcctggt tgatgccttt       360
gttcatgatt taaccattgg tattcagggc accaataccc gtgcagcatt tgttaaagca       420
gtgattgata gcagcggtct gaccaaagat gttgaaatgg ccattcgtgc agcagcaaaa       480
gcacatatca aaaccgatgt tccgattatc acccatagct tgttggtaa taaaagcagc       540
ctggatctga tccgcatttt caaagaagaa ggcgttgatc tggcacgtac cgttattggt       600
catgttggtg ataccgatga tatcagcttt attgagcaga ttctgcgtga aggtgcattt       660
attggtctgg atcgtttttgg cctggatatg tctctgccgc tggataaacg tgttaaaacc       720
gcaattgaac tgattaaacg cggttggatt gatcagctgc tgctgagcca tgattattgt       780
ccgaccattg atctgtatcc gcctgaagtt gtgcgtagca ccgttccgga ttggaccatg       840
accctgattt ttgagaaagt tattccgcgt atgcgtagcg aaggtattac ggaagaacaa       900
attaatcgcg tgctgattga taatccgcgt cgtctgttta ccggtcgtta a             951
```

<210> SEQ ID NO 97
<211> LENGTH: 316
<212> TYPE: PRT
<213> ORGANISM: Vulcanisaeta moutnovskia

<400> SEQUENCE: 97

```
Met Ala Val Arg Ile Ser Ile Ala Gly Gly Asn Glu Ile Asp Pro Gly
1               5                   10                  15
```

```
Ser Met Gly Leu Thr Leu Phe His Glu His Leu Arg Leu Ile Thr Glu
         20                  25                  30

Val Val Arg Trp Asn Trp Pro His Leu Tyr Asn Glu Asp Glu Glu Leu
         35                  40                  45

Lys Arg Ala Ile Asp Ala Val Asn Ala Ala Lys Lys Tyr Gly Val Lys
 50                  55                  60

Thr Ile Ile Asp Leu Thr Val Ala Gly Ile Gly Cys Asp Val Arg Phe
 65                  70                  75                  80

Asn Glu Lys Val Ala Lys Ala Thr Gly Val Asn Ile Ile Met Gly Thr
             85                  90                  95

Gly Phe Tyr Thr Phe Thr Glu Ile Pro Phe Tyr Phe Lys Asn Arg Gly
            100                 105                 110

Ile Asp Ser Leu Val Asp Ala Phe Val His Asp Leu Thr Ile Gly Ile
            115                 120                 125

Gln Gly Thr Asn Thr Arg Ala Ala Phe Val Lys Ala Val Ile Asp Ser
130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
            165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
            195                 200                 205

Ser Phe Ile Glu Gln Ile Leu Arg Glu Gly Ala Phe Ile Gly Leu Asp
    210                 215                 220

Arg Phe Gly Leu Asp Met Ser Leu Pro Leu Asp Lys Arg Val Lys Thr
225                 230                 235                 240

Ala Ile Glu Leu Ile Lys Arg Gly Trp Ile Asp Gln Leu Leu Leu Ser
            245                 250                 255

His Asp Tyr Cys Pro Thr Ile Asp Leu Tyr Pro Pro Glu Val Val Arg
            260                 265                 270

Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 98
<211> LENGTH: 951
<212> TYPE: DNA
<213> ORGANISM: Vulcanisaeta moutnovskia

<400> SEQUENCE: 98

```
atggcggtgc gtattagcat tgccggtggt aatgaaattg atccgggtag catgggtctg      60
accctgtttc atgaacatct gcgtctgatt accgaagttg ttcgttggaa ttggccccat     120
ctgtataacg aagatgaaga attgaaacgt gcaattgatg cagttaacgc agccaaaaaa     180
tacggcgtga aaccattat tgatctgagt gttgcaggta ttggttgtga tgttcgcttt     240
aatgaaaaag ttgcaaaagc caccggtgtg aacattatta gggcaccgg ttttatacc     300 tataccgaaa tccgttct tttcaaaaac cgtggtattg atagcctggt tgatgccttt     360
gttcatgata ttaccattgg tattcagggc accccgaccc gtgcagcatt tgttaaagca     420
```

```
gtgattgata gcagcggtct gaccaaagat gttgaaatgg caattcgtgc agcagcaaaa    480
gcacatatca aaaccgatgt tccgattatc acccatagct tgttggtaa taaaagcagc     540 ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatg tctctgccgc tggataaacg tgttaaaacc    720
gcaattgaac tgattaaacg cggttggatt gatcagctgc tgctgagcca tgattattgt    780
ccgaccattg atatgtatcc gcctgaagtt gtgcgtagcc cggttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951
```

<210> SEQ ID NO 99
<211> LENGTH: 316
<212> TYPE: PRT
<213> ORGANISM: Vulcanisaeta moutnovskia

<400> SEQUENCE: 99

```
Met Ala Val Arg Ile Ser Ile Ala Gly Gly Asn Glu Ile Asp Pro Gly
 1               5                  10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Leu
             35                  40                  45

Lys Arg Ala Ile Asp Ala Val Asn Ala Ala Lys Lys Tyr Gly Val Lys
 50                  55                  60

Thr Ile Ile Asp Leu Ser Val Ala Gly Ile Gly Cys Asp Val Arg Phe
 65                  70                  75                  80

Asn Glu Lys Val Ala Lys Ala Thr Gly Val Asn Ile Ile Met Gly Thr
                 85                  90                  95

Gly Phe Tyr Thr Tyr Thr Glu Ile Pro Phe Tyr Phe Lys Asn Arg Gly
                100                 105                 110

Ile Asp Ser Leu Val Asp Ala Phe Val His Asp Ile Thr Ile Gly Ile
             115                 120                 125

Gln Gly Thr Pro Thr Arg Ala Ala Phe Val Lys Ala Val Ile Asp Ser
 130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
         195                 200                 205

Ser Phe Ile Glu Gln Ile Leu Arg Glu Gly Ala Phe Ile Gly Leu Asp
    210                 215                 220

Arg Phe Gly Leu Asp Met Ser Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Met Tyr Pro Pro Glu Val Val Arg
            260                 265                 270

Ser Pro Val Pro Asp Trp Thr Met Thr Leu Ile Phe Glu Lys Val Ile
```

```
              275                 280                 285
Pro Arg Met Arg Ser Glu Gly Ile Thr Glu Glu Gln Ile Asn Arg Val
              290                 295                 300

Leu Ile Asp Asn Pro Arg Arg Leu Phe Thr Gly Arg
305                 310                 315

<210> SEQ ID NO 100
<211> LENGTH: 951
<212> TYPE: DNA
<213> ORGANISM: Vulcanisaeta moutnovskia

<400> SEQUENCE: 100
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180
tacggcgtga aaaccattat tgatctgagt gttgcaggta ttggttgtga tacccgcttt     240
aatgaaaaag ttgcaaaagc caccggtgtg aacattatta tgggcaccgg ttttggacc      300 tttaccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct ttgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgtttttgg cctggatatg tatctgccgc tggataaacg tgttaaaacc     720
gcaattgaac tgattaaacg cggttggatt gatcagctgc tgctgagcca tgattattgt     780
ccgaccattg atctgtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a              951

<210> SEQ ID NO 101
<211> LENGTH: 316
<212> TYPE: PRT
<213> ORGANISM: Vulcanisaeta moutnovskia

<400> SEQUENCE: 101

Met Ala Val Arg Ile Ser Ile Ala Gly Gly Asn Glu Ile Asp Pro Gly
1               5                  10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Ser Val Ala Gly Ile Gly Cys Asp Thr Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125
```

```
Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
                180                 185                 190

Asp Leu Ala Arg Thr Val Ile Gly His Val Gly Asp Thr Asp Asp Ile
                195                 200                 205

Ser Phe Ile Glu Gln Ile Leu Arg Glu Gly Ala Phe Ile Gly Leu Asp
210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
                260                 265                 270

Ser Thr Val Pro Asp Trp Thr Met Thr Leu Ile Phe Glu Lys Val Ile
                275                 280                 285

Pro Arg Met Arg Ser Glu Gly Ile Thr Glu Glu Gln Ile Asn Arg Val
290                 295                 300

Leu Ile Asp Asn Pro Arg Arg Leu Phe Thr Gly Arg
305                 310                 315

<210> SEQ ID NO 102
<211> LENGTH: 951
<212> TYPE: DNA
<213> ORGANISM: Vulcanisaeta moutnovskia

<400> SEQUENCE: 102
atggcggtgc gtattagcat tgccggtgaa atgaaattg atccgggtag catgggtctg      60
accctgtttc atgaacatct gcgtctgatt accgaagttg ttcgttggaa ttggcctcat    120
ctgtataacg aagatgaaga actgaaacgt gcaattgatg cagttaacgc agccaaaaaa    180
tacggcgtga aaccattat tgatctgacc gttgcaggta ttggttgtga tgttcgcttt    240
aatgaaaaag ttgcaaaagc caccggtgtg aacattatta tgggcaccgg ttttggacc    300 tttaccgaaa tcccgttcta tttcaaaaac cgtggtattg atagcctggt tgatgccttt    360
gttcatgata ttaccattgg tattcagggc accaataccc gtgcagcatt tgttaaagca    420
gtgattgata gcagcggtct gaccaaagat gttgaaatgg caattcgtgc agcagcaaaa    480
gcacatatca aaaccgatgt tccgattatc ccccatagct tgttggtaa taaaagcagc    540 ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatg tatctgccgc tggataaacg tgttaaaacc    720
gcaattgaac tgattaaacg cggttggatt gatcagctgc tgctgagcca tgattattgt    780
ccgaccattg attggtatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a              951

<210> SEQ ID NO 103
```

<211> LENGTH: 316
<212> TYPE: PRT
<213> ORGANISM: Vulcanisaeta moutnovskia

<400> SEQUENCE: 103

Met Ala Val Arg Ile Ser Ile Ala Gly Glu Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Leu
        35                  40                  45

Lys Arg Ala Ile Asp Ala Val Asn Ala Ala Lys Lys Tyr Gly Val Lys
50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
290                 295                 300

Leu Ile Asp Asn Pro Arg Arg Leu Phe Thr Gly Arg
305                 310                 315

<210> SEQ ID NO 104
<211> LENGTH: 951
<212> TYPE: DNA
<213> ORGANISM: Vulcanisaeta moutnovskia

<400> SEQUENCE: 104
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180

```
tacggcgtga aaaccattat tgatctgacc gttgcaggta ttggttgtga tgttcgcttt      240
aatgaaaaag ttgcaaaagc caccggtgtg aacattatta tgggcaccgg tttttatacc      300
tataccgaaa tcccgttcta tttcaaaaac cgtggtattg atagcctggt tgatgccttt      360
gttcatgata ttaccattgg tattcagggc accaataccc gtgcagcatt tgttaaagca      420
gtgattgata gcagcggtct gaccaaagat gttgaaatgg caattcgtgc agcagcaaaa      480
gcacatatca aaaccgatgt tccgattatc acccatagct tgttggtaa taaaagcagc       540 ctggatctga tccgcatttt caaagaagaa ggcgttgatc tggcacgtac cgttattggt      600
catgttggtg ataccgatga tatcagcttt attgagcaga ttctgcgtga aggtgcattt      660
attggtctgg atcgttttgg cctggatatt tatctgccgc tggataaacg tgttaaaacc      720
gcaattgaac tgattaaacg cggttggatt gatcagctgc tgctgagcca tgattattgt      780
ccgaccattg atttttatcc gcctgaagtt gtgcgtagca ccgttccgga ttggaccatg      840
accctgattt ttgagaaagt tattccgcgt atgcgtagcg aaggtattac ggaagaacaa      900
attaatcgcg tgctgattga taatccgcgt cgtctgttta ccggtcgtta a               951
```

<210> SEQ ID NO 105
<211> LENGTH: 316
<212> TYPE: PRT
<213> ORGANISM: Vulcanisaeta moutnovskia

<400> SEQUENCE: 105

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240
```

```
Ala Ile Glu Leu Ile Lys Arg Gly Trp Ile Asp Gln Leu Leu Leu Ser
                245                 250                 255

His Asp Tyr Cys Pro Thr Ile Asp Phe Tyr Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 106
<211> LENGTH: 951
<212> TYPE: DNA
<213> ORGANISM: Vulcanisaeta moutnovskia
<400> SEQUENCE: 106

| | | | | | |
|---|---|---|---|---|---|
| atggcggtgc | gtattagcat | tgccggtggt | aatgaaattg | atccgggtag | catgggtctg | 60 |
| accctgtttc | atgaacatct | gcgtctgatt | accgaagttg | ttcgttggaa | ttggcctcat | 120 |
| ctgtataacg | aagatgaaga | attgaaacgt | gcaattgatg | cagttaacgc | agccaaaaaa | 180 |
| tacggcgtga | aaccattat | tgatctgagt | gttgcaggta | ttggttgtga | tgttcgcttt | 240 |
| aatgaaaaag | ttgcaaaagc | caccggtgtg | aacattatta | tgggcaccgg | ttttttggacc | 300 |
| tttaccgaaa | tcccgttcta | tttcaaaaac | cgtggtattg | atagcctggt | tgatgccttt | 360 |
| gttcatgata | ttaccattgg | tattcagggc | accccgaccc | gtgcagcatt | tgttaaagca | 420 |
| gtgattgata | gcagcggtct | gaccaaagat | gttgaaatgg | caattcgtgc | agcagcaaaa | 480 |
| gcacatatca | aaaccgatgt | tccgattatc | acccatagct | ttgttggtaa | taaaagcagc | 540 |
| ctggatctga | tccgcatttt | caaagaagaa | ggcgttgatc | tggcacgtac | cgttattggt | 600 |
| catgttggtg | ataccgatga | tatcagcttt | attgagcaga | ttctgcgtga | aggtgcattt | 660 |
| attggtctgg | atcgtttttgg | cctggatatg | tatctgccgc | tggataaacg | tgttaaaacc | 720 |
| gcaattgaac | tgattaaacg | cggttggatt | gatcagctgc | tgctgagcca | tgattattgt | 780 |
| ccgaccattg | attggtatcc | gcctgaagtt | gtgcgtagca | ccgttccgga | ttggaccatg | 840 |
| accctgattt | ttgagaaagt | tattccgcgt | atgcgtagcg | aaggtattac | ggaagaacaa | 900 |
| attaatcgcg | tgctgattga | taatccgcgt | cgtctgttta | ccggtcgtta | a | 951 |

<210> SEQ ID NO 107
<211> LENGTH: 316
<212> TYPE: PRT
<213> ORGANISM: Vulcanisaeta moutnovskia
<400> SEQUENCE: 107

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Ser Val Ala Gly Ile Gly Cys Asp Val Arg Phe
65                  70                  75                  80
```

```
Asn Glu Lys Val Ala Lys Ala Thr Gly Val Asn Ile Ile Met Gly Thr
             85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
            115                 120                 125

Gln Gly Thr Pro Thr Arg Ala Ala Phe Val Lys Ala Val Ile Asp Ser
            130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
            195                 200                 205

Ser Phe Ile Glu Gln Ile Leu Arg Glu Gly Ala Phe Ile Gly Leu Asp
            210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270

Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
            290                 295                 300

Leu Ile Asp Asn Pro Arg Arg Leu Phe Thr Gly Arg
305                 310                 315

<210> SEQ ID NO 108
<211> LENGTH: 951
<212> TYPE: DNA
<213> ORGANISM: Vulcanisaeta moutnovskia

<400> SEQUENCE: 108
atggcggtgc gtattagcat tgccggtggt aatgaaattg atccgggtag catgggtctg      60
accctgtttc atgaacatct gcgtgcaatt accgaagttg ttcgttggaa ttggcctcat     120
ctgtataacg aagatgaaga actgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc     540 ctggatctga tccgcatttt caagaagaa ggcgttgatc tggcacgtac cgttattggt     600
catgttggtg ataccgatga tatcagcttt attgagcaga ttctgcgtga aggtgcattt     660
attggtctgg atcgttttgg cgtggatatt tatctgccgc tggataaacg tgttaaaacc     720
gcaattgaac tgattaaacg cggttggatt gatcagctgc tgctgagcca tgattattgt     780
```

```
ccgaccattg atctgtatcc gcctgaagtt gtgcgtagca ccgttccgga ttggaccatg      840
accctaattt tgagaaagt tattccgcgt atgcgtagcg aaggtattac ggaagaacaa       900
attaatcgcg tgctgattga taatccgcgt cgtctgttta ccggtcgtta a              951
```

<210> SEQ ID NO 109
<211> LENGTH: 316
<212> TYPE: PRT
<213> ORGANISM: Vulcanisaeta moutnovskia

<400> SEQUENCE: 109

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Val Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 110
<211> LENGTH: 951
<212> TYPE: DNA
<213> ORGANISM: Vulcanisaeta moutnovskia

<400> SEQUENCE: 110

```
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180
tacggcgtga aaaccattat tgatgtgagt gttgcaggta ttggttgtga tgttcgcttt     240
aatgaaaaag ttgcaaaagc caccggtgtg aacattata tgggcaccgg tttttgacc      300
tttaccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgagatgg caattcgtgc agcagcaaaa     480
gcacatatca aaaccgatgt tccgattatc acccatagct ttgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatg tatctgccgc tggataaacg tgttaaaacc     720
gcaattgaac tgattaaacg cggttggatt gatcagctgc tgctgagcca tgattatgct     780
ccgaccattg atctgtatcc gcctgaagtt gtgcgtagca ccgttccgga ttggaccacg     840
accctgattt ttgagaaagt tattccgcgt atgcgtagcg aaggtattac ggaagaacaa     900
attaatcgcg tgctgattga taatccgcgt cgtctgttta ccggtcgtta a              951
```

<210> SEQ ID NO 111
<211> LENGTH: 316
<212> TYPE: PRT
<213> ORGANISM: Vulcanisaeta moutnovskia

<400> SEQUENCE: 111

```
Met Ala Val Arg Ile Ser Ile Ala Gly Gly Asn Glu Ile Asp Pro Gly
  1               5                  10                  15

Ser Met Gly Leu Thr Leu Phe His Glu His Leu Arg Leu Ile Thr Glu
             20                  25                  30

Val Val Arg Trp Asn Trp Pro His Leu Tyr Asn Glu Asp Glu Glu Leu
         35                  40                  45

Lys Arg Ala Ile Asp Ala Val Asn Ala Ala Lys Lys Tyr Gly Val Lys
     50                  55                  60

Thr Ile Ile Asp Val Ser Val Ala Gly Ile Gly Cys Asp Val Arg Phe
 65                  70                  75                  80

Asn Glu Lys Val Ala Lys Ala Thr Gly Val Asn Ile Ile Met Gly Thr
                 85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190
```

Asp Leu Ala Arg Thr Val Ile Gly His Val Gly Asp Thr Asp Asp Ile
            195                 200                 205

Ser Phe Ile Glu Gln Ile Leu Arg Glu Gly Ala Phe Ile Gly Leu Asp
    210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Ala Pro Thr Ile Asp Leu Tyr Pro Glu Val Val Arg
            260                 265                 270

Ser Thr Val Pro Asp Trp Thr Thr Leu Ile Phe Glu Lys Val Ile
            275                 280                 285

Pro Arg Met Arg Ser Glu Gly Ile Thr Glu Glu Gln Ile Asn Arg Val
            290                 295                 300

Leu Ile Asp Asn Pro Arg Arg Leu Phe Thr Gly Arg
305                 310                 315

<210> SEQ ID NO 112
<211> LENGTH: 951
<212> TYPE: DNA
<213> ORGANISM: Vulcanisaeta moutnovskia

<400> SEQUENCE: 112
atggcggtgc gtattagcat tgccggtggt aatgaaattg atccgggtag catgggtctg        60
accctgtttc atgaacatct gcgtctgatt accgaagttg ttcgttggaa ttggcctcat       120
ctgtataacg aagatgaaga actgaaacgt gcaattgatg cagttaacgc agccaaaaaa       180
tacggcgtga aaccattat tgatctgagt gttgcaggta ttggttgtga tgttcgcttt       240
aatgaaaaag ttgcaaaagc caccggtgtg aacattatta tgggcaccgg ttttttgacc       300
tttaccgaaa tcccgttcta tttcaaaaac cgtggtattg atagcctggt tgatgccttt       360
gttcatgata ttaccattgg tattcagggc accccgaccc gtgcagcatt tgttaaagca       420
gtgattgata gcagcggtct gaccaaagat gttgaaatgg caattcgtgc agcagcaaaa       480
gcacatatca aaccaatgt tccgattatc acccatagcc ttgttggtaa taaaagcagc       540
ctggatctga tccgcatttt caaagaagaa ggcgttgatc tggcacgtac cgttattggt       600
catgttggtg ataccgatga tatcagcttt attgagcaga ttctgcgtga aggtgcattt       660
attggtctgg atcgttttgg cgtggatatt tatctgccgc tggataaacg tgttaaaacc       720
gcaattgaac tgattaaacg cggttggatt gatcagctgc tgctgagcca tgattattgt       780
ccgaccattg atatgtatcc gcctgaagtt gtgcgtagca ccgttccgga ttggaccatg       840
accctgattt ttgagaaagt tattccgcgt atgcgtagcg aaggtattac ggaagaacaa       900
attaatcgcg tgctgattga taatccgcgt cgtctgttta ccggtcgtta a              951

<210> SEQ ID NO 113
<211> LENGTH: 316
<212> TYPE: PRT
<213> ORGANISM: Vulcanisaeta moutnovskia

<400> SEQUENCE: 113

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu

```
                35                  40                  45
Lys Arg Ala Ile Asp Ala Val Asn Ala Lys Lys Tyr Gly Val Lys
        50                  55                  60

Thr Ile Ile Asp Leu Ser Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Pro Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asn Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Val Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Met Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315
```

<210> SEQ ID NO 114
<211> LENGTH: 951
<212> TYPE: DNA
<213> ORGANISM: Vulcanisaeta moutnovskia

<400> SEQUENCE: 114

```
atggcggtgc gtattagcat tgccggtggt aatgaaattg atccgggtag catgggtctg      60
accctgtttc atgaacatct gcgtctgatt accgaagttg ttcgttggaa ttggccccat     120
ctgtataacg aagatgaaga attgaaacgt gcaattgatg cagttaacgc agccaaaaaa     180
tacggcgtga aaaccattat tgatctgagt gttgcaggta ttggttgtga tgttcgcttt     240
aatgaaaaag ttgcaaaagc caccggtgtg aacattatta tgggcaccgg tttttggacc     300
tttaccgaaa tcccgttcta tttcaaaaac cgtggtattg atagcctggt tgatgccttt     360
gttcatgata ttaccattgg tattcagggc accccgaccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc     540
```

```
ctggatctga tccgcattt  caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatt tatctgccgc tggataaacg tgttaaaacc    720
gcaattgaac tgattaaacg cggttggatt gatcagctgc tgctgagcca tgattattgt    780
ccgaccattg attggtatcc gcctgaagtt gtgcgtagca ccgttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951
```

<210> SEQ ID NO 115
<211> LENGTH: 316
<212> TYPE: PRT
<213> ORGANISM: Vulcanisaeta moutnovskia

<400> SEQUENCE: 115

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Ser Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Pro Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300
```

Leu Ile Asp Asn Pro Arg Arg Leu Phe Thr Gly Arg
305                 310                 315

<210> SEQ ID NO 116
<211> LENGTH: 951
<212> TYPE: DNA
<213> ORGANISM: Vulcanisaeta moutnovskia

<400> SEQUENCE: 116

| | | | | | |
|---|---|---|---|---|---|
| atggcggtgc | gtattagcat | tgccggtggt | aatgaaattg | atccgggtag | catgggtctg | 60 |
| accctgtttc | atgaacatct | gcgtgcaatt | accgaagttg | ttcgttggaa | ttggcctcat | 120 |
| ctgtataacg | aagatgaaga | attgaaacgt | gcaattgatg | cagttaacgc | agccaaaaaa | 180 |
| tacggcgtga | aaaccattat | tgatctgacc | gttgcaggta | ttggttgtga | tgttcgcttt | 240 |
| aatgaaaaag | ttgcaaaagc | caccggtgtg | aacattatta | tgggcaccgg | tttttggacc | 300 |
| tttaccgaaa | tcccgttcta | tttcaaaaac | cgtggtattg | atagcctggt | tgatgccttt | 360 |
| gttcatgata | ttaccattgg | tattcagggc | accaataccc | gtgcagcatt | tgttaaagca | 420 |
| gtgattgata | gcagcggtct | gaccaaagat | gttgaaatgg | caattcgtgc | agcagcaaaa | 480 |
| gcacatatca | aaaccgatgt | tccgattatc | acccatagct | tgttggtaa | taaaagcagc | 540 |
| ctggatctga | tccgcatttt | caaagaagaa | ggcgttgatc | tggcacgtac | cgttattggt | 600 |
| catgttggtg | ataccgatga | tatcagcttt | attgagcaga | ttctgcgtga | aggtgcattt | 660 |
| attggtctgg | atcgttttgg | cgtggatatt | tatctgccgc | tggataaacg | tgttaaaacc | 720 |
| gcaattgaac | tgattaaacg | cggttggatt | gatcagctgc | tgctgagcca | tgattattgt | 780 |
| ccgaccattg | attggtatcc | gcctgaagtt | gtgcgtagca | ccgttccgga | ttggaccatg | 840 |
| accctgattt | ttgagaaagt | tattccgcgt | atgcgtagcg | aaggtattac | ggaagaacaa | 900 |
| attaatcgcg | tgctgattga | taatccgcgt | cgtctgttta | ccggtcgtta | a | 951 |

<210> SEQ ID NO 117
<211> LENGTH: 316
<212> TYPE: PRT
<213> ORGANISM: Vulcanisaeta moutnovskia

<400> SEQUENCE: 117

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu
                20                  25                  30

Val Val Arg Trp Asn Trp Pro His Leu Tyr Asn Glu Asp Glu Glu Leu
            35                  40                  45

Lys Arg Ala Ile Asp Ala Val Asn Ala Ala Lys Lys Tyr Gly Val Lys
        50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
                100                 105                 110

Ile Asp Ser Leu Val Asp Ala Phe Val His Asp Ile Thr Ile Gly Ile
            115                 120                 125

Gln Gly Thr Asn Thr Arg Ala Ala Phe Val Lys Ala Val Ile Asp Ser
        130                 135                 140

Ser Gly Leu Thr Lys Asp Val Glu Met Ala Ile Arg Ala Ala Ala Lys

```
                145                 150                 155                 160
Ala His Ile Lys Thr Asp Val Pro Ile Ile Thr His Ser Phe Val Gly
                    165                 170                 175

Asn Lys Ser Ser Leu Asp Leu Ile Arg Ile Phe Lys Glu Glu Gly Val
                180                 185                 190

Asp Leu Ala Arg Thr Val Ile Gly His Val Gly Asp Thr Asp Asp Ile
                195                 200                 205

Ser Phe Ile Glu Gln Ile Leu Arg Glu Gly Ala Phe Ile Gly Leu Asp
210                 215                 220

Arg Phe Gly Val Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
                260                 265                 270

Ser Thr Val Pro Asp Trp Thr Met Thr Leu Ile Phe Glu Lys Val Ile
                275                 280                 285

Pro Arg Met Arg Ser Glu Gly Ile Thr Glu Glu Gln Ile Asn Arg Val
                290                 295                 300

Leu Ile Asp Asn Pro Arg Arg Leu Phe Thr Gly Arg
305                 310                 315

<210> SEQ ID NO 118
<211> LENGTH: 951
<212> TYPE: DNA
<213> ORGANISM: Vulcanisaeta moutnovskia

<400> SEQUENCE: 118
atggcggtgc gtattagcat tgccggtggt aatgaaattg atccgggtag catgggtctg        60
accctgtttc atgaacatct gcgtctgatt accgaagttg ttcgttggaa ttggcctcat       120
ctgtataacg aagatgaaga attgaaacgt gcaattgatg cagttaacgc agccaaaaaa       180
tacggcgtga aaccattat tgatctgagt gttgcaggta ttggttgtga tgttcgcttt        240
aatgaaaaag ttgcaaaagc caccggtgtg aacattatta tgggcaccgg ttttggacc       300
tttaccgaaa tcccgttcta tttcaaaaac cgtggtattg atagcctggt tgatgccttt       360
gttcatgata ttaccattgg tattcagggc accccgaccc gtgcagcatt tgttaaagca       420
gtgattgata gcagcggtct gaccaaagat gttgaaatgg caattcgtgc agcagcaaaa       480
gcacatatca aaaccgatgt tccgattatc acccatagct tgttggtaa taaaagcagc        540
ctggatctga tccgcatttt caagaagaa ggcgttgatc tggcacgtac cgttattggt        600
catgttggtg ataccgatga tatcagcttt attgagcaga ttctgcgtga aggtgcattt       660
attggtctgg atcgttttgg cctggatatg tatctgccgc tggataaacg tgttaaaacc       720
gcaattgaac tgattaaacg cggttggatt gatcagctgc tgctgagcca tgattattgt       780
ccgaccattg attggtatcc gcctgaagtt gtgcgtagca ccgttccgga ttggaccatg       840
accctgattt ttgagaaagt tattccgcgt atgcgtagcg aaggtattac ggaagaacaa       900
attaatcgcg tgctgattga taatccgcgt cgtctgttta ccggtcgtta a              951

<210> SEQ ID NO 119
<211> LENGTH: 316
<212> TYPE: PRT
<213> ORGANISM: Vulcanisaeta moutnovskia

<400> SEQUENCE: 119
```

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Ser Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Phe Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Pro Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Met Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 120
<211> LENGTH: 951
<212> TYPE: DNA
<213> ORGANISM: Vulcanisaeta moutnovskia

<400> SEQUENCE: 120
atggcggtgc gtattagcat tgccggtggt aatgaaattg atccgggtag catgggtctg      60
accctgtttc atgaacatct gcgtgcaatt accgaagttg tacgttggaa ttggcctcat     120
ctgtataacg aagatgaaga attgaaacgt gcaattgatg cagttaacgc agccaaaaaa     180
tacggcgtga aaaccattat tgatctgagt gttgcaggta ttggttgtga tgttcgcttt     240
aatgaaaaag ttgcaaaagc caccggtgtg aacattata tgggcaccgg ttttggacc     300

-continued

```
tataccgaaa tcccgttcta tttcaaaaac cgtggtattg atagcctggt tgatgccttt      360
gttcatgata ttaccattgg tattcagggc accaataccc gtgcagcatt tgttaaagca      420
gtgattgata gcagcggtct gaccaaagat gttgaaatgg caattcgtgc agcagcaaaa      480
gcacatatca aaaccgatgt tccgattatc acccatagct tgttggtaa taaaagcagc       540 ctggatctga tccgcatttt caagaagaa ggcgttgatc tggcacgtac cgttattggt       600
catgttggtg ataccgatga tatcagcttt attgagcaga ttctgcgtga aggtgcattt      660
attggtctgg atcgttttgg cctggatatt tatctgccgc tggataaacg tgttaaaacc      720
gcaattgaac tgattaaacg cggttggatt gatcagctgc tgctgagcca tgattattgt      780
ccgaccattg atctgtatcc gcctgaagtt gtgcgtagca ccgttccgga ttggaccatg      840
accctgattt ttgagaaagt tattccgcgt atgcgtagcg aaggtattac ggaagaacaa      900
attaatcgcg tgctgattga taatccgcgt cgtctgttta ccggtcgtta a              951
```

<210> SEQ ID NO 121
<211> LENGTH: 316
<212> TYPE: PRT
<213> ORGANISM: Vulcanisaeta moutnovskia
<400> SEQUENCE: 121

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Ser Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
```

```
              260                 265                 270
Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
        290                 295                 300

Leu Ile Asp Asn Pro Arg Arg Leu Phe Thr Gly Arg
305                 310                 315
```

<210> SEQ ID NO 122
<211> LENGTH: 951
<212> TYPE: DNA
<213> ORGANISM: Vulcanisaeta moutnovskia

<400> SEQUENCE: 122

```
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaatagatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc ccccatagct tgttggtaa taaaagcagc     540
ctggatctga tccgcatttt caagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg attgttatcc gcctgaagtt gtgcgtagca ccgttccgga ttggaccatg     840
accatgattt tgagaaagt tattccgcgt atgcgtagcg aaggtattac ggaagaacaa     900
attaatcgcg tgctgattga taatccgcgt cgtctgttta ccggtcgtta a             951
```

<210> SEQ ID NO 123
<211> LENGTH: 316
<212> TYPE: PRT
<213> ORGANISM: Vulcanisaeta moutnovskia

<400> SEQUENCE: 123

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110
```

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
            195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Cys Tyr Pro Pro Gly Val Val Arg
            260                 265                 270

Ser Thr Val Pro Asp Trp Thr Met Thr Met Ile Phe Glu Lys Val Ile
    275                 280                 285

Pro Arg Met Arg Ser Glu Gly Ile Thr Glu Glu Gln Ile Asn Arg Val
290                 295                 300

Leu Ile Asp Asn Pro Arg Arg Leu Phe Thr Gly Arg
305                 310                 315

<210> SEQ ID NO 124
<211> LENGTH: 951
<212> TYPE: DNA
<213> ORGANISM: Vulcanisaeta moutnovskia

<400> SEQUENCE: 124
atggcggtgc gtattagcat tgccggtggt aatgaaattg atccgggtag catgggtctg    60
accctgtttc atgaacatct gcgtctgatt accgaagttg ttcgttggaa ttggcctcat   120
ctgtataacg aagatgaaga attgaaacgt gcaattgatg cagttaacgc agccaaaaaa   180
tacggcgtga aaaccattat tgatctgacc gttgcaggta ttggttgtga tgttcgcttt   240
aatgaaaaag ttgcaaaagc caccggtgtg aacattatta tgggcaccgg tttttatacc   300
tataccgaaa tcccgttcta tttcaaaaac cgtggtattg atagcctggt tgatgccttt   360
gttcatgata ttaccattgg tattcagggc accaataccc gtgcagcatt tgttaaagca   420
gtgattgata gcagcggtct gaccaaagat gttgaaatgg caattcgtgc agcagcaaaa   480
gcacatatca aaaccgatgt tccgattatc acccatagct tgttggtaa taaaagcagc   540 ctggatctga tccgcatttt caagaagaa ggcgttgatc tggcacgtac cgttattggt   600
catgttggtg ataccgatga tatcagcttt attgagcaga ttctgcgtga aggtgcattt   660
attggtctgg atcgttttgg cctggatatt tatctgccgc tggataaacg tgttaaaacc   720
gcaattgaac tgattaaacg cggttggatt gatcagctgc tgctgagcca tgattattgt   780
ccgaccattg attggtatcc gcctgaagtt gtgcgtagca ccaccccgga ttggaccatg   840
accctgattt gagaaaagt tattccgcgt atgcgtagcg aaggtattac ggaagaacaa   900
attaatcgcg tgctgattga taatccgcgt cgtctgttta ccggtcgtta a            951

<210> SEQ ID NO 125
<211> LENGTH: 316
<212> TYPE: PRT
<213> ORGANISM: Vulcanisaeta moutnovskia

<400> SEQUENCE: 125

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Ser Trp Tyr Pro Pro Gly Val Val Arg
            260                 265                 270

Ser Thr Thr Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
    290                 295                 300

Leu Ile Asp Asn Pro Arg Arg Leu Phe Thr Gly Arg
305                 310                 315

<210> SEQ ID NO 126
<211> LENGTH: 951
<212> TYPE: DNA
<213> ORGANISM: Vulcanisaeta moutnovskia

<400> SEQUENCE: 126
atggcggtgc gtattagcat tgccggtggt aatgaaattg atccgggtag catgggtctg    60

-continued

```
accctgtttc atgaacatct gcgtctgatt accgaagttg ttcgttggaa ttggcctcat    120
ctgtataacg aagatgaaga attgaaacgt gcaattgatg cagttaacgc agccaaaaaa    180
tacggcgtga aaaccattat tgatctgacc gttgcaggta ttggttgtga tgttcgcttt    240
aatgaaaaag ttgcaaaagc caccggtgtg aacattata tgggcaccgg tttttatacc    300
tataccgaaa tcccgttcta tttcaaaaac cgtggtattg atagcctggt tgatgccttt    360
gttcatgata ttaccattgg tattcagggc accaataccc gtgcagcatt tgttaaagca    420
gtgattgata gcagcggtct gaccaaagat gttgaaatgg caattcgtgc agcagcaaaa    480
gcacatatca aaaccgatgt tccgattatc ccccatagct tgttggtaa taaaagcagc    540
ctggatctga tccgcatttt caaagaagaa ggcgttgatc tggcacgtac cgttattggt    600
catgttggtg ataccgatga tatcagcttt attgagcaga ttctgcgtga aggtgcattt    660
attggtctgg atcgttttgg cctggatatt tatctgccgc tggataaacg tgttaaaacc    720
gctattgaac tgattaaacg cggttggatt gatcagctgc tgctgagcca tgattattgt    780
ccgaccattg attggtatcc gcctgaagtt gtgcgtagcc cggttccgga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a              951
```

<210> SEQ ID NO 127
<211> LENGTH: 316
<212> TYPE: PRT
<213> ORGANISM: Vulcanisaeta moutnovskia

<400> SEQUENCE: 127

```
Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Asp Ile
        195                 200                 205

Ser Phe Ile Glu Gln Ile Leu Arg Glu Gly Ala Phe Ile Gly Leu Asp
    210                 215                 220
```

```
Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270

Ser Pro Val Pro Asp Trp Thr Met Thr Leu Ile Phe Glu Lys Val Ile
        275                 280                 285

Pro Arg Met Arg Ser Glu Gly Ile Thr Glu Glu Gln Ile Asn Arg Val
290                 295                 300

Leu Ile Asp Asn Pro Arg Arg Leu Phe Thr Gly Arg
305                 310                 315

<210> SEQ ID NO 128
<211> LENGTH: 951
<212> TYPE: DNA
<213> ORGANISM: Vulcanisaeta moutnovskia

<400> SEQUENCE: 128
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180
tacggcgtga aaccattat tgatctgacc gttgcaggta ttggttgtga tgttcgcttt     240
aatgaaaaag ttgcaaaagc caccggtgtg aacattatta tgggcaccgg tttttatacc     300
tataccgaaa tcccgttcta tttcaaaaac cgtggtattg atagcctggt tgatgccttt     360
attcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc     540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatg tatccgccgc tggataaacg tgttaaaacc     720
gcaattgaac tgattaaacg cggttggatt gatcagctgc tgctgagcca tgattattgt     780
ccgaccattg attggtatcc gcctgaagtt gtgcgtagca ccgttccgga ttggaccatg     840
accctgattt ttgagaaagt tattccgcgt atgcgtagcg aaggtattag cgaagaacaa     900
attaatcgcg tgctgattga taatccgcgt cgtctgttta ccggtcgtta a              951

<210> SEQ ID NO 129
<211> LENGTH: 316
<212> TYPE: PRT
<213> ORGANISM: Vulcanisaeta moutnovskia

<400> SEQUENCE: 129

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60
```

| Thr | Ile | Ile | Asp | Leu | Thr | Val | Ala | Gly | Ile | Gly | Cys | Asp | Val | Arg | Phe |
| 65 | | | | 70 | | | | | 75 | | | | | 80 | |

| Asn | Glu | Lys | Val | Ala | Lys | Ala | Thr | Gly | Val | Asn | Ile | Ile | Met | Gly | Thr |
| | | | | 85 | | | | | 90 | | | | | 95 | |

| Gly | Phe | Tyr | Thr | Tyr | Thr | Glu | Ile | Pro | Phe | Tyr | Phe | Lys | Asn | Arg | Gly |
| | | | 100 | | | | | 105 | | | | | 110 | | |

| Ile | Asp | Ser | Leu | Val | Asp | Ala | Phe | Ile | His | Asp | Ile | Thr | Ile | Gly | Ile |
| | | 115 | | | | | 120 | | | | | 125 | | | |

| Gln | Gly | Thr | Asn | Thr | Arg | Ala | Ala | Phe | Val | Lys | Ala | Val | Ile | Asp | Ser |
| | 130 | | | | | 135 | | | | | 140 | | | | |

| Ser | Gly | Leu | Thr | Lys | Asp | Val | Glu | Met | Ala | Ile | Arg | Ala | Ala | Lys |
| 145 | | | | 150 | | | | | 155 | | | | | 160 |

| Ala | His | Ile | Lys | Thr | Asp | Val | Pro | Ile | Ile | Thr | His | Ser | Phe | Val | Gly |
| | | | | 165 | | | | | 170 | | | | | 175 | |

| Asn | Lys | Ser | Ser | Leu | Asp | Leu | Ile | Arg | Ile | Phe | Lys | Glu | Glu | Gly | Val |
| | | | 180 | | | | | 185 | | | | | 190 | | |

| Asp | Leu | Ala | Arg | Thr | Val | Ile | Gly | His | Val | Gly | Asp | Thr | Asp | Asp | Ile |
| | | | 195 | | | | | 200 | | | | | 205 | | |

| Ser | Phe | Ile | Glu | Gln | Ile | Leu | Arg | Glu | Gly | Ala | Phe | Ile | Gly | Leu | Asp |
| 210 | | | | | 215 | | | | | 220 | | | | | |

| Arg | Phe | Gly | Leu | Asp | Ile | Tyr | Pro | Pro | Leu | Asp | Lys | Arg | Val | Lys | Thr |
| 225 | | | | 230 | | | | | 235 | | | | | 240 | |

| Ala | Ile | Glu | Leu | Ile | Lys | Arg | Gly | Trp | Ile | Asp | Gln | Leu | Leu | Ser |
| | | | | 245 | | | | | 250 | | | | | 255 |

| His | Asp | Tyr | Cys | Pro | Thr | Ile | Asp | Trp | Tyr | Pro | Pro | Glu | Val | Val | Arg |
| | | | 260 | | | | | 265 | | | | | 270 | | |

| Ser | Thr | Val | Pro | Asp | Trp | Thr | Met | Thr | Leu | Ile | Phe | Glu | Lys | Val | Ile |
| | | 275 | | | | | 280 | | | | | 285 | | | |

| Pro | Arg | Met | Arg | Ser | Glu | Gly | Ile | Ser | Glu | Glu | Gln | Ile | Asn | Arg | Val |
| | 290 | | | | | 295 | | | | | 300 | | | | |

| Leu | Ile | Asp | Asn | Pro | Arg | Arg | Leu | Phe | Thr | Gly | Arg |
| 305 | | | | 310 | | | | | 315 | | |

<210> SEQ ID NO 130
<211> LENGTH: 951
<212> TYPE: DNA
<213> ORGANISM: Vulcanisaeta moutnovskia

<400> SEQUENCE: 130

```
atggcggtgc gtattagcat tgccggtggt aatgaaattg atccgggtag catgggtctg     60
accctgtttc atgaacatct gcgtctgatt accgaagttg ttcgttggaa ttggcctcat    120
ctgtataacg aagatgaaga attgaaacgt gcaattgatg cagttaacgc agccaaaaaa    180
tacggcgtga aaaccattat tgatctgacc gttgcaggta ttggttgtga tgttcgcttt    240
aatgaaaaag ttgcaaaagc caccggtgtg aacattatta tgggcaccgg tttttatacc    300
tataccgaaa tcccgttcta tttcaaaaac cgtggtattg atagcctggt tgatgccttt    360
attcatgata ttaccattgg tattcagggc accaataccc gtgcagcatt tgttaaagca    420
gtgattgata gcagcggtct gaccaaagat gttgaaatgg caattcgtgc agcagcaaaa    480
gcacatatca aaccgatgt tccgattatc acccatagct tgttggtaa taaaagcagc    540
ctggatctga tccgcatttt caaagaagaa ggcgttgatc tggcacgtac cgttattggt    600
catgttggtg atacagatga tatcagcttt attgagcaga ttctgcgtga aggtgcattt    660
attggtctag atcgttttgg cctggatatt tatctgccgc tggataaacg tgttaaaacc    720
```

```
gcaattgaac tgattaaacg cggttggatt gatcagctgc tgctgagcca tgattattgt    780
ccgaccattg attggtatcc gcctgaagtt gtgcgtagca ccgttcctga ttggaccatg    840
accctgattt ttgagaaagt tattccgcgt atgcgtagcg aaggtattac ggaagaacaa    900
attaatcgcg tgctgattga taatccgcgt cgtctgttta ccggtcgtta a             951

<210> SEQ ID NO 131
<211> LENGTH: 316
<212> TYPE: PRT
<213> ORGANISM: Vulcanisaeta moutnovskia

<400> SEQUENCE: 131

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Tyr Thr Tyr Thr Glu Ile Pro Phe Tyr Phe Lys Asn Arg Gly
            100                 105                 110

Ile Asp Ser Leu Val Asp Ala Phe Ile His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Ile
        195                 200                 205

Ser Phe Ile Glu Gln Ile Leu Arg Glu Gly Ala Phe Ile Gly Leu Asp
    210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Trp Tyr Pro Pro Glu Val Val Arg
            260                 265                 270

Ser Thr Val Pro Asp Trp Thr Met Thr Leu Ile Phe Glu Lys Val Ile
        275                 280                 285

Pro Arg Met Arg Ser Glu Gly Ile Thr Glu Gln Ile Asn Arg Val
    290                 295                 300

Leu Ile Asp Asn Pro Arg Arg Leu Phe Thr Gly Arg
305                 310                 315

<210> SEQ ID NO 132
```

```
<211> LENGTH: 951
<212> TYPE: DNA
<213> ORGANISM: Vulcanisaeta moutnovskia

<400> SEQUENCE: 132
atggcggtgc gtattagcat tgccggtggt aatgaaattg atccgggtag catgggtctg      60
accctgtttc atgaacatct gcgtctgatt accgaagttg ttcgttggaa ttggcctcat     120
ctgtataacg aagatgaaga attgaaacgt gcaattgatg cagttaacgc agccaaaaaa     180
tacggcgtga aaaccattat tgatctgacc gttgcaggta ttggttgtga tgttcgcttt     240
aatgaaaaag ttgcaaaagc caccggtgtg aacattatta tgggcaccgg tttttggacc     300
tataccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc      540
ctggatctga tccgcatttt caaagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg attggtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a             951

<210> SEQ ID NO 133
<211> LENGTH: 316
<212> TYPE: PRT
<213> ORGANISM: Vulcanisaeta moutnovskia

<400> SEQUENCE: 133

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Leu Ile Thr Glu
            20                  25                  30

Val Val Arg Trp Asn Trp Pro His Leu Tyr Asn Glu Asp Glu Glu Leu
        35                  40                  45

Lys Arg Ala Ile Asp Ala Val Asn Ala Ala Lys Lys Tyr Gly Val Lys
    50                  55                  60

Thr Ile Ile Asp Leu Thr Val Ala Gly Ile Gly Cys Asp Val Arg Phe
65                  70                  75                  80

Asn Glu Lys Val Ala Lys Ala Thr Gly Val Asn Ile Ile Met Gly Thr
                85                  90                  95

Gly Phe Trp Thr Tyr Thr Glu Ile Pro Phe Tyr Phe Lys Asn Arg Gly
            100                 105                 110

Ile Asp Ser Leu Val Asp Ala Phe Val His Asp Ile Thr Ile Gly Ile
        115                 120                 125

Gln Gly Thr Asn Thr Arg Ala Ala Phe Val Lys Ala Val Ile Asp Ser
    130                 135                 140

Ser Gly Leu Thr Lys Asp Val Glu Met Ala Ile Arg Ala Ala Lys
145                 150                 155                 160

Ala His Ile Lys Thr Asp Val Pro Ile Ile Thr His Ser Phe Val Gly
                165                 170                 175
```

Asn Lys Ser Ser Leu Asp Leu Ile Arg Ile Phe Lys Glu Glu Gly Val
            180                 185                 190

Asp Leu Ala Arg Thr Val Ile Gly His Val Gly Asp Thr Asp Ile
            195                 200                 205

Ser Phe Ile Glu Gln Ile Leu Arg Glu Gly Ala Phe Ile Gly Leu Asp
            210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Ser
            245                 250                 255

His Asp Tyr Cys Pro Thr Ile Asp Trp Tyr Pro Pro Glu Val Val Arg
            260                 265                 270

Ser Thr Val Pro Asp Trp Thr Met Thr Leu Ile Phe Glu Lys Val Ile
            275                 280                 285

Pro Arg Met Arg Ser Glu Gly Ile Thr Glu Glu Gln Ile Asn Arg Val
            290                 295                 300

Leu Ile Asp Asn Pro Arg Arg Leu Phe Thr Gly Arg
305                 310                 315

<210> SEQ ID NO 134
<211> LENGTH: 951
<212> TYPE: DNA
<213> ORGANISM: Vulcanisaeta moutnovskia

<400> SEQUENCE: 134

```
atggcggtgc gtattagcat tgccggtggt aatgaaattg atccgggtag catgggtctg      60
accctgtttc atgaacatct gcgtgcaatt accgaagttg ttcgttggaa ttggcctcat     120
ctgtataacg aagatgaaga attgaaacgt gcaattgatg cagttaacgc agccaaaaaa     180
tacggcgtga aaaccattat tgatctgacc gttgcaggta ttggttgtga tgttcgcttt     240
aatgaaaaag ttgcaaaagc caccggtgtg aacattatta tgggcaccgg tttttatacc     300
tttaccgaaa tcccgttcta tttcaaaaac cgtggtattg atagcctggt tgatgccttt     360
gttcatgata ttaccattgg tattcagggc accaataccc gtgcagcatt tgttaaagca     420
gtgattgata gcagcggtct gaccaaagat gttgaaatgg caattcgtgc agcagcaaaa     480
gcacatatca aaaccgatgt tccgattatc acccatagct tgttggtaa taaaagcagc     540
ctggatctga tccgcatttt caagaagaa ggcgttgatc tggcacgtac cgttattggt     600
catgttggtg ataccgatga tatcagcttt attgagcaga ttctgcgtga aggtgcattt     660
attggtctgg atcgttttgg cctggatatt tatctgccgc tggataaacg tgttaaaacc     720
gcaattgaac tgattaaacg cggttggatt gatcagctgc tgctgagcca tgattattgt     780
ccgaccattg atctgtatcc gcctgaagtt gtgcgtagca ccgttccgga ttggaccatg     840
accctgattt ttgagaaagt tattccgcgt atgcgtagcg aaggtattac ggaagaacaa     900
attaatcgcg tgctgattga taatccgcgt cgtctgttta ccggtcgtta a            951
```

<210> SEQ ID NO 135
<211> LENGTH: 316
<212> TYPE: PRT
<213> ORGANISM: Vulcanisaeta moutnovskia

<400> SEQUENCE: 135

Met Ala Val Arg Ile Ser Ile Ala Gly Gly Asn Glu Ile Asp Pro Gly
1               5                   10                  15

Ser Met Gly Leu Thr Leu Phe His Glu His Leu Arg Ala Ile Thr Glu

```
            20                  25                  30
Val Val Arg Trp Asn Trp Pro His Leu Tyr Asn Glu Asp Glu Leu
        35                  40                  45

Lys Arg Ala Ile Asp Ala Val Asn Ala Ala Lys Lys Tyr Gly Val Lys
 50                  55                  60

Thr Ile Ile Asp Leu Thr Val Ala Gly Ile Gly Cys Asp Val Arg Phe
 65                  70                  75                  80

Asn Glu Lys Val Ala Lys Ala Thr Gly Val Asn Ile Ile Met Gly Thr
                 85                  90                  95

Gly Phe Tyr Thr Phe Thr Glu Ile Pro Phe Tyr Phe Lys Asn Arg Gly
                100                 105                 110

Ile Asp Ser Leu Val Asp Ala Phe Val His Asp Ile Thr Ile Gly Ile
                115                 120                 125

Gln Gly Thr Asn Thr Arg Ala Ala Phe Val Lys Ala Val Ile Asp Ser
            130                 135                 140

Ser Gly Leu Thr Lys Asp Val Glu Met Ala Ile Arg Ala Ala Ala Lys
145                 150                 155                 160

Ala His Ile Lys Thr Asp Val Pro Ile Ile Thr His Ser Phe Val Gly
                165                 170                 175

Asn Lys Ser Ser Leu Asp Leu Ile Arg Ile Phe Lys Glu Glu Gly Val
                180                 185                 190

Asp Leu Ala Arg Thr Val Ile Gly His Val Gly Asp Thr Asp Asp Ile
                195                 200                 205

Ser Phe Ile Glu Gln Ile Leu Arg Glu Gly Ala Phe Ile Gly Leu Asp
        210                 215                 220

Arg Phe Gly Leu Asp Ile Tyr Leu Pro Leu Asp Lys Arg Val Lys Thr
225                 230                 235                 240

Ala Ile Glu Leu Ile Lys Arg Gly Trp Ile Asp Gln Leu Leu Leu Ser
                245                 250                 255

His Asp Tyr Cys Pro Thr Ile Asp Leu Tyr Pro Pro Glu Val Val Arg
                260                 265                 270

Ser Thr Val Pro Asp Trp Thr Met Thr Leu Ile Phe Glu Lys Val Ile
                275                 280                 285

Pro Arg Met Arg Ser Glu Gly Ile Thr Glu Glu Gln Ile Asn Arg Val
                290                 295                 300

Leu Ile Asp Asn Pro Arg Arg Leu Phe Thr Gly Arg
305                 310                 315

<210> SEQ ID NO 136
<211> LENGTH: 37
<212> TYPE: DNA
<213> ORGANISM: Artificial Sequence
<220> FEATURE:
<223> OTHER INFORMATION: G9E - F

<400> SEQUENCE: 136
gtattagcat tgccggtgaa aatgaaattg atccggg                              37

<210> SEQ ID NO 137
<211> LENGTH: 37
<212> TYPE: DNA
<213> ORGANISM: Artificial Sequence
<220> FEATURE:
<223> OTHER INFORMATION: G9E - R

<400> SEQUENCE: 137
cccggatcaa tttcattttc accggcaatg ctaatac                              37
```

<210> SEQ ID NO 138
<211> LENGTH: 39
<212> TYPE: DNA
<213> ORGANISM: Artificial Sequence
<220> FEATURE:
<223> OTHER INFORMATION: L28A - F

<400> SEQUENCE: 138
gtttcatgaa catctgcgtg cgattaccga agttgttcg                      39

<210> SEQ ID NO 139
<211> LENGTH: 39
<212> TYPE: DNA
<213> ORGANISM: Artificial Sequence
<220> FEATURE:
<223> OTHER INFORMATION: L28A - R

<400> SEQUENCE: 139
cgaacaactt cggtaatcgc acgcagatgt tcatgaaac                      39

<210> SEQ ID NO 140
<211> LENGTH: 37
<212> TYPE: DNA
<213> ORGANISM: Artificial Sequence
<220> FEATURE:
<223> OTHER INFORMATION: L68V - F

<400> SEQUENCE: 140
gtgaaaacca ttattgatgt gaccgttgca ggtattg                        37

<210> SEQ ID NO 141
<211> LENGTH: 37
<212> TYPE: DNA
<213> ORGANISM: Artificial Sequence
<220> FEATURE:
<223> OTHER INFORMATION: L68V - R

<400> SEQUENCE: 141
caatacctgc aacggtcaca tcaataatgg ttttcac                        37

<210> SEQ ID NO 142
<211> LENGTH: 31
<212> TYPE: DNA
<213> ORGANISM: Artificial Sequence
<220> FEATURE:
<223> OTHER INFORMATION: T69S - F

<400> SEQUENCE: 142
ccattattga tctgagcgtt gcaggtattg g                              31

<210> SEQ ID NO 143
<211> LENGTH: 31
<212> TYPE: DNA
<213> ORGANISM: Artificial Sequence
<220> FEATURE:
<223> OTHER INFORMATION: T69S - R

<400> SEQUENCE: 143
ccaatacctg caacgctcag atcaataatg g                              31

<210> SEQ ID NO 144
<211> LENGTH: 44
<212> TYPE: DNA
<213> ORGANISM: Artificial Sequence
<220> FEATURE:

<223> OTHER INFORMATION: V77T - F

<400> SEQUENCE: 144
gttgcaggta ttggttgtga tacccgcttt aatgaaaaag ttgc    44

<210> SEQ ID NO 145
<211> LENGTH: 44
<212> TYPE: DNA
<213> ORGANISM: Artificial Sequence
<220> FEATURE:
<223> OTHER INFORMATION: V77T - R

<400> SEQUENCE: 145 gcaactttt cattaaagcg ggtatcacaa ccaatacctg caac    44

<210> SEQ ID NO 146
<211> LENGTH: 31
<212> TYPE: DNA
<213> ORGANISM: Artificial Sequence
<220> FEATURE:
<223> OTHER INFORMATION: Y98W - F

<400> SEQUENCE: 146
gggcaccggt ttttggacct ataccgaaat c    31

<210> SEQ ID NO 147
<211> LENGTH: 31
<212> TYPE: DNA
<213> ORGANISM: Artificial Sequence
<220> FEATURE:
<223> OTHER INFORMATION: Y98W - R

<400> SEQUENCE: 147
gatttcggta taggtccaaa aaccggtgcc c    31

<210> SEQ ID NO 148
<211> LENGTH: 32
<212> TYPE: DNA
<213> ORGANISM: Artificial Sequence
<220> FEATURE:
<223> OTHER INFORMATION: Y100F - F

<400> SEQUENCE: 148 ccggtttta tacctttacc gaaatcccgt tc    32

<210> SEQ ID NO 149
<211> LENGTH: 32
<212> TYPE: DNA
<213> ORGANISM: Artificial Sequence
<220> FEATURE:
<223> OTHER INFORMATION: Y100F - R

<400> SEQUENCE: 149
gaacgggatt tcggtaaagg tataaaaacc gg    32

<210> SEQ ID NO 150
<211> LENGTH: 37
<212> TYPE: DNA
<213> ORGANISM: Artificial Sequence
<220> FEATURE:
<223> OTHER INFORMATION: V120I - F

<400> SEQUENCE: 150
gcctggttga tgcctttatt catgatatta ccattgg    37

<210> SEQ ID NO 151
<211> LENGTH: 37
<212> TYPE: DNA
<213> ORGANISM: Artificial Sequence
<220> FEATURE:
<223> OTHER INFORMATION: V120I - R

<400> SEQUENCE: 151
ccaatggtaa tatcatgaat aaaggcatca accaggc                             37

<210> SEQ ID NO 152
<211> LENGTH: 39
<212> TYPE: DNA
<213> ORGANISM: Artificial Sequence
<220> FEATURE:
<223> OTHER INFORMATION: I123L - F

<400> SEQUENCE: 152
gatgcctttg ttcatgatct gaccattggt attcagggc                           39

<210> SEQ ID NO 153
<211> LENGTH: 39
<212> TYPE: DNA
<213> ORGANISM: Artificial Sequence
<220> FEATURE:
<223> OTHER INFORMATION: I123L - R

<400> SEQUENCE: 153
gccctgaata ccaatggtca gatcatgaac aaaggcatc                           39

<210> SEQ ID NO 154
<211> LENGTH: 38
<212> TYPE: DNA
<213> ORGANISM: Artificial Sequence
<220> FEATURE:
<223> OTHER INFORMATION: N131P - F

<400> SEQUENCE: 154
cattggtatt cagggcaccc cgacccgtgc agcatttg                            38

<210> SEQ ID NO 155
<211> LENGTH: 38
<212> TYPE: DNA
<213> ORGANISM: Artificial Sequence
<220> FEATURE:
<223> OTHER INFORMATION: N131P - R

<400> SEQUENCE: 155
caaatgctgc acgggtcggg gtgccctgaa taccaatg                            38

<210> SEQ ID NO 156
<211> LENGTH: 34
<212> TYPE: DNA
<213> ORGANISM: Artificial Sequence
<220> FEATURE:
<223> OTHER INFORMATION: D165N - F

<400> SEQUENCE: 156
gcacatatca aaaccaatgt tccgattatc accc                                34

<210> SEQ ID NO 157
<211> LENGTH: 34
<212> TYPE: DNA
<213> ORGANISM: Artificial Sequence
<220> FEATURE:
<223> OTHER INFORMATION: D165N - R

<400> SEQUENCE: 157
gggtgataat cggaacattg gttttgatat gtgc                               34

<210> SEQ ID NO 158
<211> LENGTH: 31
<212> TYPE: DNA
<213> ORGANISM: Artificial Sequence
<220> FEATURE:
<223> OTHER INFORMATION: L227V - F

<400> SEQUENCE: 158
ctggatcgtt ttggcgtgga tatttatctg c                                  31

<210> SEQ ID NO 159
<211> LENGTH: 31
<212> TYPE: DNA
<213> ORGANISM: Artificial Sequence
<220> FEATURE:
<223> OTHER INFORMATION: L227V - R

<400> SEQUENCE: 159
gcagataaat atccacgcca aaacgatcca g                                  31

<210> SEQ ID NO 160
<211> LENGTH: 40
<212> TYPE: DNA
<213> ORGANISM: Artificial Sequence
<220> FEATURE:
<223> OTHER INFORMATION: I229M - F

<400> SEQUENCE: 160
gatcgttttg gcctggatat gtatctgccg ctggataaac                         40

<210> SEQ ID NO 161
<211> LENGTH: 40
<212> TYPE: DNA
<213> ORGANISM: Artificial Sequence
<220> FEATURE:
<223> OTHER INFORMATION: I229M - R

<400> SEQUENCE: 161
gtttatccag cggcagatac atatccaggc caaaacgatc                         40

<210> SEQ ID NO 162
<211> LENGTH: 36
<212> TYPE: DNA
<213> ORGANISM: Artificial Sequence
<220> FEATURE:
<223> OTHER INFORMATION: Y230S - F

<400> SEQUENCE: 162
gttttggcct ggatattagc ctgccgctgg ataaac                             36

<210> SEQ ID NO 163
<211> LENGTH: 36
<212> TYPE: DNA
<213> ORGANISM: Artificial Sequence
<220> FEATURE:
<223> OTHER INFORMATION: Y230S - R

<400> SEQUENCE: 163
gtttatccag cggcaggcta atatccaggc caaaac                             36

<210> SEQ ID NO 164
<211> LENGTH: 30

```
<212> TYPE: DNA
<213> ORGANISM: Artificial Sequence
<220> FEATURE:
<223> OTHER INFORMATION: L231P - F

<400> SEQUENCE: 164
cctggatatt tatccgccgc tggataaacg                                      30

<210> SEQ ID NO 165
<211> LENGTH: 30
<212> TYPE: DNA
<213> ORGANISM: Artificial Sequence
<220> FEATURE:
<223> OTHER INFORMATION: L231P - R

<400> SEQUENCE: 165
cgtttatcca gcggcggata aatatccagg                                      30

<210> SEQ ID NO 166
<211> LENGTH: 40
<212> TYPE: DNA
<213> ORGANISM: Artificial Sequence
<220> FEATURE:
<223> OTHER INFORMATION: C259A - F

<400> SEQUENCE: 166
ctgctgagcc atgattatgc gccgaccatt gattggtatc                           40

<210> SEQ ID NO 167
<211> LENGTH: 40
<212> TYPE: DNA
<213> ORGANISM: Artificial Sequence
<220> FEATURE:
<223> OTHER INFORMATION: C259A - R

<400> SEQUENCE: 167
gataccaatc aatggtcggc gcataatcat ggctcagcag                           40

<210> SEQ ID NO 168
<211> LENGTH: 40
<212> TYPE: DNA
<213> ORGANISM: Artificial Sequence
<220> FEATURE:
<223> OTHER INFORMATION: C259L - F

<400> SEQUENCE: 168
ctgctgagcc atgattatct gccgaccatt gattggtatc                           40

<210> SEQ ID NO 169
<211> LENGTH: 40
<212> TYPE: DNA
<213> ORGANISM: Artificial Sequence
<220> FEATURE:
<223> OTHER INFORMATION: C259L - R

<400> SEQUENCE: 169
gataccaatc aatggtcggc agataatcat ggctcagcag                           40

<210> SEQ ID NO 170
<211> LENGTH: 31
<212> TYPE: DNA
<213> ORGANISM: Artificial Sequence
<220> FEATURE:
<223> OTHER INFORMATION: I262F - F

<400> SEQUENCE: 170
```
gattattgtc cgacctttga ttggtatccg c                                    31

<210> SEQ ID NO 171
<211> LENGTH: 31
<212> TYPE: DNA
<213> ORGANISM: Artificial Sequence
<220> FEATURE:
<223> OTHER INFORMATION: I262F - R

<400> SEQUENCE: 171
gcggatacca atcaaaggtc ggacaataat c                                    31

<210> SEQ ID NO 172
<211> LENGTH: 43
<212> TYPE: DNA
<213> ORGANISM: Artificial Sequence
<220> FEATURE:
<223> OTHER INFORMATION: W264L - F

<400> SEQUENCE: 172
gattattgtc cgaccattga tctgtatccg cctgaagttg tgc                       43

<210> SEQ ID NO 173
<211> LENGTH: 43
<212> TYPE: DNA
<213> ORGANISM: Artificial Sequence
<220> FEATURE:
<223> OTHER INFORMATION: W264L - R

<400> SEQUENCE: 173
gcacaacttc aggcggatac agatcaatgg tcggacaata atc                       43

<210> SEQ ID NO 174
<211> LENGTH: 43
<212> TYPE: DNA
<213> ORGANISM: Artificial Sequence
<220> FEATURE:
<223> OTHER INFORMATION: W264M - F

<400> SEQUENCE: 174
gattattgtc cgaccattga tatgtatccg cctgaagttg tgc                       43

<210> SEQ ID NO 175
<211> LENGTH: 43
<212> TYPE: DNA
<213> ORGANISM: Artificial Sequence
<220> FEATURE:
<223> OTHER INFORMATION: W264M - R

<400> SEQUENCE: 175
gcacaacttc aggcggatac atatcaatgg tcggacaata atc                       43

<210> SEQ ID NO 176
<211> LENGTH: 28
<212> TYPE: DNA
<213> ORGANISM: Artificial Sequence
<220> FEATURE:
<223> OTHER INFORMATION: W264C - F

<400> SEQUENCE: 176
ccgaccattg attgctatcc gcctgaag                                        28

<210> SEQ ID NO 177
<211> LENGTH: 28
<212> TYPE: DNA
<213> ORGANISM: Artificial Sequence

<220> FEATURE:
<223> OTHER INFORMATION: W264C - R

<400> SEQUENCE: 177
cttcaggcgg atagcaatca atggtcgg                                      28

<210> SEQ ID NO 178
<211> LENGTH: 35
<212> TYPE: DNA
<213> ORGANISM: Artificial Sequence
<220> FEATURE:
<223> OTHER INFORMATION: W264F - F

<400> SEQUENCE: 178
ccgaccattg atttttatcc gcctgaagtt gtgcg                              35

<210> SEQ ID NO 179
<211> LENGTH: 35
<212> TYPE: DNA
<213> ORGANISM: Artificial Sequence
<220> FEATURE:
<223> OTHER INFORMATION: W264F - R

<400> SEQUENCE: 179
cgcacaactt caggcggata aaaatcaatg gtcgg                              35

<210> SEQ ID NO 180
<211> LENGTH: 30
<212> TYPE: DNA
<213> ORGANISM: Artificial Sequence
<220> FEATURE:
<223> OTHER INFORMATION: W264A - F

<400> SEQUENCE: 180
gtccgaccat tgatgcgtat ccgcctgaag                                    30

<210> SEQ ID NO 181
<211> LENGTH: 30
<212> TYPE: DNA
<213> ORGANISM: Artificial Sequence
<220> FEATURE:
<223> OTHER INFORMATION: W264A - R

<400> SEQUENCE: 181
cttcaggcgg atacgcatca atggtcggac                                    30

<210> SEQ ID NO 182
<211> LENGTH: 32
<212> TYPE: DNA
<213> ORGANISM: Artificial Sequence
<220> FEATURE:
<223> OTHER INFORMATION: T273P - F

<400> SEQUENCE: 182
gaagttgtgc gtagcccggt tccggattgg ac                                 32

<210> SEQ ID NO 183
<211> LENGTH: 32
<212> TYPE: DNA
<213> ORGANISM: Artificial Sequence
<220> FEATURE:
<223> OTHER INFORMATION: T273P - R

<400> SEQUENCE: 183
gtccaatccg gaaccgggct acgcacaact tc                                 32

<210> SEQ ID NO 184
<211> LENGTH: 38
<212> TYPE: DNA
<213> ORGANISM: Artificial Sequence
<220> FEATURE:
<223> OTHER INFORMATION: V274T - F

<400> SEQUENCE: 184
gaagttgtgc gtagcaccac cccggattgg accatgac         38

<210> SEQ ID NO 185
<211> LENGTH: 38
<212> TYPE: DNA
<213> ORGANISM: Artificial Sequence
<220> FEATURE:
<223> OTHER INFORMATION: V274T - R

<400> SEQUENCE: 185
gtcatggtcc aatccggggt ggtgctacgc acaacttc         38

<210> SEQ ID NO 186
<211> LENGTH: 33
<212> TYPE: DNA
<213> ORGANISM: Artificial Sequence
<220> FEATURE:
<223> OTHER INFORMATION: M279T - F

<400> SEQUENCE: 186
gttccggatt ggaccaccac cctgattttt gag         33

<210> SEQ ID NO 187
<211> LENGTH: 33
<212> TYPE: DNA
<213> ORGANISM: Artificial Sequence
<220> FEATURE:
<223> OTHER INFORMATION: M279T - R

<400> SEQUENCE: 187
ctcaaaaatc agggtggtgg tccaatccgg aac         33

<210> SEQ ID NO 188
<211> LENGTH: 30
<212> TYPE: DNA
<213> ORGANISM: Artificial Sequence
<220> FEATURE:
<223> OTHER INFORMATION: L281M - F

<400> SEQUENCE: 188
ccggattgga ccatgaccat gatttttgag         30

<210> SEQ ID NO 189
<211> LENGTH: 30
<212> TYPE: DNA
<213> ORGANISM: Artificial Sequence
<220> FEATURE:
<223> OTHER INFORMATION: L281M - R

<400> SEQUENCE: 189
ctcaaaaatc atggtcatgg tccaatccgg         30

<210> SEQ ID NO 190
<211> LENGTH: 37
<212> TYPE: DNA
<213> ORGANISM: Artificial Sequence
<220> FEATURE:
<223> OTHER INFORMATION: T296S - F

<400> SEQUENCE: 190
gcgtagcgaa ggtattagcg aagaacaaat taatcgc   37

<210> SEQ ID NO 191
<211> LENGTH: 37
<212> TYPE: DNA
<213> ORGANISM: Artificial Sequence
<220> FEATURE:
<223> OTHER INFORMATION: T296S - R

<400> SEQUENCE: 191
gcgattaatt tgttcttcgc taataccttc gctacgc   37

<210> SEQ ID NO 192
<211> LENGTH: 315
<212> TYPE: PRT
<213> ORGANISM: Vulcanisaeta moutnovskia

<400> SEQUENCE: 192

```
Met Val Arg Ile Ser Ile Ala Gly Gly Asn Glu Ile Asp Pro Gly Ser
 1               5                  10                  15
Met Gly Leu Thr Leu Phe His Glu His Leu Arg Ala Ile Thr Glu Val
            20                  25                  30
Val Arg Trp Asn Trp Pro His Leu Tyr Asn Glu Asp Glu Leu Lys
        35                  40                  45
Arg Ala Ile Asp Ala Val Asn Ala Ala Lys Lys Tyr Gly Val Lys Thr
    50                  55                  60
Ile Ile Asp Leu Thr Val Ala Gly Ile Gly Cys Asp Val Arg Phe Asn
65                  70                  75                  80
Glu Lys Val Ala Lys Ala Thr Gly Val Asn Ile Ile Met Gly Thr Gly
                85                  90                  95
Phe Tyr Thr Tyr Thr Glu Ile Pro Phe Tyr Phe Lys Asn Arg Gly Ile
            100                 105                 110
Asp Ser Leu Val Asp Ala Phe Val His Asp Ile Thr Ile Gly Ile Gln
        115                 120                 125
Gly Thr Asn Thr Arg Ala Ala Phe Val Lys Ala Val Ile Asp Ser Ser
    130                 135                 140
Gly Leu Thr Lys Asp Val Glu Met Ala Ile Arg Ala Ala Lys Ala
145                 150                 155                 160
His Ile Lys Thr Asp Val Pro Ile Ile Thr His Ser Phe Val Gly Asn
                165                 170                 175
Lys Ser Ser Leu Asp Leu Ile Arg Ile Phe Lys Glu Glu Gly Val Asp
            180                 185                 190
Leu Ala Arg Thr Val Ile Gly His Val Gly Asp Thr Asp Asp Ile Ser
        195                 200                 205
Phe Ile Glu Gln Ile Leu Arg Glu Gly Ala Phe Ile Gly Leu Asp Arg
    210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Ser His
                245                 250                 255
Asp Tyr Cys Pro Thr Ile Asp Trp Tyr Pro Glu Val Val Arg Ser
            260                 265                 270
Thr Val Pro Asp Trp Thr Met Thr Leu Ile Phe Glu Lys Val Ile Pro
        275                 280                 285
```

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 193
<211> LENGTH: 315
<212> TYPE: PRT
<213> ORGANISM: Vulcanisaeta moutnovskia

<400> SEQUENCE: 193

Met Val Arg Ile Ser Ile Ala Gly Gly Asn Glu Ile Asp Pro Gly Ser
1               5                   10                  15

Met Gly Leu Thr Leu Phe His Glu His Leu Arg Gly Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Trp Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 194
<211> LENGTH: 315
<212> TYPE: PRT
<213> ORGANISM: Vulcanisaeta moutnovskia

<400> SEQUENCE: 194

Met Val Arg Ile Ser Ile Ala Gly Gly Asn Glu Ile Asp Pro Gly Ser
1               5                   10                  15

Met Gly Leu Thr Leu Phe His Glu His Leu Arg Val Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Trp Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 195
<211> LENGTH: 315
<212> TYPE: PRT
<213> ORGANISM: Vulcanisaeta moutnovskia

<400> SEQUENCE: 195

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

```
Arg Ala Ile Asp Ala Val Asn Ala Ala Lys Lys Tyr Gly Val Lys Thr
 50                  55                  60

Ile Ile Asp Leu Thr Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Tyr Thr Glu Thr Glu Ile Pro Phe Tyr Phe Lys Asn Arg Gly Ile
             100                 105                 110

Asp Ser Leu Val Asp Ala Phe Val His Asp Ile Thr Ile Gly Ile Gln
             115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
             180                 185                 190

Leu Ala Arg Thr Val Ile Gly His Val Gly Asp Thr Asp Asp Ile Ser
             195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Trp Tyr Pro Pro Glu Val Arg Ser
             260                 265                 270

Thr Val Pro Asp Trp Thr Met Thr Leu Ile Phe Glu Lys Val Ile Pro
             275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 196
<211> LENGTH: 315
<212> TYPE: PRT
<213> ORGANISM: Vulcanisaeta moutnovskia

<400> SEQUENCE: 196

Met Val Arg Ile Ser Ile Ala Gly Gly Asn Glu Ile Asp Pro Gly Ser
 1                   5                  10                  15

Met Gly Leu Thr Leu Phe His Glu His Leu Arg Leu Ile Thr Glu Val
                 20                  25                  30

Val Arg Trp Asn Trp Pro His Leu Tyr Asn Glu Asp Glu Glu Leu Lys
             35                  40                  45

Arg Ala Ile Asp Ala Val Asn Ala Ala Lys Lys Tyr Gly Val Lys Thr
 50                  55                  60

Ile Ile Asp Leu Thr Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Tyr Thr Tyr Thr Glu Ile Pro Phe Tyr Phe Lys Asn Arg Gly Ile
```

```
                    100                 105                 110
Asp Ser Leu Val Asp Ala Phe Val His Asp Ile Thr Ile Gly Ile Gln
            115                 120                 125
Gly Thr Asn Thr Arg Ala Ala Phe Val Lys Ala Val Ile Asp Ser Ser
        130                 135                 140
Gly Leu Thr Lys Asp Val Glu Met Ala Ile Arg Ala Ala Ala Lys Ala
145                 150                 155                 160
His Ile Lys Thr Asp Val Pro Ile Ile Thr His Ser Phe Val Gly Asn
                165                 170                 175
Lys Ser Ser Leu Asp Leu Ile Arg Ile Phe Lys Glu Glu Gly Val Asp
            180                 185                 190
Leu Ala Arg Thr Val Ile Gly His Val Gly Asp Thr Asp Asp Ile Ser
        195                 200                 205
Phe Ile Glu Gln Ile Leu Arg Glu Gly Ala Phe Ile Gly Leu Asp Gln
    210                 215                 220
Phe Gly Leu Asp Ile Tyr Leu Pro Leu Asp Lys Arg Val Lys Thr Ala
225                 230                 235                 240
Ile Glu Leu Ile Lys Arg Gly Trp Ile Asp Gln Leu Leu Ser His
                245                 250                 255
Asp Tyr Cys Pro Thr Ile Asp Trp Tyr Pro Pro Glu Val Val Arg Ser
            260                 265                 270
Thr Val Pro Asp Trp Thr Met Thr Leu Ile Phe Glu Lys Val Ile Pro
        275                 280                 285
Arg Met Arg Ser Glu Gly Ile Thr Glu Glu Gln Ile Asn Arg Val Leu
    290                 295                 300
Ile Asp Asn Pro Arg Arg Leu Phe Thr Gly Arg
305                 310                 315

<210> SEQ ID NO 197
<211> LENGTH: 315
<212> TYPE: PRT
<213> ORGANISM: Vulcanisaeta moutnovskia

<400> SEQUENCE: 197

Met Val Arg Ile Ser Ile Ala Gly Gly Asn Glu Ile Asp Pro Gly Ser
1               5                   10                  15
Met Gly Leu Thr Leu Phe His Glu His Leu Arg Leu Ile Thr Glu Val
            20                  25                  30
Val Arg Trp Asn Trp Pro His Leu Tyr Asn Glu Asp Glu Glu Leu Lys
        35                  40                  45
Arg Ala Ile Asp Ala Val Asn Ala Lys Lys Tyr Gly Val Lys Thr
    50                  55                  60
Ile Ile Asp Leu Thr Val Ala Gly Ile Gly Cys Asp Val Arg Phe Asn
65                  70                  75                  80
Glu Lys Val Ala Lys Ala Thr Gly Val Asn Ile Ile Met Gly Thr Gly
                85                  90                  95
Phe Tyr Thr Tyr Thr Glu Ile Pro Phe Tyr Phe Lys Asn Arg Gly Ile
            100                 105                 110
Asp Ser Leu Val Asp Ala Phe Val His Asp Ile Thr Ile Gly Ile Gln
        115                 120                 125
Gly Thr Asn Thr Arg Ala Ala Phe Val Lys Ala Val Ile Asp Ser Ser
    130                 135                 140
Gly Leu Thr Lys Asp Val Glu Met Ala Ile Arg Ala Ala Ala Lys Ala
145                 150                 155                 160
```

```
His Ile Lys Thr Asp Val Pro Ile Ile Thr His Ser Phe Val Gly Asn
            165                 170                 175

Lys Ser Ser Leu Asp Leu Ile Arg Ile Phe Lys Glu Glu Gly Val Asp
        180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
            245                 250                 255

Asp Tyr Cys Pro Thr Ile Asp Gly Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
        290                 295                 300

Ile Asp Asn Pro Arg Arg Leu Phe Thr Gly Arg
305                 310                 315

<210> SEQ ID NO 198
<211> LENGTH: 315
<212> TYPE: PRT
<213> ORGANISM: Vulcanisaeta moutnovskia

<400> SEQUENCE: 198

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
            85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
            165                 170                 175

Lys Ser Ser Leu Asp Leu Ile Arg Ile Phe Lys Glu Glu Gly Val Asp
        180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220
```

```
Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
            245                 250                 255

Asp Tyr Cys Pro Thr Ile Asp Asn Tyr Pro Pro Glu Val Val Arg Ser
        260                 265                 270

Thr Val Pro Asp Trp Thr Met Thr Leu Ile Phe Glu Lys Val Ile Pro
    275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 199
<211> LENGTH: 315
<212> TYPE: PRT
<213> ORGANISM: Vulcanisaeta moutnovskia

<400> SEQUENCE: 199

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
            245                 250                 255

Asp Tyr Cys Pro Thr Ile Asp Pro Tyr Pro Pro Glu Val Val Arg Ser
        260                 265                 270

Thr Val Pro Asp Trp Thr Met Thr Leu Ile Phe Glu Lys Val Ile Pro
```

```
            275                 280                 285
Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 200
<211> LENGTH: 315
<212> TYPE: PRT
<213> ORGANISM: Vulcanisaeta moutnovskia

<400> SEQUENCE: 200

Met Val Arg Ile Ser Ile Ala Gly Gly Asn Glu Ile Asp Pro Gly Ser
1               5                  10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
    130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Gln Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 201
<211> LENGTH: 315
```

<212> TYPE: PRT
<213> ORGANISM: Vulcanisaeta moutnovskia

<400> SEQUENCE: 201

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
            130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Arg Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 202
<211> LENGTH: 315
<212> TYPE: PRT
<213> ORGANISM: Vulcanisaeta moutnovskia

<400> SEQUENCE: 202

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
 50                  55                  60

Ile Ile Asp Leu Thr Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Tyr Thr Tyr Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Ser Tyr Pro Pro Glu Val Val Arg Ser
                260                 265                 270

Thr Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 203
<211> LENGTH: 315
<212> TYPE: PRT
<213> ORGANISM: Vulcanisaeta moutnovskia

<400> SEQUENCE: 203

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
 50                  55                  60

Ile Ile Asp Leu Thr Val Ala Gly Ile Gly Cys Asp Val Arg Phe Asn
 65                  70                  75                  80

Glu Lys Val Ala Lys Ala Thr Gly Val Asn Ile Ile Met Gly Thr Gly
                 85                  90                  95

Phe Tyr Thr Tyr Thr Glu Ile Pro Phe Tyr Lys Asn Arg Gly Ile
                100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Ser His
                245                 250                 255

Asp Tyr Cys Pro Thr Ile Asp Tyr Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315

<210> SEQ ID NO 204
<211> LENGTH: 315
<212> TYPE: PRT
<213> ORGANISM: Vulcanisaeta moutnovskia

<400> SEQUENCE: 204

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65              70                  75                  80

Glu Lys Val Ala Lys Ala Thr Gly Val Asn Ile Met Gly Thr Gly
            85                  90                  95

Phe Tyr Thr Tyr Thr Glu Ile Pro Phe Tyr Lys Asn Arg Gly Ile
                100                 105                 110

Asp Ser Leu Val Asp Ala Phe His Asp Ile Thr Ile Gly Ile Gln
            115                 120                 125

Gly Thr Asn Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala

```
        145                 150                 155                 160
    His Ile Lys Thr Asp Val Pro Ile Ile Thr His Ser Phe Val Gly Asn
                    165                 170                 175

Lys Ser Ser Leu Asp Leu Ile Arg Ile Phe Lys Glu Glu Gly Val Asp
                    180                 185                 190

Leu Ala Arg Thr Val Ile Gly His Val Gly Asp Thr Asp Asp Ile Ser
                    195                 200                 205

Phe Ile Glu Gln Ile Leu Arg Glu Gly Ala Phe Ile Gly Leu Asp Arg
                    210                 215                 220

Phe Gly Leu Asp Ile Tyr Leu Pro Leu Asp Lys Arg Val Lys Thr Ala
    225                 230                 235                 240

Ile Glu Leu Ile Lys Arg Gly Trp Ile Asp Gln Leu Leu Leu Ser His
                    245                 250                 255

Asp Tyr Cys Pro Thr Ile Asp Asp Tyr Pro Pro Glu Val Val Arg Ser
                    260                 265                 270

Thr Val Pro Asp Trp Thr Met Thr Leu Ile Phe Glu Lys Val Ile Pro
                    275                 280                 285

Arg Met Arg Ser Glu Gly Ile Thr Glu Glu Gln Ile Asn Arg Val Leu
                    290                 295                 300

Ile Asp Asn Pro Arg Arg Leu Phe Thr Gly Arg
    305                 310                 315

<210> SEQ ID NO 205
<211> LENGTH: 315
<212> TYPE: PRT
<213> ORGANISM: Vulcanisaeta moutnovskia

<400> SEQUENCE: 205

Met Val Arg Ile Ser Ile Ala Gly Gly Asn Glu Ile Asp Pro Gly Ser
    1               5                   10                  15

Met Gly Leu Thr Leu Phe His Glu His Leu Arg Leu Ile Thr Glu Val
                    20                  25                  30

Val Arg Trp Asn Trp Pro His Leu Tyr Asn Glu Asp Glu Glu Leu Lys
                    35                  40                  45

Arg Ala Ile Asp Ala Val Asn Ala Ala Lys Lys Tyr Gly Val Lys Thr
                    50                  55                  60

Ile Ile Asp Leu Thr Val Ala Gly Ile Gly Cys Asp Val Arg Phe Asn
    65                  70                  75                  80

Glu Lys Val Ala Lys Ala Thr Gly Val Asn Ile Ile Met Gly Thr Gly
                    85                  90                  95

Phe Tyr Thr Tyr Thr Glu Ile Pro Phe Tyr Phe Lys Asn Arg Gly Ile
                    100                 105                 110

Asp Ser Leu Val Asp Ala Phe Val His Asp Ile Thr Ile Gly Ile Gln
                    115                 120                 125

Gly Thr Asn Thr Arg Ala Ala Phe Val Lys Ala Val Ile Asp Ser Ser
                    130                 135                 140

Gly Leu Thr Lys Asp Val Glu Met Ala Ile Arg Ala Ala Lys Ala
    145                 150                 155                 160

His Ile Lys Thr Asp Val Pro Ile Ile Thr His Ser Phe Val Gly Asn
                    165                 170                 175

Lys Ser Ser Leu Asp Leu Ile Arg Ile Phe Lys Glu Glu Gly Val Asp
                    180                 185                 190

Leu Ala Arg Thr Val Ile Gly His Val Gly Asp Thr Asp Asp Ile Ser
                    195                 200                 205
```

```
Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Glu Tyr Pro Pro Glu Val Val Arg Ser
                260                 265                 270

Thr Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
290                 295                 300

Ile Asp Asn Pro Arg Arg Leu Phe Thr Gly Arg
305                 310                 315

<210> SEQ ID NO 206
<211> LENGTH: 315
<212> TYPE: PRT
<213> ORGANISM: Vulcanisaeta moutnovskia

<400> SEQUENCE: 206

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
                20                  25                  30

Val Arg Trp Asn Trp Pro His Leu Tyr Asn Glu Asp Glu Glu Leu Lys
            35                  40                  45

Arg Ala Ile Asp Ala Val Asn Ala Ala Lys Lys Tyr Gly Val Lys Thr
        50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
                100                 105                 110

Asp Ser Leu Val Asp Ala Phe Val His Asp Ile Thr Ile Gly Ile Gln
            115                 120                 125

Gly Thr Asn Thr Arg Ala Ala Phe Val Lys Ala Val Ile Asp Ser Ser
        130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp His Tyr Pro Pro Glu Val Val Arg Ser
                260                 265                 270
```

```
Thr Val Pro Asp Trp Thr Met Thr Leu Ile Phe Glu Lys Val Ile Pro
            275                 280                 285

Arg Met Arg Ser Glu Gly Ile Thr Glu Glu Gln Ile Asn Arg Val Leu
        290                 295                 300

Ile Asp Asn Pro Arg Arg Leu Phe Thr Gly Arg
305                 310                 315

<210> SEQ ID NO 207
<211> LENGTH: 315
<212> TYPE: PRT
<213> ORGANISM: Vulcanisaeta moutnovskia

<400> SEQUENCE: 207

Met Val Arg Ile Ser Ile Ala Gly Gly Asn Glu Ile Asp Pro Gly Ser
1               5                   10                  15

Met Gly Leu Thr Leu Phe His Glu His Leu Arg Leu Ile Thr Glu Val
            20                  25                  30

Val Arg Trp Asn Trp Pro His Leu Tyr Asn Glu Asp Glu Glu Leu Lys
        35                  40                  45

Arg Ala Ile Asp Ala Val Asn Ala Ala Lys Lys Tyr Gly Val Lys Thr
    50                  55                  60

Ile Ile Asp Leu Thr Val Ala Gly Ile Gly Cys Asp Val Arg Phe Asn
65                  70                  75                  80

Glu Lys Val Ala Lys Ala Thr Gly Val Asn Ile Ile Met Gly Thr Gly
                85                  90                  95

Phe Tyr Thr Tyr Thr Glu Ile Pro Phe Tyr Phe Lys Asn Arg Gly Ile
            100                 105                 110

Asp Ser Leu Val Asp Ala Phe Val His Asp Ile Thr Ile Gly Ile Gln
        115                 120                 125

Gly Thr Asn Thr Arg Ala Ala Phe Val Lys Ala Val Ile Asp Ser Ser
130                 135                 140

Gly Leu Thr Lys Asp Val Glu Met Ala Ile Arg Ala Ala Ala Lys Ala
145                 150                 155                 160

His Ile Lys Thr Asp Val Pro Ile Ile Thr His Ser Phe Val Gly Asn
                165                 170                 175

Lys Ser Ser Leu Asp Leu Ile Arg Ile Phe Lys Glu Glu Gly Val Asp
            180                 185                 190

Leu Ala Arg Thr Val Ile Gly His Val Gly Asp Thr Asp Asp Ile Ser
        195                 200                 205

Phe Ile Glu Gln Ile Leu Arg Glu Gly Ala Phe Ile Gly Leu Asp Arg
    210                 215                 220

Phe Gly Leu Asp Ile Tyr Leu Pro Leu Asp Lys Arg Val Lys Thr Ala
225                 230                 235                 240

Ile Glu Leu Ile Lys Arg Gly Trp Ile Asp Gln Leu Leu Leu Ser His
                245                 250                 255

Asp Tyr Cys Pro Thr Ile Asp Lys Tyr Pro Pro Glu Val Val Arg Ser
            260                 265                 270

Thr Val Pro Asp Trp Thr Met Thr Leu Ile Phe Glu Lys Val Ile Pro
        275                 280                 285

Arg Met Arg Ser Glu Gly Ile Thr Glu Glu Gln Ile Asn Arg Val Leu
    290                 295                 300

Ile Asp Asn Pro Arg Arg Leu Phe Thr Gly Arg
305                 310                 315
```

```
<210> SEQ ID NO 208
<211> LENGTH: 43
<212> TYPE: DNA
<213> ORGANISM: Artificial Sequence
<220> FEATURE:
<223> OTHER INFORMATION: Primer

<400> SEQUENCE: 208
tgtttcatga acatctgcgt gttattaccg aagttgttcg ttg          43

<210> SEQ ID NO 209
<211> LENGTH: 43
<212> TYPE: DNA
<213> ORGANISM: Artificial Sequence
<220> FEATURE:
<223> OTHER INFORMATION: Primer

<400> SEQUENCE: 209
caacgaacaa cttcggtaat aacacgcaga tgttcatgaa aca          43

<210> SEQ ID NO 210
<211> LENGTH: 43
<212> TYPE: DNA
<213> ORGANISM: Artificial Sequence
<220> FEATURE:
<223> OTHER INFORMATION: Primer

<400> SEQUENCE: 210
tgtttcatga acatctgcgt gcaattaccg aagttgttcg ttg          43

<210> SEQ ID NO 211
<211> LENGTH: 43
<212> TYPE: DNA
<213> ORGANISM: Artificial Sequence
<220> FEATURE:
<223> OTHER INFORMATION: Primer

<400> SEQUENCE: 211
caacgaacaa cttcggtaat tgcacgcaga tgttcatgaa aca          43

<210> SEQ ID NO 212
<211> LENGTH: 43
<212> TYPE: DNA
<213> ORGANISM: Artificial Sequence
<220> FEATURE:
<223> OTHER INFORMATION: Primer

<400> SEQUENCE: 212
tgtttcatga acatctgcgt ggcattaccg aagttgttcg ttg          43

<210> SEQ ID NO 213
<211> LENGTH: 43
<212> TYPE: DNA
<213> ORGANISM: Artificial Sequence
<220> FEATURE:
<223> OTHER INFORMATION: Primer

<400> SEQUENCE: 213
caacgaacaa cttcggtaat gccacgcaga tgttcatgaa aca          43

<210> SEQ ID NO 214
<211> LENGTH: 43
<212> TYPE: DNA
<213> ORGANISM: Artificial Sequence
<220> FEATURE:
<223> OTHER INFORMATION: Primer
```

```
<400> SEQUENCE: 214
tgggcaccgg tttttatacc gaaaccgaaa tcccgttcta ttt          43

<210> SEQ ID NO 215
<211> LENGTH: 43
<212> TYPE: DNA
<213> ORGANISM: Artificial Sequence
<220> FEATURE:
<223> OTHER INFORMATION: Primer

<400> SEQUENCE: 215
aaatagaacg ggatttcggt ttcggtataa aaaccggtgc cca          43

<210> SEQ ID NO 216
<211> LENGTH: 43
<212> TYPE: DNA
<213> ORGANISM: Artificial Sequence
<220> FEATURE:
<223> OTHER INFORMATION: Primer

<400> SEQUENCE: 216
gtgcatttat tggtctggat cagtttggcc tggatattta tct          43

<210> SEQ ID NO 217
<211> LENGTH: 43
<212> TYPE: DNA
<213> ORGANISM: Artificial Sequence
<220> FEATURE:
<223> OTHER INFORMATION: Primer

<400> SEQUENCE: 217
agataaatat ccaggccaaa ctgatccaga ccaataaatg cac          43

<210> SEQ ID NO 218
<211> LENGTH: 43
<212> TYPE: DNA
<213> ORGANISM: Artificial Sequence
<220> FEATURE:
<223> OTHER INFORMATION: Primer

<400> SEQUENCE: 218
attattgtcc gaccattgat gcatatccgc ctgaagttgt gcg          43

<210> SEQ ID NO 219
<211> LENGTH: 43
<212> TYPE: DNA
<213> ORGANISM: Artificial Sequence
<220> FEATURE:
<223> OTHER INFORMATION: Primer

<400> SEQUENCE: 219
cgcacaactt caggcggata tgcatcaatg gtcggacaat aat          43

<210> SEQ ID NO 220
<211> LENGTH: 43
<212> TYPE: DNA
<213> ORGANISM: Artificial Sequence
<220> FEATURE:
<223> OTHER INFORMATION: Primer

<400> SEQUENCE: 220
attattgtcc gaccattgat tgttatccgc ctgaagttgt gcg          43

<210> SEQ ID NO 221
<211> LENGTH: 43
```

```
<212> TYPE: DNA
<213> ORGANISM: Artificial Sequence
<220> FEATURE:
<223> OTHER INFORMATION: Primer

<400> SEQUENCE: 221
cgcacaactt caggcggata acaatcaatg gtcggacaat aat          43

<210> SEQ ID NO 222
<211> LENGTH: 43
<212> TYPE: DNA
<213> ORGANISM: Artificial Sequence
<220> FEATURE:
<223> OTHER INFORMATION: Primer

<400> SEQUENCE: 222
attattgtcc gaccattgat ggctatccgc ctgaagttgt gcg          43

<210> SEQ ID NO 223
<211> LENGTH: 43
<212> TYPE: DNA
<213> ORGANISM: Artificial Sequence
<220> FEATURE:
<223> OTHER INFORMATION: Primer

<400> SEQUENCE: 223
cgcacaactt caggcggata gccatcaatg gtcggacaat aat          43

<210> SEQ ID NO 224
<211> LENGTH: 43
<212> TYPE: DNA
<213> ORGANISM: Artificial Sequence
<220> FEATURE:
<223> OTHER INFORMATION: Primer

<400> SEQUENCE: 224
attattgtcc gaccattgat atttatccgc ctgaagttgt gcg          43

<210> SEQ ID NO 225
<211> LENGTH: 43
<212> TYPE: DNA
<213> ORGANISM: Artificial Sequence
<220> FEATURE:
<223> OTHER INFORMATION: Primer

<400> SEQUENCE: 225
cgcacaactt caggcggata aatatcaatg gtcggacaat aat          43

<210> SEQ ID NO 226
<211> LENGTH: 43
<212> TYPE: DNA
<213> ORGANISM: Artificial Sequence
<220> FEATURE:
<223> OTHER INFORMATION: Primer

<400> SEQUENCE: 226
attattgtcc gaccattgat atgtatccgc ctgaagttgt gcg          43

<210> SEQ ID NO 227
<211> LENGTH: 43
<212> TYPE: DNA
<213> ORGANISM: Artificial Sequence
<220> FEATURE:
<223> OTHER INFORMATION: Primer

<400> SEQUENCE: 227
```
cgcacaactt caggcggata catatcaatg gtcggacaat aat            43

<210> SEQ ID NO 228
<211> LENGTH: 43
<212> TYPE: DNA
<213> ORGANISM: Artificial Sequence
<220> FEATURE:
<223> OTHER INFORMATION: Primer

<400> SEQUENCE: 228
attattgtcc gaccattgat aattatccgc ctgaagttgt gcg            43

<210> SEQ ID NO 229
<211> LENGTH: 43
<212> TYPE: DNA
<213> ORGANISM: Artificial Sequence
<220> FEATURE:
<223> OTHER INFORMATION: Primer

<400> SEQUENCE: 229
cgcacaactt caggcggata attatcaatg gtcggacaat aat            43

<210> SEQ ID NO 230
<211> LENGTH: 43
<212> TYPE: DNA
<213> ORGANISM: Artificial Sequence
<220> FEATURE:
<223> OTHER INFORMATION: Primer

<400> SEQUENCE: 230
attattgtcc gaccattgat ccgtatccgc ctgaagttgt gcg            43

<210> SEQ ID NO 231
<211> LENGTH: 43
<212> TYPE: DNA
<213> ORGANISM: Artificial Sequence
<220> FEATURE:
<223> OTHER INFORMATION: Primer

<400> SEQUENCE: 231
cgcacaactt caggcggata cggatcaatg gtcggacaat aat            43

<210> SEQ ID NO 232
<211> LENGTH: 43
<212> TYPE: DNA
<213> ORGANISM: Artificial Sequence
<220> FEATURE:
<223> OTHER INFORMATION: Primer

<400> SEQUENCE: 232
attattgtcc gaccattgat cagtatccgc ctgaagttgt gcg            43

<210> SEQ ID NO 233
<211> LENGTH: 43
<212> TYPE: DNA
<213> ORGANISM: Artificial Sequence
<220> FEATURE:
<223> OTHER INFORMATION: Primer

<400> SEQUENCE: 233
cgcacaactt caggcggata ctgatcaatg gtcggacaat aat            43

<210> SEQ ID NO 234
<211> LENGTH: 43
<212> TYPE: DNA
<213> ORGANISM: Artificial Sequence

```
<220> FEATURE:
<223> OTHER INFORMATION: Primer

<400> SEQUENCE: 234
attattgtcc gaccattgat agctatccgc ctgaagttgt gcg            43

<210> SEQ ID NO 235
<211> LENGTH: 43
<212> TYPE: DNA
<213> ORGANISM: Artificial Sequence
<220> FEATURE:
<223> OTHER INFORMATION: Primer

<400> SEQUENCE: 235
cgcacaactt caggcggata gctatcaatg gtcggacaat aat            43

<210> SEQ ID NO 236
<211> LENGTH: 43
<212> TYPE: DNA
<213> ORGANISM: Artificial Sequence
<220> FEATURE:
<223> OTHER INFORMATION: Primer

<400> SEQUENCE: 236
attattgtcc gaccattgat acctatccgc ctgaagttgt gcg            43

<210> SEQ ID NO 237
<211> LENGTH: 43
<212> TYPE: DNA
<213> ORGANISM: Artificial Sequence
<220> FEATURE:
<223> OTHER INFORMATION: Primer

<400> SEQUENCE: 237
cgcacaactt caggcggata ggtatcaatg gtcggacaat aat            43

<210> SEQ ID NO 238
<211> LENGTH: 43
<212> TYPE: DNA
<213> ORGANISM: Artificial Sequence
<220> FEATURE:
<223> OTHER INFORMATION: Primer

<400> SEQUENCE: 238
attattgtcc gaccattgat gtttatccgc ctgaagttgt gcg            43

<210> SEQ ID NO 239
<211> LENGTH: 43
<212> TYPE: DNA
<213> ORGANISM: Artificial Sequence
<220> FEATURE:
<223> OTHER INFORMATION: Primer

<400> SEQUENCE: 239
cgcacaactt caggcggata aacatcaatg gtcggacaat aat            43

<210> SEQ ID NO 240
<211> LENGTH: 43
<212> TYPE: DNA
<213> ORGANISM: Artificial Sequence
<220> FEATURE:
<223> OTHER INFORMATION: Primer

<400> SEQUENCE: 240
attattgtcc gaccattgat tattatccgc ctgaagttgt gcg            43
```

<210> SEQ ID NO 241
<211> LENGTH: 43
<212> TYPE: DNA
<213> ORGANISM: Artificial Sequence
<220> FEATURE:
<223> OTHER INFORMATION: Primer

<400> SEQUENCE: 241
cgcacaactt caggcggata ataatcaatg gtcggacaat aat            43

<210> SEQ ID NO 242
<211> LENGTH: 43
<212> TYPE: DNA
<213> ORGANISM: Artificial Sequence
<220> FEATURE:
<223> OTHER INFORMATION: Primer

<400> SEQUENCE: 242
attattgtcc gaccattgat gattatccgc ctgaagttgt gcg            43

<210> SEQ ID NO 243
<211> LENGTH: 43
<212> TYPE: DNA
<213> ORGANISM: Artificial Sequence
<220> FEATURE:
<223> OTHER INFORMATION: Primer

<400> SEQUENCE: 243
cgcacaactt caggcggata atcatcaatg gtcggacaat aat            43

<210> SEQ ID NO 244
<211> LENGTH: 43
<212> TYPE: DNA
<213> ORGANISM: Artificial Sequence
<220> FEATURE:
<223> OTHER INFORMATION: Primer

<400> SEQUENCE: 244
attattgtcc gaccattgat gaatatccgc ctgaagttgt gcg            43

<210> SEQ ID NO 245
<211> LENGTH: 43
<212> TYPE: DNA
<213> ORGANISM: Artificial Sequence
<220> FEATURE:
<223> OTHER INFORMATION: Primer

<400> SEQUENCE: 245
cgcacaactt caggcggata ttcatcaatg gtcggacaat aat            43

<210> SEQ ID NO 246
<211> LENGTH: 43
<212> TYPE: DNA
<213> ORGANISM: Artificial Sequence
<220> FEATURE:
<223> OTHER INFORMATION: Primer

<400> SEQUENCE: 246
attattgtcc gaccattgat ttttatccgc ctgaagttgt gcg            43

<210> SEQ ID NO 247
<211> LENGTH: 43
<212> TYPE: DNA
<213> ORGANISM: Artificial Sequence
<220> FEATURE:
<223> OTHER INFORMATION: Primer

<400> SEQUENCE: 247
cgcacaactt caggcggata aaaatcaatg gtcggacaat aat                43

<210> SEQ ID NO 248
<211> LENGTH: 43
<212> TYPE: DNA
<213> ORGANISM: Artificial Sequence
<220> FEATURE:
<223> OTHER INFORMATION: Primer

<400> SEQUENCE: 248
attattgtcc gaccattgat cattatccgc ctgaagttgt gcg                43

<210> SEQ ID NO 249
<211> LENGTH: 43
<212> TYPE: DNA
<213> ORGANISM: Artificial Sequence
<220> FEATURE:
<223> OTHER INFORMATION: Primer

<400> SEQUENCE: 249
cgcacaactt caggcggata atgatcaatg gtcggacaat aat                43

<210> SEQ ID NO 250
<211> LENGTH: 43
<212> TYPE: DNA
<213> ORGANISM: Artificial Sequence
<220> FEATURE:
<223> OTHER INFORMATION: Primer

<400> SEQUENCE: 250
attattgtcc gaccattgat aaatatccgc ctgaagttgt gcg                43

<210> SEQ ID NO 251
<211> LENGTH: 43
<212> TYPE: DNA
<213> ORGANISM: Artificial Sequence
<220> FEATURE:
<223> OTHER INFORMATION: Primer

<400> SEQUENCE: 251
cgcacaactt caggcggata tttatcaatg gtcggacaat aat                43

<210> SEQ ID NO 252
<211> LENGTH: 43
<212> TYPE: DNA
<213> ORGANISM: Artificial Sequence
<220> FEATURE:
<223> OTHER INFORMATION: Primer

<400> SEQUENCE: 252
attattgtcc gaccattgat ctgtatccgc ctgaagttgt gcg                43

<210> SEQ ID NO 253
<211> LENGTH: 43
<212> TYPE: DNA
<213> ORGANISM: Artificial Sequence
<220> FEATURE:
<223> OTHER INFORMATION: Primer

<400> SEQUENCE: 253
cgcacaactt caggcggata cagatcaatg gtcggacaat aat                43

```
<210> SEQ ID NO 254
<211> LENGTH: 43
<212> TYPE: DNA
<213> ORGANISM: Artificial Sequence
<220> FEATURE:
<223> OTHER INFORMATION: Primer

<400> SEQUENCE: 254
attattgtcc gaccattgat cgttatccgc ctgaagttgt gcg          43

<210> SEQ ID NO 255
<211> LENGTH: 43
<212> TYPE: DNA
<213> ORGANISM: Artificial Sequence
<220> FEATURE:
<223> OTHER INFORMATION: Primer

<400> SEQUENCE: 255
cgcacaactt caggcggata acgatcaatg gtcggacaat aat          43
```

VULCANISAETAL PHOSPHOTRIESTERASE-LIKE LACTONASES (PLL) HAVING ENHANCED PROPERTIES AND THE USES THEREOF

FIELD OF THE INVENTION

The present invention relates to Vulcanisaetal Phosphotriesterase-Like Lactonases (PLL) having enhanced properties and the uses thereof, notably as bioscavenger of organophosphorus compounds or as quorum quencher of the bacteria using lactones to communicate.

BACKGROUND OF THE INVENTION

Organophosphate (OPs) insecticides have become the most widely used insecticides available today. OPs are used in agriculture, at home, in gardens, and in veterinary practice. Since most of these compounds inhibit some esterase enzymes, exposure to OPs can lead to serious toxicity by multiple routes. Irreversible inhibition of acetylcholinesterase by OPs, a key enzyme of the mammalian nervous system, causes severe damage for all vertebrates. Loss of enzyme function leads to accumulation of acetylcholine in different compartments of the body causing muscle contraction, paralysis and respiratory depression. Increased pulmonary secretions with respiratory failure are the usual causes of death from organophosphate poisoning.

Some of OPs have also been developed by armies before the World War II. The discovery of OPs with improved toxicity and/or higher stability has led to the development of chemical warfar agents (CWA) such as sarin, soman, tabun or VX. Moreover, OPs insecticides, being easily accessible and not so less toxic as compared to CWA OPs, constitute an important risk for the population. Faced with these growing threats, the development of anti-dotes has never been more urgent.

OPs are efficiently absorbed by inhalation, ingestion, and skin penetration because of the hydrophobicity of these molecules. The occurrence of poisoning depends on the absorption rate of the compound. Symptoms of acute OPs poisoning develop during or after exposure, within minutes to hours, depending of the method of the contact. Exposure by inhalation results in the fastest appearance of toxic symptoms, followed by the gastrointestinal route and finally dermal route.

Protective suits and masks do not always offer an effective protection against OPs. In patients poisoned by OPs contamination of skin, clothing or hair, decontamination must proceed with surgical soap or laundry detergents. Treatment of highly contaminated persons results in administering atropine or diazepam which antagonizes the effects of excessive concentrations of acetylcholine at end-organs having muscarinic receptors. Unfortunately, atropine remains ineffective against nicotinic actions, specifically muscle weakness and respiratory depression in case of severe poisoning. Pralidoxime, a cholinesterase reactivator, relieves the nicotinic as well as the muscarinic effects of OPs poisoning when administering quickly after poisoning. The use of this compound remains uneffective against sarin which holds a very quickly effect once inhaled. Clearing airway and improving tissue oxygenation is also very helpful.

Although some progress in prophylaxia has been made with the abovementioned techniques, existing protection and the treatments for these poisoning nevertheless remain unsatisfactory.

The first OPs-hydrolases have been identified in several bacteria in the early 90's (Cheng et al., 1993, Appl. Environ. Microbiol., 59: 3138-3140, Raveh et al., 1993, Biochem Pharmacol., 45: 2465-2474). Butyrylcholinesterase (BChE)- and acetylcholinesterase (AChE)-based OP bioscavengers were considered as potential stoichiometric traps. Unfortunately, due to their low stoichiometric binding capacity to OPs, huge quantity of BChE or AchE is needed to cure the poisoning individuals. This renders the use of these enzymes disproportionate and quite expensive.

Some other microbial enzymes generally called phosphotriesterases (PTEs) show preferences for organophosphorous compounds with P—O or P—S bonds. These enzymes are members of the aminohydrolase superfamily, enzymes catalyzing hydrolysis of a broad range of compounds with different chemical properties (phosphoesters, esters, amides, etc). Their coding genes, opd (organo phosphate degradation), were isolated in soil bacteria such as *Pseudomonas diminuta*, also called *Brevundominas diminuta* (Munnecke et al., 1976, Appl. Environ. Microbiol., 32: 7-13), *Flavobacterium* sp. (Sethunathan et al., 1973, Can J Microbiol, 19: 873-875) and *Agrobacterium radiobacter* (Horne et al., 2003, FEMS Microbiol Lett, 222: 1-8), and genes similar to opd were also identified in Archaea (Merone et al., 2005, Extremophiles, 9: 297-305).

Lactones are signalling molecules synthesized by bacteria which allow them to detect the population density. This cell-to-cell communication process is termed quorum sensing (QS) and is well known to modulate many key biological functions of bacteria including biofilm formation (Popat et al., 2008, British Medical Bulletin, 87: 63-75). This link between QS and virulence is central to the pathogenesis of many bacterial infections, including *P. aeruginosa* (Sakuragi et al., 2007, J Bacteriol, 189: 5383-5386) but also *A. baumanii* (Stacy et al., 2012, ACS Chem Biol, 7(10): 1719-1728), *Bulkolderia* sp. (McKeon et al., 2011, J Infect Dis, February 1; 203(3):383-92), *Vibrio* sp. (Augustine et al., 2010, Arch Microbiol 192(12): 1019-1022) or *E. caratovora* (Dong et al., 2001, Nature, 411: 813-817). Interfering with QS system, also called quorum quenching, is a promising approach to control bacterial diseases in plants and animals (Dong et al., 2001, nature, 411: 813-817). N-acylhomoserine lactones (AHLs) are molecules that mediate bacterial communication for many Gram negative bacteria and some Archaeal organisms (Zhang et al., 2012, ISME J., July; 6(7):1336-44). It classically regulates infection and virulence functions. These molecules accumulate in the media to reach a certain threshold for which the transcriptional profile of the bacteria is altered (Hentzer et al., 2003, Embo J, 22: 3803-3815). By hydrolyzing AHLs, lactonases like PLLs can quench the AHL-mediated communication between bacteria, as seen for human paraoxonases (Ma et al., 2009, Appl Microbiol Biotechnol, 83: 135-141) or AiiA lactonase (Dong et al., 2001, Nature, 411: 813-817). Because of their dual catalytic activities, lactonases and phosphotriesterases, PLLs constitute highly attractive candidate for biotechnological utilization as quorum quenching agent or OPs bioscavenger.

Recently, new thermophilic bacteria belonging to the phylum of crenarchaeota have been discovered in Japan and Russia. *Vulcanisaeta* species were found in hot springs of volcano area. The complete genome of two currently known *Vulcanisaeta* species, *V. distribute* and *V. moutnovskia* was sequenced aiming to understand the physiological properties of this archaeon and their possible ecological roles (Mavromatis et al., 2010, Stand Genomic Sci.; 3(2):117-25/ Gumerov et al., 2011, J Bacteriol.; 193(9):2355-6). Among the protein-coding genes, few sequences share similarities with the ones encoding hyperthermophilic PTEs or Sulfolobal PLL lactonases, assuming some similar enzymatic activities.

Phylogenetics and sequence alignment of PTEs genes with *V. moutnovskia* genes show a percentage of identity close to 30%. Due to the low sequence of identity with known OP hydrolases and lactonases (maximum 50%) different substrate specificities and catalytic properties are highly expected.

SUMMARY OF THE INVENTION

One aspect of the present invention is to provide, novel mutated hyperthermophilic PTEs having a lactonase activity, having the advantages of being both:
more active vis-à-vis the OPs, or more active vis-à-vis the AHLs, or more active vis-à-vis the OPs and vis-à-vis the AHLs than the wild type hyperthermophilic PTEs,
more stable and less expensive to produce than the mesophilic PTEs.

Another aspect of the present invention contemplates a method for the establishment of a library of mutated hyperthermophilic PTE variants.

Another aspect of the present invention is to provide efficient tools for the decontamination of OPs polluted surfaces of materials, of the skin, of hairs or mucous membranes. Said tools can be compositions, bioscavengers, cartridge decontamination, kit of decontamination, impregnated materials with new mutated hyperthermophilic PTEs.

Another aspect of the present invention is to provide vectors and host cells able to synthesize the new mutated hyperthermophilic PTEs in large scale with a reduced cost.

Yet another aspect of the present invention is directed to the use of new mutated hyperthermophilic PTEs as bioscavengers within the context of the decontamination of the surfaces of materials, of the skin or mucous membranes contaminated with organophosphorus compounds, or within the context of the pollution control of water polluted with organophosphorus compounds, or within the context of the destruction of stocks of neurotoxic agents.

Still another aspect of the present invention is to provide compositions comprising new mutated hyperthermophilic PTEs for their use in the treatment of diseases caused by bacteria using AHLs to communicate. The expression bacteria relates not only to bacteria but also to Archae.

DETAILED DESCRIPTION OF THE INVENTION

Figure 1:
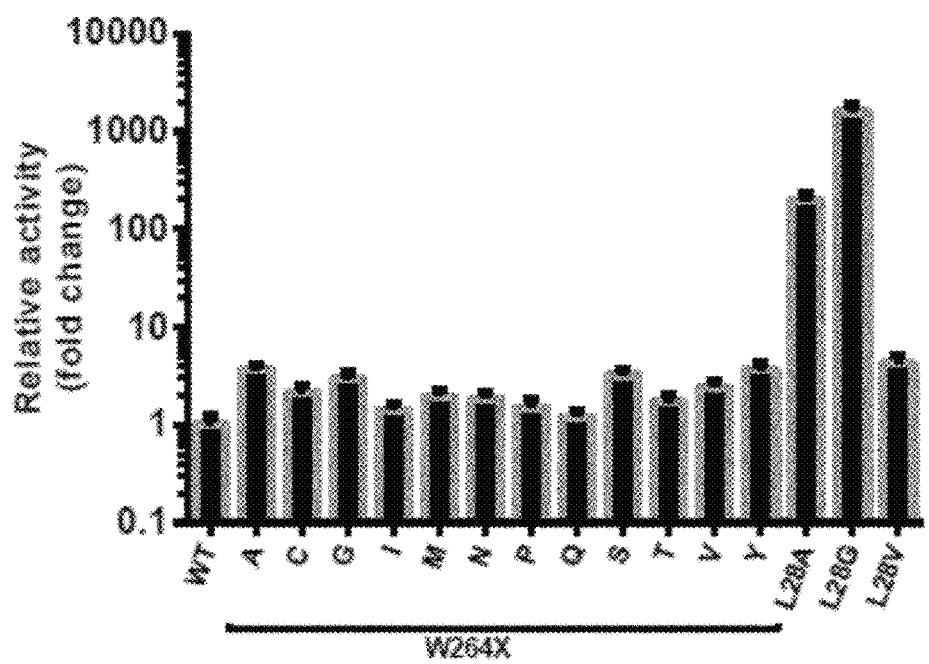
FIG. 1 is a histogram representation of relative activities of VmoLac variants as compared to the wild type enzyme against paraoxon (1 mM). The Y axis indicates the relative activity (fold change) compared to the wild type (mean values+/−SD).

A subject of the invention is a mutated hyperthermophilic PTE having a lactonase activity derived from a hyperthermophilic phosphotriesterase corresponding to the consensus sequence of SEQ ID NO: 1 or having at least 70% or more identity to the amino acid sequence of SEQ ID NO: 1, said mutated PTE comprising the at least one mutation selected from the group consisting of:
substitution of the glycine G in position 9,
substitution of the glycine G in position 10,
substitution of the leucine L in position 29,
substitution of the leucine L in position 48,
substitution of the asparagine N in position 56,
substitution of the leucine L in position 69,
substitution of the threonine T in position 70,
substitution of the isoleucine I in position 74,
substitution of the valine V in position 78,
substitution of the alanine A in position 85,
substitution of the tyrosine Y in position 99,
substitution of the tyrosine Y in position 101,
substitution of the valine V in position 121,
substitution of the isoleucine I in position 124,
substitution of the asparagine N in position 132,
substitution of the aspartic acid D in position 143,
substitution of the aspartic acid D in position 166,
substitution of the isoleucine I in position 169,
substitution of the aspartic acid D in position 193,
substitution of the alanine A in position 195,
substitution of the arginine R in position 225,
substitution of the glycine G in position 227,
substitution of the leucine L in position 228,
substitution of the isoleucine I in position 230,
substitution of the tyrosine Y in position 231,
substitution of the leucine L in position 232,
substitution of the tyrosine Y position 259,
substitution of the cysteine C in position 260,
substitution of the proline P in position 261,
substitution of the threonine T in position 262,
substitution of the isoleucine I in position 263,
substitution of the aspartic acid D in position 264,
substitution of the tryptophane W in position 265,
substitution of the tyrosine Y in position 266,
substitution of the proline P in position 267,
substitution of the proline P in position 268,
substitution of the glutamic acid E in position 269,
substitution of the valine V in position 270,
substitution of the valine V in position 271,
substitution of the arginine R in position 272,
substitution of the serine S in position 273,
substitution of the threonine T in position 274,
substitution of the valine V in position 275,
substitution of the proline P in position 276,
substitution of the aspartic acid D in position 277,
substitution of the tryptophan W in position 278,
substitution of the threonine T in position 279,
substitution of the methionine M in position 280,
substitution of the threonine T in position 281,
substitution of the leucine L in position 282,
substitution of the isoleucine I in position 283,
substitution of the phenylalanine F in position 284,
substitution of the glutamic acid E in position 285,
substitution of the threonine T in position 297,
substitution of the glutamic acid E in position 299,
of SEQ ID NO: 1 by any other natural or non-natural amino acid.

PTEs are zinc-metalloproteins that were originally identified for their ability to hydrolyse phosphotriesterase-containing organophosphorous compounds, but recently more members of this family were found to possess lactonase activity as well. Lactonase activity is the ability to hydrolyze the ester bound in the lactone ring.

The expression "mutated hyperthermophilic PTE having a lactonase activity" relates to any enzyme having both lactonase and phosphotriesterase catalytic activities, said enzymes being isolated from thermophilic or hyperthermophilic bacteria belonging to the PLLs or PTEs superfamilies. By "superfamily" is meant a large group of proteins sharing the same fold (topology and secondary structure elements), and the same active site architecture. A superfamily is comprised of dozens of groups of proteins sharing the same three dimensional structure and functions, each group exhibiting a different function. These functions typically share a common element (e.g. a key chemical step in enzyme catalysis) and also the active site residues executing this element. By "thermophilic bacteria" are meant bacteria leaving between 45° C. to 120° C. By "hyperthermophilic bacteria" is meant bacteria for which the optimal temperatures are above 80° C. The thermostability of the enzymes isolated from thermophilic or hyperthermophilic bacteria confers them the advantage of being inexpensive to produce, on the one hand because they are stable in organic solvents which make them more suitable for industrial processes, and, on the other hand, because they are very inexpensive to purify by the technique of heating the cell lysates of the cells producing the above-mentioned enzymes; a large yield and high purity are thus obtained in one stage.

Lactonase and phosphotriesterase catalytic activities can be tested on their respective substrats according to methods disclosed in experimental part of the invention.

The introduction of an amino acid residue in position 2 of SEQ ID NO: 1 results from the experimental protocols used to perform the differents mutated hyperthermophilic PTEs, notably due to the choice of restriction enzyme in the cloning site of vectors for the building of the mutated hyperthermophilic PTEs. For example, the use of NcoI restriction enzyme in the cloning site of said vectors leads to the addition of the alanine residue in position 2 of SEQ ID NO: 1 in order to avoid a change in the reading frame. The introduction of said alanine residue in position 2 of SEQ ID NO: 1 has no effect in the activity of either the wild type or the mutated hyperthermophilic PTEs. It means that two mutated hyperthermophilic PTEs having a sequence derived from SEQ ID NO: 1, one bearing an added alanine residue in position 2, the other one being free of said alanine residue in position 2 share exactly the same enzymatic activity in terms of performance.

The mutated hyperthermophilic phosphotriesterase (PTEs) having a lactonase activity of the invention have the advantage of being more active than the wild type hyperthermophilic phosphotriesterase (PTEs) having a lactonase activity from which they derived not only within the context of hydrolysis of OPs but also within the context of the treatment of diseases caused by bacteria using AHLs to communicate, notably by hydrolysis of AHLs.

The hyperthermophilic PTEs having a lactonase activity of the present invention also have the advantage of being more active:
  within the context of the hydrolysis of the OPs, and/or,
  within the context of quorum quenching, i.e. within the context of resistance to pathogen infections,
than the wild type hyperthermophilic PTEs from which they derived.

By the term "natural amino acid" is meant the amino acids (also called amino acid residues) encoded by the genetic code of any organism. Natural amino acid residues are building blocks of proteins. There are 20 standard amino acids: glycine, alanine, arginine, asparagine, aspartic acid, cysteine, glutamine, glutamic acid, histidine, isoleucine, leucine, lysine, methionine, phenylalanine, proline, serine, threonine, tryptophan, tyrosine and valine.

By the term "non-natural amino acid" is meant synthetic amino acid residues which are not produced directly by standard cellular machinery. These are also called synthetic amino acid residues by the man skilled in the art. They often results from posttranslational modification of proteins.

In a more specific embodiment, the above-mentioned mutated hyperthermophilic PTEs having a lactonase activity according to the present invention, corresponding to the consensus sequence of SEQ ID NO: 1 or having at least 70% or more identity to the amino acid sequence of SEQ ID NO: 1, comprise a single mutation, said mutation being selected from the from the group consisting of:
  substitution of the glycine G in position 9,
  substitution of the glycine G in position 10,
  substitution of the leucine L in position 29,
  substitution of the leucine L in position 48,
  substitution of the asparagine N in position 56,
  substitution of the leucine L in position 69,
  substitution of the threonine T in position 70,
  substitution of the isoleucine I in position 74,
  substitution of the valine V in position 78,
  substitution of the alanine A in position 85,
  substitution of the tyrosine Y in position 99,
  substitution of the tyrosine Y in position 101,
  substitution of the valine V in position 121,
  substitution of the isoleucine I in position 124,
  substitution of the asparagine N in position 132,
  substitution of the aspartic acid D in position 143,
  substitution of the aspartic acid D in position 166,
  substitution of the isoleucine I in position 169,
  substitution of the aspartic acid D in position 193,
  substitution of the alanine A in position 195,
  substitution of the arginine R in position 225,
  substitution of the glycine G in position 227,
  substitution of the leucine L in position 228,
  substitution of the isoleucine I in position 230,
  substitution of the tyrosine Y in position 231,
  substitution of the leucine L in position 232,
  substitution of the tyrosine Y position 259,
  substitution of the cysteine C in position 260,
  substitution of the proline P in position 261,
  substitution of the threonine T in position 262,
  substitution of the isoleucine I in position 263,
  substitution of the aspartic acid D in position 264,
  substitution of the tryptophane W in position 265,
  substitution of the tyrosine Y in position 266,
  substitution of the proline P in position 267,
  substitution of the proline P in position 268,
  substitution of the glutamic acid E in position 269,
  substitution of the valine V in position 270,
  substitution of the valine V in position 271,
  substitution of the arginine R in position 272,
  substitution of the serine S in position 273,
  substitution of the threonine T in position 274,
  substitution of the valine V in position 275,
  substitution of the proline P in position 276,
  substitution of the aspartic acid D in position 277,
  substitution of the tryptophan W in position 278,
  substitution of the threonine T in position 279,
  substitution of the methionine M in position 280,
  substitution of the threonine T in position 281,
  substitution of the leucine L in position 282,
  substitution of the isoleucine I in position 283,
  substitution of the phenylalanine F in position 284,
  substitution of the glutamic acid E in position 285, substitution of the threonine T in position 297,
substitution of the glutamic acid E in position 299,
of SEQ ID NO: 1 by any other natural or non-natural amino acid.

A more particular subject of the present invention is the above-mentioned mutated hyperthermophilic PTEs having a lactonase activity, derived from the hyperthermophilic lactonase of *Vulcanisaeta moutnovskia* corresponding to the sequence of SEQ ID NO: 3, said sequence of SEQ ID NO: 3 belonging to the consensus sequence of SEQ ID NO: 1, the amino acid in position 2 being missing from SEQ ID NO: 3.

In a preferred embodiment, the mutated hyperthermophilic PTEs having a lactonase activity according to the present invention, wherein the amino acid in position 2 in SEQ ID NO: 1 is missing and corresponding to the SEQ ID NO: 3, said SEQ ID NO: 3 being derived from the hyperthermophilic lactonase of *Vulcanisaeta moutnovskia* or having at least 70% or more identity to the amino acid sequence of SEQ ID NO: 3, said mutated PTEs comprise the at least one mutation selected from the group consisting of:

substitution of the glycine G in position 8,
substitution of the glycine G in position 9,
substitution of the leucine L in position 28,
substitution of the leucine L in position 47,
substitution of the asparagine N in position 55,
substitution of the leucine L in position 68,
substitution of the threonine T in position 69,
substitution of the isoleucine I in position 73,
substitution of the valine V in position 77,
substitution of the alanine A in position 84,
substitution of the tyrosine Y in position 98,
substitution of the tyrosine Y in position 100,
substitution of the valine V in position 120,
substitution of the isoleucine I in position 123,
substitution of the asparagine N in position 131,
substitution of the aspartic acid D in position 142,
substitution of the aspartic acid D in position 165,
substitution of the isoleucine I in position 168,
substitution of the aspartic acid D in position 192,
substitution of the alanine A in position 194,
substitution of the arginine R in position 224,
substitution of the glycine G in position 226,
substitution of the leucine L in position 227,
substitution of the isoleucine I in position 229,
substitution of the tyrosine Y in position 230,
substitution of the leucine L in position 231,
substitution of the tyrosine Y position 258,
substitution of the cysteine C in position 259,
substitution of the proline P in position 260,
substitution of the threonine T in position 261,
substitution of the isoleucine I in position 262,
substitution of the aspartic acid D in position 263,
substitution of the tryptophane W in position 264,
substitution of the tyrosine Y in position 265,
substitution of the proline P in position 266,
substitution of the proline P in position 267,
substitution of the glutamic acid E in position 268,
substitution of the valine V in position 269,
substitution of the valine V in position 270,
substitution of the arginine R in position 271,
substitution of the serine S in position 272,
substitution of the threonine T in position 273,
substitution of the valine V in position 274,
substitution of the proline P in position 275,
substitution of the aspartic acid D in position 276,
substitution of the tryptophan W in position 277,
substitution of the threonine T in position 278,
substitution of the methionine M in position 279,
substitution of the threonine T in position 280,
substitution of the leucine L in position 281,
substitution of the isoleucine I in position 282,
substitution of the phenylalanine F in position 283,
substitution of the glutamic acid E in position 284,
substitution of the threonine T in position 296,
substitution of the glutamic acid E in position 298,
of SEQ ID NO: 3 by any other natural or non-natural amino acid.

Because of the deletion of the amino acid in position 2 in SEQ ID NO: 1, the positions of the substitutions of SEQ ID NO: 3 are moved by one position when compared to the positions of SEQ ID NO: 1.

In a more specific embodiment, the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, comprise a single mutation, said mutation being selected from the group consisting of:

substitution of the glycine G in position 8,
substitution of the glycine G in position 9,
substitution of the leucine L in position 28,
substitution of the leucine L in position 47,
substitution of the asparagine N in position 55,
substitution of the leucine L in position 68,
substitution of the threonine T in position 69,
substitution of the isoleucine I in position 73,
substitution of the valine V in position 77,
substitution of the alanine A in position 84,
substitution of the tyrosine Y in position 98,
substitution of the tyrosine Y in position 100,
substitution of the valine V in position 120,
substitution of the isoleucine I in position 123,
substitution of the asparagine N in position 131,
substitution of the aspartic acid D in position 142,
substitution of the aspartic acid D in position 165,
substitution of the isoleucine I in position 168,
substitution of the aspartic acid D in position 192,
substitution of the alanine A in position 194,
substitution of the arginine R in position 224,
substitution of the glycine G in position 226,
substitution of the leucine L in position 227,
substitution of the isoleucine I in position 229,
substitution of the tyrosine Y in position 230,
substitution of the leucine L in position 231,
substitution of the tyrosine Y position 258,
substitution of the cysteine C in position 259,
substitution of the proline P in position 260,
substitution of the threonine T in position 261,
substitution of the isoleucine I in position 262,
substitution of the aspartic acid D in position 263,
substitution of the tryptophane W in position 264,
substitution of the tyrosine Y in position 265,
substitution of the proline P in position 266,
substitution of the proline P in position 267,
substitution of the glutamic acid E in position 268,
substitution of the valine V in position 269,
substitution of the valine V in position 270,
substitution of the arginine R in position 271,
substitution of the serine S in position 272,
substitution of the threonine T in position 273,
substitution of the valine V in position 274,
substitution of the proline P in position 275,
substitution of the aspartic acid D in position 276,
substitution of the tryptophan W in position 277, substitution of the threonine T in position 278,
substitution of the methionine M in position 279,
substitution of the threonine T in position 280,
substitution of the leucine L in position 281,
substitution of the isoleucine I in position 282,
substitution of the phenylalanine F in position 283,
substitution of the glutamic acid E in position 284,
substitution of the threonine T in position 296,
substitution of the glutamic acid E in position 298,
of SEQ ID NO: 3 by any other natural or non-natural amino acid.

In another embodiment, the mutated hyperthermophilic PTEs having a lactonase activity according to the present invention possess a greater phosphotriesterase activity and/or a greater lactonase activity than that of the non-mutated hyperthermophilic PTE having a lactonase activity from which they derived.

The invention relates more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise the at least one mutation selected from the group consisting of:
substitution of the glycine G in position 8,
substitution of the glycine G in position 9,
substitution of the leucine L in position 28,
substitution of the leucine L in position 47,
substitution of the asparagine N in position 55,
substitution of the threonine T in position 69,
substitution of the isoleucine I in position 73,
substitution of the valine V in position 77,
substitution of the alanine A in position 84,
substitution of the tyrosine Y in position 98,
substitution of the tyrosine Y in position 100,
substitution of the valine V in position 120,
substitution of the isoleucine I in position 123,
substitution of the asparagine N in position 131,
substitution of the aspartic acid D in position 142,
substitution of the aspartic acid D in position 165,
substitution of the alanine A in position 194,
substitution of the arginine R in position 224,
substitution of the leucine L in position 227,
substitution of the isoleucine I in position 229,
substitution of the tyrosine Y in position 230,
substitution of the leucine L in position 231,
substitution of the cysteine C in position 259,
substitution of the isoleucine I in position 262,
substitution of the tryptophane W in position 264,
substitution of the proline P in position 275,
substitution of the aspartic acid D in position 276,
substitution of the leucine L in position 281,
substitution of the phenylalanine F in position 283,
substitution of the threonine T in position 296,
substitution of the glutamic acid E in position 298,
of SEQ ID NO: 3 by any other natural or non-natural amino acid.

The invention relates even more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise a single mutation selected from the group consisting of:
substitution of the glycine G in position 8,
substitution of the glycine G in position 9,
substitution of the leucine L in position 28,
substitution of the leucine L in position 47,
substitution of the asparagine N in position 55,
substitution of the threonine T in position 69,
substitution of the isoleucine I in position 73,
substitution of the valine V in position 77,
substitution of the alanine A in position 84,
substitution of the tyrosine Y in position 98,
substitution of the tyrosine Y in position 100,
substitution of the valine V in position 120,
substitution of the isoleucine I in position 123,
substitution of the asparagine N in position 131,
substitution of the aspartic acid D in position 142,
substitution of the aspartic acid D in position 165,
substitution of the alanine A in position 194,
substitution of the arginine R in position 224,
substitution of the leucine L in position 227,
substitution of the isoleucine I in position 229,
substitution of the tyrosine Y in position 230,
substitution of the leucine L in position 231,
substitution of the cysteine C in position 259,
substitution of the isoleucine I in position 262,
substitution of the tryptophane W in position 264,
substitution of the proline P in position 275,
substitution of the aspartic acid D in position 276,
substitution of the leucine L in position 281,
substitution of the phenylalanine F in position 283,
substitution of the threonine T in position 296,
substitution of the glutamic acid E in position 298,
of SEQ ID NO: 3 by any other natural or non-natural amino acid.

The invention relates more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise the at least one mutation selected from the group consisting of:
substitution of the isoleucine I in position 168,
substitution of the aspartic acid D in position 192,
substitution of the tyrosine Y position 258,
substitution of the proline P in position 260,
substitution of the threonine T in position 261,
substitution of the aspartic acid D in position 263,
substitution of the tyrosine Y in position 265,
substitution of the proline P in position 266,
substitution of the proline P in position 267,
substitution of the glutamic acid E in position 268,
substitution of the valine V in position 269,
substitution of the valine V in position 270,
substitution of the arginine R in position 271,
substitution of the serine S in position 272,
substitution of the threonine T in position 273,
substitution of the valine V in position 274,
substitution of the tryptophan W in position 277,
substitution of the threonine T in position 278,
substitution of the threonine T in position 280,
substitution of the isoleucine I in position 282,
substitution of the glutamic acid E in position 284,
of SEQ ID NO: 3 by any other natural or non-natural amino acid.

The invention relates even more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise a single mutation selected from the group consisting of:

substitution of the isoleucine I in position 168,
substitution of the aspartic acid D in position 192,
substitution of the tyrosine Y position 258,
substitution of the proline P in position 260,
substitution of the threonine T in position 261,
substitution of the aspartic acid D in position 263,
substitution of the tyrosine Y in position 265,
substitution of the proline P in position 266,
substitution of the proline P in position 267,
substitution of the glutamic acid E in position 268,
substitution of the valine V in position 269,
substitution of the valine V in position 270,
substitution of the arginine R in position 271,
substitution of the serine S in position 272,
substitution of the threonine T in position 273,
substitution of the valine V in position 274,
substitution of the tryptophan W in position 277,
substitution of the threonine T in position 278,
substitution of the threonine T in position 280,
substitution of the isoleucine I in position 282,
substitution of the glutamic acid E in position 284,
of SEQ ID NO: 3 by any other natural or non-natural amino acid.

The invention relates more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise the at least one mutation selected from the group consisting of:
substitution of the leucine L in position 68,
substitution of the glycine G in position 226,
substitution of the methionine M in position 279,
of SEQ ID NO: 3 by any other natural or non-natural amino acid.

The invention relates even more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, said mutated PTEs comprise a single mutation selected from the group consisting of:
substitution of the leucine L in position 68,
substitution of the glycine G in position 226,
substitution of the methionine M in position 279,
of SEQ ID NO: 3 by any other natural or non-natural amino acid.

The invention relates more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:
substitution of the glycine G in position 8 by a non-bulky amino acid selected from the group consisting of PLIVADCSTN, in particular STA, notably S,
substitution of the glycine G in position 9 by a charged amino acid selected from the group consisting of RKHDEC, in particular EDR, notably E,
substitution of the leucine L in position 28 by a non-bulky amino acid selected from the group consisting of GPIADCSTN or by a hydrophobic amino acid selected from the group consisting of VIMFGAPWYC, in particular GIFA, notably A,
substitution of the leucine L in position 47 by a bulky amino acid selected from the group consisting of EHKRQYWFM, in particular YWF, notably F,
substitution of the asparagine N in position 55 by an bulky amino acid selected from the group consisting of EHKRQYWFM or by a hydrophobic amino acid selected from the group consisting of VILMFGAPWYC, in particular IRL, notably I,
substitution of the threonine T in position 69 by a non-bulky amino acid selected from the group consisting of GPLIVADCSN, in particular VAS, notably S,
substitution of the isoleucine I in position 73 by a hydrophobic amino acid selected from the group consisting of VLMFGAPWYC, in particular CAML, notably L,
substitution of the valine V in position 77 by a non-bulky amino acid selected from the group consisting of GPLIADCSTN, in particular PTI, notably T,
substitution of the alanine A in position 84 by a non-bulky amino acid selected from the group consisting of GPLIVDCSTN or by a hydrophobic amino acid selected from the group consisting of VILMFGPWYC, in particular GIV, notably V,
substitution of the tyrosine Y in position 98 by an bulky amino acid selected from the group consisting of EHKRQWFM or by a hydrophobic amino acid selected from the group consisting of VILMFGAPWC, in particular FCLW, notably W,
substitution of the tyrosine Y in position 100 by an bulky amino acid selected from the group consisting of EHKRQWFM or by a hydrophobic amino acid selected from the group consisting of VILMFGAPWC, in particular GEWF, notably F,
substitution of the valine V in position 120 by a non-bulky amino acid selected from the group consisting of GPLIADCSTN, in particular ILA, notably I,
substitution of the isoleucine I in position 123 by a non-bulky amino acid selected from the group consisting of GPLVADCSTN, in particular LAV, notably L,
substitution of the asparagine N in position 131 by a non-bulky amino acid selected from the group consisting of GPLIVADCST, in particular PST, notably P,
substitution of the aspartic acid D in position 142 by a polar amino acid selected from the group consisting of WYSTCQNRKHE, in particular SET, notably T,
substitution of the aspartic acid D in position 165 by a polar amino acid selected from the group consisting of WYSTCQNRKHE, in particular NQR, notably N,
substitution of the alanine A in position 194 by a non-bulky amino acid selected from the group consisting of GPLIVDCSTN or by a polar amino acid selected from the group consisting of WYSTCNQRKHDE, in particular ST, notably S,
substitution of the arginine R in position 224 by a non-bulky amino acid selected from the group consisting of GPLIVADCSTN or by a polar amino acid selected from the group consisting of WYSTCQNKHDE, in particular CSTAH, notably AC,
substitution of the leucine L in position 227 by a non-bulky amino acid selected from the group consisting of GPIVADCSTN or by apolar amino acid selected from the group consisting of WYSTCQNRKHDE, in particular AIVH, notably V,
substitution of the isoleucine I in position 229 by a non-bulky amino acid selected from the group consisting of GPLVADCSTN or by a hydrophobic amino acid selected from the group consisting of VLMFGAPWYC, in particular LM, notably M, substitution of the tyrosine Y in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVAC-STN, in particular ALMFCITV, notably F, substitution of the proline P in position 275 by a hydrophobic amino acid selected from the group consisting of VILMFGAWYC, in particular LAV, notably L, substitution of the aspartic acid D in position 276 by a hydrophobic amino acid selected from the group consisting of VILMFGAPWYC or by a non-bulky amino acid selected from the group consisting of GPLIVAC-STN, in particular NVMT, notably T, substitution of the leucine L in position 281 by a non-bulky amino acid selected from the group consisting of GPIVADCSTN or by a hydrophobic amino acid selected from the group consisting of VIMFGAPWYC, in particular TMYP, notably T, substitution of the phenylalanine F in position 283 by an bulky amino acid selected from the group consisting of EKHRQYWM, in particular MH, notably M, substitution of the threonine T in position 296 by a non-bulky amino acid selected from the group consisting of GPLIVADCSN, in particular SCL, notably S,
and substitution of the glutamic acid E in position 298 by a polar amino acid selected from the group consisting of WYSTCQNRKHD, in particular QST, notably S.

These 31 particular substitutions in position G8, G9, L28, L47, N55, T69, 173, V77, A84, Y98, Y100, V120, 1123, N131, D142, D165, A194, 8224, L227, 1229, Y230, L231, C259, 1262, W264, P275, D276, L281, F283, T296 and E298 belong to the first set of substitutions called set 1.

These positions, identified by directed evolution strategy, are considered as key positions to modulate enzymatic activities.

By the term "substitution" is meant the replacement of one amino acid by another. The substitutions can be conservative, i.e. the substituted amino acid is replaced by an amino acid of the same structure or with the same physicochemical properties (polar, hydrophobic, acidic, basic amino acids) such that the three dimensional structure of the protein remains unchanged, or by contrast non conservative.

When set 1 is related to a sequence, it means that at least one substitution of said set occurs in said sequence.

The invention relates more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V,
substitution of the aspartic acid D in position 192 by a non-bulky amino acid selected from the group consisting of GPLIVACSTN or by a polar amino acid selected from the group consisting of WYSTCQNRKHE, in particular ST, notably S,
substitution of the tyrosine Y position 258 by a non-bulky amino acid selected from the group consisting of GPLIVADCSTN or by a hydrophobic amino acid selected from the group consisting of VILMFGAPWC, in particular CSVW, notably C,
substitution of the proline P in position 260 a non-bulky amino acid selected from the group consisting of GLIVADCSTN or by a hydrophobic amino acid selected from the group consisting of VILMFGAWYC, in particular SFWV, notably S,
substitution of the threonine T in position 261 a non-bulky amino acid selected from the group consisting of GPLIVADCSN or by a polar amino acid selected from the group consisting of WYSCQNRKHDE, in particular GH, notably G,
substitution of the aspartic acid D in position 263 by a polar amino acid selected from the group consisting of WYSTCQNRKHE or by a non-bulky amino acid selected from the group consisting of GPLIVACSTN, in particular SLH,
substitution of the tyrosine Y in position 265 non-bulky amino acid selected from the group consisting of GPLIVADCSTN or by a hydrophobic amino acid selected from the group consisting of VILMFGAPWC, in particular AVP,
substitution of the proline P in position 266 by a hydrophobic amino acid selected from the group consisting of VILMFGAWYC or by a non-bulky amino acid selected from the group consisting of GPLIVADCSTN, in particular VW, notably V,
substitution of the proline P in position 267 by a polar amino acid selected from the group consisting of WYSTCQNRKHDE, in particular NQ, notably N,
substitution of the glutamic acid E in position 268 by a non-bulky amino acid selected from the group consisting of GPLIVADCSTN or by a hydrophobic amino acid selected from the group consisting of VILMFGAPWYC, in particular IAP, notably IP,
substitution of the valine V in position 269 by a hydrophobic amino acid selected from the group consisting of ILMFGAPWYC, in particular MCL, notably M,
substitution of the valine V in position 270 by a polar amino acid selected from the group consisting of WYSTCQNRKHDE, in particular DEQ, notably D,
substitution of the arginine R in position 271 by a non-bulky amino acid selected from the group consisting of GPLIVADCSTN or by a hydrophobic amino acid selected from the group consisting of VILMFGAPWYC, in particular VAL,
substitution of the serine S in position 272 by an bulky amino acid selected from the group consisting of EHKRQYWFM or by a hydrophobic amino acid selected from the group consisting of VILMFGAPWYC, in particular MLA,
substitution of the threonine T in position 273 by a non-bulky amino acid selected from the group consisting of GPLIVADCSN or by a polar amino acid selected from the group consisting of WYSCQNRKHDE, in particular DEL, notably DL, substitution of the valine V in position 274 by a non-bulky amino acid selected from the group consisting of GPLIADCSTN or by a polar amino acid selected from the group consisting of WYSTCQNRKHD, in particular KRP, substitution of the tryptophane W in position 277 by a polar amino acid selected from the group consisting of YSCQNRKHDE or by a hydrophobic amino acid selected from the group consisting of VILMFGAPYC, in particular KAV, notably K, substitution of the threonine T in position 278 by a polar amino acid selected from the group consisting of WYSCQNRKHDE, in particular DNQ, notably DN, substitution of the threonine T in position 280 by a non-bulky amino acid selected from the group consisting of GPLIVADCSTN or by a polar amino acid selected from the group consisting of WYSCQNRKHDE, in particular GH, substitution of the isoleucine I in position 282 by a non-bulky amino acid selected from the group consisting of GPLVADCSTN or by a hydrophobic amino acid selected from the group consisting of VLMFGAPWYC, in particular ALV, notably AL, and substitution of the glutamic acid E in position 284 non-bulky amino acid selected from the group consisting of GPLIVADCSTN, in particular VAL, notably V, These 21 particular substitutions in position 1168, D192, Y258, P260, T261, D263, Y265, P266, P267, E268, V269, V270, 8271, S272, T273, V274, W277, T278, T280, 1282 and E284 belong to the second set of substitutions called set 2.

These positions were selected by analyzing the evolutive history of this family of enzymes.

When set 2 is related to a sequence, it means that at least one substitution of said set occurs in said sequence.

The invention relates more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

substitution substitution of the leucine L in position 68 by a non-bulky amino acid selected from the group consisting of GPIVADCSTN, in particular GAV, substitution of the glycine G in position 226 by a non-bulky amino acid selected from the group consisting of PLIVADCSTN, in particular AVP, and substitution of the methionine M in position 279 by a hydrophobic amino acid selected from the group consisting of VILFGAPYC or by a charged amino acid selected from the group consisting of RKHDEC, in particular RKDI, notably R.

These 3 particular substitutions in position L68, G226 and M279 belong to the third set of substitutions called set 3.

These positions were selected by analyzing the evolutive history of this family of enzymes.

When set 3 is related to a sequence, it means that at least one substitution of said set occurs in said sequence.

The invention relates even more particularly to the abovementioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

substitution of the glycine G in position 8 by a non-bulky amino acid selected from the group consisting of PLIVADCSTN, in particular STA, notably S, substitution of the glycine G in position 9 by a charged amino acid selected from the group consisting of RKHDEC, in particular EDR, notably E, substitution of the leucine L in position 28 by a non-bulky amino acid selected from the group consisting of GPIADCSTN or by a hydrophobic amino acid selected from the group consisting of VIMFGAPWYC, in particular GIFA, notably A, substitution of the leucine L in position 47 by a bulky amino acid selected from the group consisting of EHKRQYWFM, in particular YWF, notably F, substitution of the asparagine N in position 55 by an bulky amino acid selected from the group consisting of EHKRQYWFM or by a hydrophobic amino acid selected from the group consisting of VILMFGAPWYC, in particular IRL, notably I, substitution of the threonine T in position 69 by a nonbulky amino acid selected from the group consisting of GPLIVADCSN, in particular VAS, notably S, substitution of the isoleucine I in position 73 by a hydrophobic amino acid selected from the group consisting of VLMFGAPWYC, in particular CAML, notably L, substitution of the valine V in position 77 by a non-bulky amino acid selected from the group consisting of GPLIADCSTN, in particular PTI, notably T, substitution of the alanine A in position 84 by a non-bulky amino acid selected from the group consisting of GPLIVDCSTN or by a hydrophobic amino acid selected from the group consisting of VILMFGPWYC, in particular GIV, notably V, substitution of the tyrosine Y in position 98 by an bulky amino acid selected from the group consisting of EHKRQWFM or by a hydrophobic amino acid selected from the group consisting of VILMFGAPWC, in particular FCLW, notably W, substitution of the tyrosine Y in position 100 by an bulky amino acid selected from the group consisting of EHKRQWFM or by a hydrophobic amino acid selected from the group consisting of VILMFGAPWC, in particular GEWF, notably F, substitution of the valine V in position 120 by a non-bulky amino acid selected from the group consisting of GPLIADCSTN, in particular ILA, notably I, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCST, in particular PST, notably P, substitution of the aspartic acid D in position 142 by a polar amino acid selected from the group consisting of WYSTCQNRKHE, in particular SET, notably T, substitution of the aspartic acid D in position 165 by a polar amino acid selected from the group consisting of WYSTCQNRKHE, in particular NQR, notably N, substitution of the alanine A in position 194 by a nonbulky amino acid selected from the group consisting of GPLIVDCSTN or by a polar amino acid selected from the group consisting of WYSTCNQRKHDE, in particular ST, notably S, substitution of the arginine R in position 224 by a nonbulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the isoleucine I in position 229 by a non-bulky amino acid selected from the group consisting of GPLVADCSTN or by a hydrophobic amino acid selected from the group consisting of VLMFGAPWYC, in particular LM, notably M, substitution of the tyrosine Y in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVACSTN, in particular ALMFCITV, notably F, substitution of the proline P in position 275 by a hydrophobic amino acid selected from the group consisting of VILMFGAWYC, in particular LAV, notably L, substitution of the aspartic acid D in position 276 by a hydrophobic amino acid selected from the group consisting of VILMFGAPWYC or by a non-bulky amino acid selected from the group consisting of GPLIVACSTN, in particular NVMT, notably T, substitution of the leucine L in position 281 by a non-bulky amino acid selected from the group consisting of GPIVADCSTN or by a hydrophobic amino acid selected from the group consisting of VIMFGAPWYC, in particular TMYP, notably T, substitution of the phenylalanine F in position 283 by an bulky amino acid selected from the group consisting of EKHRQYWM, in particular MH, notably M, substitution of the threonine T in position 296 by a non-bulky amino acid selected from the group consisting of GPLIVADCSN, in particular SCL, notably S, and substitution of the glutamic acid E in position 298 by a polar amino acid selected from the group consisting of WYSTCQNRKHD, in particular QST, notably S, further comprises at least one mutation selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVACSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VILMFGAPWC, in particular CSVW, notably C, substitution of the proline P in position 260 a non-bulky amino acid selected from the group consisting of GLIVADCSTN or by a hydrophobic amino acid selected from the group consisting of VILMFGAWYC, in particular SFWV, notably S, substitution of the threonine T in position 261 a non-bulky amino acid selected from the group consisting of GPLIVADCSN or by a polar amino acid selected from the group consisting of WYSCQNRKHDE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the tyrosine Y in position 265 non-bulky amino acid selected from the group consisting of GPLIVADCSTN or by a hydrophobic amino acid selected from the group consisting of VILMFGAPWC, in particular AVP, substitution of the proline P in position 266 by a hydrophobic amino acid selected from the group consisting of VILMFGAWYC or by a non-bulky amino acid selected from the group consisting of GPLIVADCSTN, in particular VW, notably V, substitution of the proline P in position 267 by a polar amino acid selected from the group consisting of WYSTCQNRKHDE, in particular NQ, notably N, substitution of the glutamic acid E in position 268 by a non-bulky amino acid selected from the group consisting of GPLIVADCSTN or by a hydrophobic amino acid selected from the group consisting of VILMFGAPWYC, in particular IAP, notably IP, substitution of the valine V in position 269 by a hydrophobic amino acid selected from the group consisting of ILMFGAPWYC, in particular MCL, notably M, substitution of the valine V in position 270 by a polar amino acid selected from the group consisting of WYSTCQNRKHDE, in particular DEQ, notably D, substitution of the arginine R in position 271 by a non-bulky amino acid selected from the group consisting of GPLIVADCSTN or by a hydrophobic amino acid selected from the group consisting of VILMFGAPWYC, in particular VAL, substitution of the serine S in position 272 by an bulky amino acid selected from the group consisting of EHKRQYWFM or by a hydrophobic amino acid selected from the group consisting of VILMFGAPWYC, in particular MLA, substitution of the threonine T in position 273 by a non-bulky amino acid selected from the group consisting of GPLIVADCSN or by a polar amino acid selected from the group consisting of WYSCQNRKHDE, in particular DEL, notably DL, substitution of the valine V in position 274 by a non-bulky amino acid selected from the group consisting of GPLIADCSTN or by a polar amino acid selected from the group consisting of WYSTCQNRKHD, in particular KRP, substitution of the tryptophane W in position 277 by a polar amino acid selected from the group consisting of YSCQNRKHDE or by a hydrophobic amino acid selected from the group consisting of VILMFGAPYC, in particular KAV, notably K, substitution of the threonine T in position 278 by a polar amino acid selected from the group consisting of WYSCQNRKHDE, in particular DNQ, notably DN, substitution of the threonine T in position 280 by a non-bulky amino acid selected from the group consisting of GPLIVADCSTN or by a polar amino acid selected from the group consisting of WYSCQNRKHDE, in particular GH, substitution of the isoleucine I in position 282 by a non-bulky amino acid selected from the group consisting of GPLVADCSTN or by a hydrophobic amino acid selected from the group consisting of VLMFGAPWYC, in particular ALV, notably AL, and substitution of the glutamic acid E in position 284 non-bulky amino acid selected from the group consisting of GPLIVADCSTN, in particular VAL, notably V.

It means that at least one substitution among the 31 particular substitutions of set 1 in position G8, G9, L28, L47, N55, T69, I73, V77, A84, Y98, Y100, V120, I123, N131, D142, D165, A194, S224, L227, I229, Y230, L231, C259, I262, W264, P275, D276, L281, F283, T296 and E298 can be associated with at least one substitution among the 21 particular substitutions of set 2 in position 1168, D192, Y258, P260, T261, D263, Y265, P266, P267, E268, V269, V270, R271, 5272, T273, V274, W277, T278, T280, 1282 and E284.

The invention relates even more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

- substitution of the glycine G in position 8 by a non-bulky amino acid selected from the group consisting of PLIVADCSTN, in particular STA, notably S,
- substitution of the glycine G in position 9 by a charged amino acid selected from the group consisting of RKHDEC, in particular EDR, notably E,
- substitution of the leucine L in position 28 by a non-bulky amino acid selected from the group consisting of GPIADCSTN or by a hydrophobic amino acid selected from the group consisting of VIMFGAPWYC, in particular GIFA, notably A,
- substitution of the leucine L in position 47 by a bulky amino acid selected from the group consisting of EHKRQYWFM, in particular YWF, notably F,
- substitution of the asparagine N in position 55 by an bulky amino acid selected from the group consisting of EHKRQYWFM or by a hydrophobic amino acid selected from the group consisting of VILMFGAPWYC, in particular IRL, notably I,
- substitution of the threonine T in position 69 by a non-bulky amino acid selected from the group consisting of GPLIVADCSN, in particular VAS, notably S,
- substitution of the isoleucine I in position 73 by a hydrophobic amino acid selected from the group consisting of VLMFGAPWYC, in particular CAML, notably L,
- substitution of the valine V in position 77 by a non-bulky amino acid selected from the group consisting of GPLIADCSTN, in particular PTI, notably T,
- substitution of the alanine A in position 84 by a non-bulky amino acid selected from the group consisting of GPLIVDCSTN or by a hydrophobic amino acid selected from the group consisting of VILMFGPWYC, in particular GIV, notably V,
- substitution of the tyrosine Y in position 98 by an bulky amino acid selected from the group consisting of EHKRQWFM or by a hydrophobic amino acid selected from the group consisting of VILMFGAPWC, in particular FCLW, notably W,
- substitution of the tyrosine Y in position 100 by an bulky amino acid selected from the group consisting of EHKRQWFM or by a hydrophobic amino acid selected from the group consisting of VILMFGAPWC, in particular GEWF, notably F,
- substitution of the valine V in position 120 by a non-bulky amino acid selected from the group consisting of GPLIADCSTN, in particular ILA, notably I,
- substitution of the isoleucine I in position 123 by a non-bulky amino acid selected from the group consisting of GPLVADCSTN, in particular LAV, notably L,
- substitution of the asparagine N in position 131 by a non-bulky amino acid selected from the group consisting of GPLIVADCST, in particular PST, notably P,
- substitution of the aspartic acid D in position 142 by a polar amino acid selected from the group consisting of WYSTCQNRKHE, in particular SET, notably T,
- substitution of the aspartic acid D in position 165 by a polar amino acid selected from the group consisting of WYSTCQNRKHE, in particular NQR, notably N,
- substitution of the alanine A in position 194 by a non-bulky amino acid selected from the group consisting of GPLIVDCSTN or by a polar amino acid selected from the group consisting of WYSTCNQRKHDE, in particular ST, notably S,
- substitution of the arginine R in position 224 by a non-bulky amino acid selected from the group consisting of GPLIVADCSTN or by a polar amino acid selected from the group consisting of WYSTCQNKHDE, in particular CSTAH, notably AC,
- substitution of the leucine L in position 227 by a non-bulky amino acid selected from the group consisting of GPIVADCSTN or by apolar amino acid selected from the group consisting of WYSTCQNRKHDE, in particular AIVH, notably V,
- substitution of the isoleucine I in position 229 by a non-bulky amino acid selected from the group consisting of GPLVADCSTN or by a hydrophobic amino acid selected from the group consisting of VLMFGAPWYC, in particular LM, notably M,
- substitution of the tyrosine Y in position 230 by a non-bulky amino acid selected from the group consisting of GPLIVADCSTN, in particular LTAS, notably S,
- substitution of the leucine L in position 231 by a non-bulky amino acid selected from the group consisting of GPIVADCSTN, in particular PVA, notably P,
- substitution of the cysteine C in position 259 by a hydrophobic amino acid selected from the group consisting of VILMFGAPWY, in particular YLIA, notably LA,
- substitution of the isoleucine I in position 262 by a hydrophobic amino acid selected from the group consisting of VLMFGAPWYC, in particular FWC, notably F,
- substitution of the tryptophane W in position 264 by a hydrophobic amino acid selected from the group consisting of VILMFGAPYC or by a non-bulky amino acid selected from the group consisting of GPLIVACSTN, in particular ALMFCITV, notably F,
- substitution of the proline P in position 275 by a hydrophobic amino acid selected from the group consisting of VILMFGAWYC, in particular LAV, notably L, substitution of the aspartic acid D in position 276 by a hydrophobic amino acid selected from the group consisting of VILMFGAPWYC or by a non-bulky amino acid selected from the group consisting of GPLIVACSTN, in particular NVMT, notably T, substitution of the leucine L in position 281 by a non-bulky amino acid selected from the group consisting of GPIVADCSTN or by a hydrophobic amino acid selected from the group consisting of VIMFGAPWYC, in particular TMYP, notably T, substitution of the phenylalanine F in position 283 by an bulky amino acid selected from the group consisting of EKHRQYWM, in particular MH, notably M, substitution of the threonine T in position 296 by a non-bulky amino acid selected from the group consisting of GPLIVADCSN, in particular SCL, notably S, and substitution of the glutamic acid E in position 298 by a polar amino acid selected from the group consisting of WYSTCQNRKHD, in particular QST, notably S, further comprises at least one mutation selected from the group consisting of:

substitution substitution of the leucine L in position 68 by a non-bulky amino acid selected from the group consisting of GPIVADCSTN, in particular GAV, substitution of the glycine G in position 226 by a non-bulky amino acid selected from the group consisting of PLIVADCSTN, in particular AVP, and substitution of the methionine M in position 279 by a hydrophobic amino acid selected from the group consisting of VILFGAPYC or by a charged amino acid selected from the group consisting of RKHDEC, in particular RKDI, notably R.

It means that at least one substitution among the 31 particular substitutions of set 1 in position G8, G9, L28, L47, N55, T69, 173, V77, A84, Y98, Y100, V120, 1123, N131, D142, D165, A194, 8224, L227, 1229, Y230, L231, C259, 1262, W264, P275, D276, L281, F283, T296 and E298 can be associated with at least one substitution among the 3 particular substitutions of set 3 in position L68, G226 and M279.

The invention relates even more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

substitution of the glycine G in position 8 by a non-bulky amino acid selected from the group consisting of PLIVADCSTN, in particular STA, notably S, substitution of the glycine G in position 9 by a charged amino acid selected from the group consisting of RKHDEC, in particular EDR, notably E, substitution of the leucine L in position 28 by a non-bulky amino acid selected from the group consisting of GPIADCSTN or by a hydrophobic amino acid selected from the group consisting of VIMFGAPWYC, in particular GIFA, notably A, substitution of the leucine L in position 47 by a bulky amino acid selected from the group consisting of EHKRQYWFM, in particular YWF, notably F, substitution of the asparagine N in position 55 by an bulky amino acid selected from the group consisting of EHKRQYWFM or by a hydrophobic amino acid selected from the group consisting of VILMFGAPWYC, in particular IRL, notably I, substitution of the threonine T in position 69 by a non-bulky amino acid selected from the group consisting of GPLIVADCSN, in particular VAS, notably S, substitution of the isoleucine I in position 73 by a hydrophobic amino acid selected from the group consisting of VLMFGAPWYC, in particular CAML, notably L, substitution of the valine V in position 77 by a non-bulky amino acid selected from the group consisting of GPLIADCSTN, in particular PTI, notably T, substitution of the alanine A in position 84 by a non-bulky amino acid selected from the group consisting of GPLIVDCSTN or by a hydrophobic amino acid selected from the group consisting of VILMFGPWYC, in particular GIV, notably V, substitution of the tyrosine Y in position 98 by an bulky amino acid selected from the group consisting of EHKRQWFM or by a hydrophobic amino acid selected from the group consisting of VILMFGAPWC, in particular FCLW, notably W, substitution of the tyrosine Y in position 100 by an bulky amino acid selected from the group consisting of EHKRQWFM or by a hydrophobic amino acid selected from the group consisting of VILMFGAPWC, in particular GEWF, notably F, substitution of the valine V in position 120 by a non-bulky amino acid selected from the group consisting of GPLIADCSTN, in particular ILA, notably I, substitution of the isoleucine I in position 123 by a non-bulky amino acid selected from the group consisting of GPLVADCSTN, in particular LAV, notably L, substitution of the asparagine N in position 131 by a non-bulky amino acid selected from the group consisting of GPLIVADCST, in particular PST, notably P, substitution of the aspartic acid D in position 142 by a polar amino acid selected from the group consisting of WYSTCQNRKHE, in particular SET, notably T, substitution of the aspartic acid D in position 165 by a polar amino acid selected from the group consisting of WYSTCQNRKHE, in particular NQR, notably N, substitution of the alanine A in position 194 by a non-bulky amino acid selected from the group consisting of GPLIVDCSTN or by a polar amino acid selected from the group consisting of WYSTCNQRKHDE, in particular ST, notably S, substitution of the arginine R in position 224 by a non-bulky amino acid selected from the group consisting of GPLIVADCSTN or by a polar amino acid selected from the group consisting of WYSTCQNKHDE, in particular CSTAH, notably AC, substitution of the leucine L in position 227 by a non-bulky amino acid selected from the group consisting of GPIVADCSTN or by apolar amino acid selected from the group consisting of WYSTCQNRKHDE, in particular AIVH, notably V, substitution of the isoleucine I in position 229 by a non-bulky amino acid selected from the group consisting of GPLVADCSTN or by a hydrophobic amino acid selected from the group consisting of VLMFGAPWYC, in particular LM, notably M, substitution of the tyrosine Y in position 230 by a non-bulky amino acid selected from the group consisting of GPLIVADCSTN, in particular LTAS, notably S, substitution of the leucine L in position 231 by a non-bulky amino acid selected from the group consisting of GPIVADCSTN, in particular PVA, notably P, substitution of the cysteine C in position 259 by a hydrophobic amino acid selected from the group consisting of VILMFGAPWY, in particular YLIA, notably LA, substitution of the isoleucine I in position 262 by a hydrophobic amino acid selected from the group consisting of VLMFGAPWYC, in particular FWC, notably F, substitution of the tryptophane W in position 264 by a hydrophobic amino acid selected from the group consisting of VILMFGAPYC or by a non-bulky amino acid selected from the group consisting of GPLIVACSTN, in particular ALMFCITV, notably F, substitution of the proline P in position 275 by a hydrophobic amino acid selected from the group consisting of VILMFGAWYC, in particular LAV, notably L, substitution of the aspartic acid D in position 276 by a hydrophobic amino acid selected from the group consisting of VILMFGAPWYC or by a non-bulky amino acid selected from the group consisting of GPLIVACSTN, in particular NVMT, notably T, substitution of the leucine L in position 281 by a non-bulky amino acid selected from the group consisting of GPIVADCSTN or by a hydrophobic amino acid selected from the group consisting of VIMFGAPWYC, in particular TMYP, notably T, substitution of the phenylalanine F in position 283 by an bulky amino acid selected from the group consisting of EKHRQYWM, in particular MH, notably M, substitution of the threonine T in position 296 by a non-bulky amino acid selected from the group consisting of GPLIVADCSN, in particular SCL, notably S, and substitution of the glutamic acid E in position 298 by a polar amino acid selected from the group consisting of WYSTCQNRKHD, in particular QST, notably S, further comprises at least one mutation selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVACSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VILMFGAPWC, in particular CSVW, notably C, substitution of the proline P in position 260 a non-bulky amino acid selected from the group consisting of GLIVADCSTN or by a hydrophobic amino acid selected from the group consisting of VILMFGAWYC, in particular SFWV, notably S, substitution of the threonine T in position 261 a non-bulky amino acid selected from the group consisting of GPLIVADCSN or by a polar amino acid selected from the group consisting of WYSCQNRKHDE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the tyrosine Y in position 265 non-bulky amino acid selected from the group consisting of GPLIVADCSTN or by a hydrophobic amino acid selected from the group consisting of VILMFGAPWC, in particular AVP, substitution of the proline P in position 266 by a hydrophobic amino acid selected from the group consisting of VILMFGAWYC or by a non-bulky amino acid selected from the group consisting of GPLIVADCSTN, in particular VW, notably V, substitution of the proline P in position 267 by a polar amino acid selected from the group consisting of WYSTCQNRKHDE, in particular NQ, notably N, substitution of the glutamic acid E in position 268 by a non-bulky amino acid selected from the group consisting of GPLIVADCSTN or by a hydrophobic amino acid selected from the group consisting of VILMFGAPWYC, in particular IAP, notably IP, substitution of the valine V in position 269 by a hydrophobic amino acid selected from the group consisting of ILMFGAPWYC, in particular MCL, notably M, substitution of the valine V in position 270 by a polar amino acid selected from the group consisting of WYSTCQNRKHDE, in particular DEQ, notably D, substitution of the arginine R in position 271 by a non-bulky amino acid selected from the group consisting of GPLIVADCSTN or by a hydrophobic amino acid selected from the group consisting of VILMFGAPWYC, in particular VAL, substitution of the serine S in position 272 by an bulky amino acid selected from the group consisting of EHKRQYWFM or by a hydrophobic amino acid selected from the group consisting of VILMFGAPWYC, in particular MLA, substitution of the threonine T in position 273 by a non-bulky amino acid selected from the group consisting of GPLIVADCSN or by a polar amino acid selected from the group consisting of WYSCQNRKHDE, in particular DEL, notably DL, substitution of the valine V in position 274 by a non-bulky amino acid selected from the group consisting of GPLIADCSTN or by a polar amino acid selected from the group consisting of WYSTCQNRKHD, in particular KRP, substitution of the tryptophane W in position 277 by a polar amino acid selected from the group consisting of YSCQNRKHDE or by a hydrophobic amino acid selected from the group consisting of VILMFGAPYC, in particular KAV, notably K, substitution of the threonine T in position 278 by a polar amino acid selected from the group consisting of WYSCQNRKHDE, in particular DNQ, notably DN, substitution of the threonine T in position 280 by a non-bulky amino acid selected from the group consisting of GPLIVADCSTN or by a polar amino acid selected from the group consisting of WYSCQNRKHDE, in particular GH, substitution of the isoleucine I in position 282 by a non-bulky amino acid selected from the group consisting of GPLVADCSTN or by a hydrophobic amino acid selected from the group consisting of VLMFGAPWYC, in particular ALV, notably AL, and substitution of the glutamic acid E in position 284 non-bulky amino acid selected from the group consisting of GPLIVADCSTN, in particular VAL, notably V, further comprises at least one mutation selected from the group consisting of:

substitution substitution of the leucine L in position 68 by a non-bulky amino acid selected from the group consisting of GPIVADCSTN, in particular GAV, substitution of the glycine G in position 226 by a non-bulky amino acid selected from the group consisting of PLIVADCSTN, in particular AVP, and substitution of the methionine M in position 279 by a hydrophobic amino acid selected from the group consisting of VILFGAPYC or by a charged amino acid selected from the group consisting of RKHDEC, in particular RKDI, notably R.

It means that at least one substitution among the 31 particular substitutions of set 1 in position G8, G9, L28, L47, N55, T69, I73, V77, A84, Y98, Y100, V120, I123, N131, D142, D165, A194, 8224, L227, I229, Y230, L231, C259, I262, W264, P275, D276, L281, F283, T296 and E298 can be associated with at least one substitution among the 21 particular substitutions of set 2 in position I168, D192, Y258, P260, T261, D263, Y265, P266, P267, E268, V269, V270, R271, S272, T273, V274, W277, T278, T280, I282 and E284 and with at least one substitution among the 3 particular substitutions of set 3 in position L68, G226 and M279.

The invention relates even more particularly to the above-mentioned mutated hyperthermophilic PTEs having a lactonase activity according to the present invention, corresponding to the sequence of SEQ ID NO: 3 or having at least 70% or more identity to the amino acid sequence of SEQ ID NO: 3, and wherein the at least one mutation is selected from the group consisting of:

substitution of the isoleucine I in position 168 by a non-bulky amino acid selected from the group consisting of GPLVADCSTN or by a hydrophobic amino acid selected from the group consisting of VLMFGAPWYC, in particular VAL, notably V, substitution of the aspartic acid D in position 192 by a non-bulky amino acid selected from the group consisting of GPLIVACSTN or by a polar amino acid selected from the group consisting of WYSTCQNRKHE, in particular ST, notably S, substitution of the tyrosine Y position 258 by a non-bulky amino acid selected from the group consisting of GPLIVADCSTN or by a hydrophobic amino acid selected from the group consisting of VILMFGAPWC, in particular CSVW, notably C, substitution of the proline P in position 260 a non-bulky amino acid selected from the group consisting of GLIVADCSTN or by a hydrophobic amino acid selected from the group consisting of VILMFGAWYC, in particular SFWV, notably S, substitution of the threonine T in position 261 a non-bulky amino acid selected from the group consisting of GPLIVADCSN or by a polar amino acid selected from the group consisting of WYSCQNRKHDE, in particular GH, notably G, substitution of the aspartic acid D in position 263 by a polar amino acid selected from the group consisting of WYSTCQNRKHE or by a non-bulky amino acid selected from the group consisting of GPLIVACSTN, in particular SLH, substitution of the tyrosine Y in position 265 non-bulky amino acid selected from the group consisting of GPLIVADCSTN or by a hydrophobic amino acid selected from the group consisting of VILMFGAPWC, in particular AVP, substitution of the proline P in position 266 by a hydrophobic amino acid selected from the group consisting of VILMFGAWYC or by a non-bulky amino acid selected from the group consisting of GPLIVADCSTN, in particular VW, notably V, substitution of the proline P in position 267 by a polar amino acid selected from the group consisting of WYSTCQNRKHDE, in particular NQ, notably N, substitution of the glutamic acid E in position 268 by a non-bulky amino acid selected from the group consisting of GPLIVADCSTN or by a hydrophobic amino acid selected from the group consisting of VILMFGAPWYC, in particular IAP, notably IP, substitution of the valine V in position 269 by a hydrophobic amino acid selected from the group consisting of ILMFGAPWYC, in particular MCL, notably M, substitution of the valine V in position 270 by a polar amino acid selected from the group consisting of WYSTCQNRKHDE, in particular DEQ, notably D, substitution of the arginine R in position 271 by a non-bulky amino acid selected from the group consisting of GPLIVADCSTN or by a hydrophobic amino acid selected from the group consisting of VILMFGAPWYC, in particular VAL, substitution of the serine S in position 272 by an bulky amino acid selected from the group consisting of EHKRQYWFM or by a hydrophobic amino acid selected from the group consisting of VILMFGAPWYC, in particular MLA, substitution of the threonine T in position 273 by a non-bulky amino acid selected from the group consisting of GPLIVADCSN or by a polar amino acid selected from the group consisting of WYSCQNRKHDE, in particular DEL, notably DL, substitution of the valine V in position 274 by a non-bulky amino acid selected from the group consisting of GPLIADCSTN or by a polar amino acid selected from the group consisting of WYSTCQNRKHD, in particular KRP, substitution of the tryptophane W in position 277 by a polar amino acid selected from the group consisting of YSCQNRKHDE or by a hydrophobic amino acid selected from the group consisting of VILMFGAPYC, in particular KAV, notably K, substitution of the threonine T in position 278 by a polar amino acid selected from the group consisting of WYSCQNRKHDE, in particular DNQ, notably DN, substitution of the threonine T in position 280 by a non-bulky amino acid selected from the group consisting of GPLIVADCSTN or by a polar amino acid selected from the group consisting of WYSCQNRKHDE, in particular GH, substitution of the isoleucine I in position 282 by a non-bulky amino acid selected from the group consisting of GPLVADCSTN or by a hydrophobic amino acid selected from the group consisting of VLMFGAPWYC, in particular ALV, notably AL, and substitution of the glutamic acid E in position 284 non-bulky amino acid selected from the group consisting of GPLIVADCSTN, in particular VAL, notably V, further comprises at least one mutation selected from the group consisting of:

substitution substitution of the leucine L in position 68 by a non-bulky amino acid selected from the group consisting of GPIVADCSTN, in particular GAV, substitution of the glycine G in position 226 by a non-bulky amino acid selected from the group consisting of PLIVADCSTN, in particular AVP, and substitution of the methionine M in position 279 by a hydrophobic amino acid selected from the group consisting of VILFGAPYC or by a charged amino acid selected from the group consisting of RKHDEC, in particular RKDI, notably R.

It means that at least one substitution among the 21 particular substitutions of set 2 in position I168, D192, Y258, P260, T261, D263, Y265, P266, P267, E268, V269, V270, 8271, S272, T273, V274, W277, T278, T280, I282 and E284 can be associated with at least one substitution among the 3 particular substitutions of set 3 in position L68, G226 and M279.

A more particular subject of the invention is mutated hyperthermophilic PTEs having a lactonase activity according to the present invention, derived from the hyperthermophilic Lactonase of *Vulcanisaeta moutnovskia* corresponding to the sequence of SEQ ID NO: 3, said mutated hyperthermophilic PTEs correspond to the following sequences:

SEQ ID NO: 5 corresponding to the SEQ ID NO: 3 comprising the following one mutation:
  substitution of the tryptophan W in position 264 by a phenylalanine F,
SEQ ID NO: 7 corresponding to the SEQ ID NO: 3 comprising the following one mutation:
  substitution of the tryptophan W in position 264 by a methionine M,
SEQ ID NO: 9 corresponding to the SEQ ID NO: 3 comprising the following one mutation:
  substitution of the tryptophan W in position 264 by a leucine L,
SEQ ID NO: 11 corresponding to the SEQ ID NO: 3 comprising the following one mutation:
  substitution of the tryptophan W in position 264 by an alanine A,
SEQ ID NO: 13 corresponding to the SEQ ID NO: 3 comprising the following one mutation:
  substitution of the tryptophan W in position 264 by an isoleucine I,
SEQ ID NO: 15 corresponding to the SEQ ID NO: 3 comprising the following one mutation:
  substitution of the tryptophan W in position 264 by a valine V,
SEQ ID NO: 17 corresponding to the SEQ ID NO: 3 comprising the following one mutation:
  substitution of the tryptophan W in position 264 by a threonine T,
SEQ ID NO: 19 corresponding to the SEQ ID NO: 3 comprising the following one mutation:
  substitution of the tryptophan W in position 264 by a cysteine C,
SEQ ID NO: 21 corresponding to the SEQ ID NO: 3 comprising the following three mutations:
  substitution of the cysteine C in position 259 by a leucine L,
  substitution of the isoleucine I in position 262 by a phenylalanine F,
  substitution of the tryptophan W in position 264 by an alanine A,
SEQ ID NO: 23 corresponding to the SEQ ID NO: 3 comprising the following four mutations:
  substitution of the leucine L in position 28 by an alanine A,
  substitution of the tyrosine Y in position 98 by a tryptophan W,
  substitution of the isoleucine I in position 229 by a methionine M,
  substitution of the tryptophan W in position 264 by a methionine M,
SEQ ID NO: 25 corresponding to the SEQ ID NO: 3 comprising the following four mutations:
  substitution of the leucine L in position 28 by an alanine A,
  substitution of the tyrosine Y in position 98 by a tryptophan W,
  substitution of the tryptophan W in position 264 by a leucine L,
  substitution of the methionine M in position 279 by a threonine T,
SEQ ID NO: 27 corresponding to the SEQ ID NO: 3 comprising the following four mutations:
  substitution of the cytosine C in position 259 by an alanine A,
  substitution of the tryptophan W in position 264 by a methionine M,
  substitution of the methionine M in position 279 by a threonine T,
SEQ ID NO: 29 corresponding to the SEQ ID NO: 3 comprising the following six mutations:
  substitution of the leucine L in position 28 by an alanine A,
  substitution of the valine V in position 77 by a threonine T,
  substitution of the tyrosine Y in position 98 by a tryptophan W,
  substitution of the tyrosine Y in position 100 by a phenylalanine F,
  substitution of the asparagine N in position 131 by a proline P,
  substitution of the leucine L in position 227 by a valine V,
SEQ ID NO: 31 corresponding to the SEQ ID NO: 3 comprising the following six mutations:
  substitution of the tyrosine Y in position 100 by a phenylalanine F,
  substitution of the isoleucine I in position 123 by a leucine L,
  substitution of the isoleucine I in position 229 by a methionine M,
  substitution of the tyrosine Y in position 230 by a serine S,
  substitution of the tryptophan W in position 264 by a leucine L,
SEQ ID NO: 33 corresponding to the SEQ ID NO: 3 comprising the following seven mutations:
  substitution of the threonine T in position 69 by a serine S,
  substitution of the asparagine N in position 131 by a proline P,
  substitution of the isoleucine I in position 229 by a methionine M,
  substitution of the tyrosine Y in position 230 by a serine S,
  substitution of the tryptophan W in position 264 by a methionine M,
  substitution of the threonine T in position 273 by a proline P,
SEQ ID NO: 35 corresponding to the SEQ ID NO: 3 comprising the following six mutations:
  substitution of the threonine T in position 69 by a serine S,
  substitution of the valine V in position 77 by a threonine T, substitution of the tyrosine Y in position 98 by a tryptophan W,
substitution of the tyrosine Y in position 100 by a phenylalanine F,
substitution of the isoleucine I in position 229 by a methionine M,
substitution of the tryptophan W in position 264 by a leucine L, SEQ ID NO: 37 corresponding to the SEQ ID NO: 3 comprising the following five mutations:
substitution of the glycine G in position 9 by a glutamic acid E,
substitution of the tyrosine Y in position 98 by a tryptophan W,
substitution of the tyrosine Y in position 100 by a phenylalanine F,
substitution of the isoleucine I in position 229 by a methionine M, SEQ ID NO: 39 corresponding to the SEQ ID NO: 3 comprising the following two mutations:
substitution of the tryptophan W in position 264 by a phenylalanine F, SEQ ID NO: 41 corresponding to the SEQ ID NO: 3 comprising the following five mutations:
substitution of the threonine T in position 69 by a serine S,
substitution of the tyrosine Y in position 98 by a tryptophan W,
substitution of the tyrosine Y in position 100 by a phenylalanine F,
substitution of the asparagine N in position 131 by a proline P,
substitution of the isoleucine I in position 229 by a methionine M, SEQ ID NO: 43 corresponding to the SEQ ID NO: 3 comprising the following four mutations:
substitution of the leucine L in position 28 by an alanine A,
substitution of the leucine L in position 227 by a valine V,
substitution the tryptophan W in position 264 by a leucine L, SEQ ID NO: 45 corresponding to the SEQ ID NO: 3 comprising the following eight mutations:
substitution of the leucine L in position 68 by a valine V,
substitution of the threonine T in position 69 by a serine S,
substitution of the tyrosine Y in position 98 by a tryptophan W,
substitution of the tyrosine Y in position 100 by a phenylalanine F,
substitution of the isoleucine I in position 229 by a methionine M,
substitution of the cysteine C in position 259 by an alanine A,
substitution the tryptophan W in position 264 by a leucine L,
substitution of the methionine M in position 279 by a threonine T, SEQ ID NO: 47 corresponding to the SEQ ID NO: 3 comprising the following eight mutations:
substitution of the threonine T in position 69 by a serine S,
substitution of the tyrosine Y in position 98 by a tryptophan W,
substitution of the tyrosine Y in position 100 by a phenylalanine F,
substitution of the asparagine N in position 131 by a proline P,
substitution of the aspartic acid D in position 165 by an asparagine N,
substitution of the leucine L in position 227 by a valine V,
substitution the tryptophan W in position 264 by a methionine M, SEQ ID NO: 49 corresponding to the SEQ ID NO: 3 comprising the following five mutations:
substitution of the threonine T in position 69 by a serine S,
substitution of the tyrosine Y in position 98 by a tryptophan W,
substitution of the tyrosine Y in position 100 by a phenylalanine F,
substitution of the asparagine N in position 131 by a proline P, SEQ ID NO: 51 corresponding to the SEQ ID NO: 3 comprising the following five mutations:
substitution of the leucine L in position 28 by an alanine A,
substitution of the tyrosine Y in position 98 by a tryptophan W,
substitution of the tyrosine Y in position 100 by a phenylalanine F,
substitution of the leucine L in position 227 by a valine V, SEQ ID NO: 53 corresponding to the SEQ ID NO: 3 comprising the following five mutations:
substitution of the threonine T in position 69 by a serine S,
substitution of the tyrosine Y in position 98 by a tryptophan W,
substitution of the tyrosine Y in position 100 by a phenylalanine F,
substitution of the asparagine N in position 131 by a proline P,
substitution of the isoleucine I in position 229 by a methionine M, SEQ ID NO: 55 corresponding to the SEQ ID NO: 3 comprising the following five mutations:
substitution of the leucine L in position 28 by an alanine A,
substitution of the threonine T in position 69 by a serine S,
substitution of the tyrosine Y in position 98 by a tryptophan W,
substitution the tryptophan W in position 264 by a leucine L, SEQ ID NO: 57 corresponding to the SEQ ID NO: 3 comprising the following five mutations:
substitution the tryptophan W in position 264 by a cysteine C,
substitution of the leucine L in position 281 by a methionine M, SEQ ID NO: 59 corresponding to the SEQ ID NO: 3 comprising the following five mutations:
substitution of the valine V in position 274 by a threonine T, SEQ ID NO: 61 corresponding to the SEQ ID NO: 3 comprising the following five mutations:
substitution of the threonine T in position 273 by a proline P, SEQ ID NO: 63 corresponding to the SEQ ID NO: 3 comprising the following five mutations:
  substitution of the valine V in position 120 by an isoleucine I,
  substitution of the leucine L in position 231 by a proline P,
  substitution of the threonine T in position 296 by a serine S,
SEQ ID NO: 65 corresponding to the SEQ ID NO: 3 comprising the following five mutations:
  substitution of the valine V in position 120 by an isoleucine I,
SEQ ID NO: 67 corresponding to the SEQ ID NO: 3 comprising the following five mutations:
  substitution of the tyrosine Y in position 98 by a tryptophan W,
SEQ ID NO: 69 corresponding to the SEQ ID NO: 3 comprising the following five mutations:
  substitution of the leucine L in position 28 by an alanine A,
  substitution of the tyrosine Y in position 100 by a phenylalanine F,
  substitution the tryptophan W in position 264 by a leucine L.

The coding sequence of the above-mentioned mutated hyperthermophilic PTE having a lactonase activity according to the present invention, derived from the hyperthermophilic lactonase of *Vulcanisaeta moutnovskia* corresponding to the sequence SEQ ID NO: 3 and corresponding to the following sequences SEQ ID NO: 4, 6, 8, 10, 12, 14, 16, 18, 20, 22, 24, 26, 28, 30, 32, 34, 36, 38, 40, 42, 44, 46, 48, 50, 52, 54, 56, 58, 60, 62, 64, 66, and 68 are also part of the invention.

The invention also related to mutated hyperthermophilic PTE having a lactonase activity according to the present invention, derived from the hyperthermophilic lactonase of *Vulcanisaeta moutnovskia* corresponding to the sequence SEQ ID NO: 3, said mutated hyperthermophilic PTE correspond to the following sequences SEQ ID NO: 75, 77, 79, 81, 83, 85, 87, 89, 91, 93, 95, 97, 99, 101, 103, 105, 107, 109, 111, 113, 115, 117, 119, 121, 123, 125, 127, 129, 131, 133 and 135 for the proteins and to their respective coding sequences SEQ ID NO: 70, 72, 74, 76, 78, 80, 82, 84, 86, 88, 90, 92, 94, 96, 98, 100, 102, 104, 106, 108, 110, 112, 114, 116, 118, 120, 122, 124, 126, 128, 130, 132 and 134.

In an embodiment, the invention relates to a mutated hyperthermophilic phosphotriesterase (PTE) having a lactonase activity derived from a hyperthermophilic PTE corresponding to the sequence of SEQ ID NO: 1 or having at least 70% identity to the amino acid sequence of SEQ ID NO: 1,
said mutated PTE comprising at least one mutation selected from the group consisting of:
  substitution of the valine L in position 29,
  substitution of the tyrosine Y in position 99,
  substitution of the tyrosine Y in position 101,
  substitution of the arginine R in position 225,
  substitution of the tryptophane W in position 265,
of SEQ ID NO: 1 by any other natural or non-natural amino acid.

In an embodiment, the invention relates to a mutated hyperthermophilic phosphotriesterase (PTE) having a lactonase activity derived by mutation from a hyperthermophilic PTE corresponding to the sequence of SEQ ID NO: 1 or having at least 70% identity to the amino acid sequence of SEQ ID NO: 1,
said mutation being at least one mutation selected from the group consisting of:
  substitution of the valine L in position 29,
  substitution of the tyrosine Y in position 99,
  substitution of the tyrosine Y in position 101,
  substitution of the arginine R in position 225,
  substitution of the tryptophane W in position 265,
of SEQ ID NO: 1 by any other natural or non-natural amino acid.

In a particular embodiment, the invention relates to the mutated hyperthermophilic PTE having a lactonase activity as defined above, said mutated hyperthermophilic PTE being derived from a hyperthermophilic PTE of *Vulcanisaeta moutnovskia* corresponding to the sequence of SEQ ID NO: 3 or having at least 70% identity to the amino acid sequence of SEQ ID NO: 3,
said SEQ ID NO: 3 corresponding to SEQ ID NO: 1 in which the amino acid in position 2 is missing,
said mutated PTE comprising at least one mutation selected from the group consisting of:
  substitution of the valine L in position 28,
  substitution of the tyrosine Y in position 98,
  substitution of the tyrosine Y in position 100,
  substitution of the arginine R in position 224,
  substitution of the tryptophane W in position 264,
of SEQ ID NO: 3 by any other natural or non-natural amino acid.

In a particular embodiment, the invention relates to the mutated hyperthermophilic PTE having a lactonase activity as defined above, said mutated PTE comprising at least one mutation being:
  a substitution of the valine L in position 28, and/or
  a substitution of the tyrosine Y in position 100, and/or
  a substitution of the arginine R in position 224, and/or
  a substitution of the tryptophane W in position 264,
of SEQ ID NO: 3 by any other natural or non-natural amino acid.

In a particular embodiment, the invention relates to the mutated hyperthermophilic PTE having a lactonase activity as defined above, said mutated PTE having at least 70% identity, preferably at least 75%, 80%, 85%, 90% or 95% identity to the amino acid sequence SEQ ID NO: 3.

In a particular embodiment, the invention relates to the mutated hyperthermophilic PTE having a lactonase activity as defined above, wherein said mutated hyperthermophilic PTE having a lactonase activity possesses:
  a greater phosphotriesterase activity, and/or
  a greater lactonase activity,
  than that of the non-mutated hyperthermophilic PTE having a lactonase activity from which they derived.

In a particular embodiment, the invention relates to the mutated hyperthermophilic PTE having a lactonase activity as defined above, wherein said mutated hyperthermophilic PTE having a lactonase activity possesses a greater phosphotriesterase activity than that of the non-mutated hyperthermophilic PTE having a lactonase activity from which they derived.

In a particular embodiment, the invention relates to the mutated hyperthermophilic PTE having a lactonase activity as defined above, wherein said mutated hyperthermophilic PTE having a lactonase activity possesses a greater lactonase activity than that of the non-mutated hyperthermophilic PTE having a lactonase activity from which they derived.

In a particular embodiment, the invention relates to the mutated hyperthermophilic PTE having a lactonase activity as defined above, wherein the at least one mutation is selected from the group consisting of:

substitution of the leucine L in position 28 by a non-bulky amino acid selected from the group consisting of GPIADCSTN or by a hydrophobic amino acid selected from the group consisting of VIMFGAPWYC, substitution of the tyrosine Y in position 98 by a bulky amino acid selected from the group consisting of EHKRQWFM or by a hydrophobic amino acid selected from the group consisting of VILMFGAPWC, substitution of the tyrosine Y in position 100 by a bulky amino acid selected from the group consisting of EHKRQWFM or by a hydrophobic amino acid selected from the group consisting of VILMFGAPWC, substitution of the arginine R in position 224 by a non-bulky amino acid selected from the group consisting of GPLIVADCSTN or by a polar amino acid selected from the group consisting of WYSTCQNKHDE, substitution of the tryptophane W in position 264 by a hydrophobic amino acid selected from the group consisting of VILMFGAPYC or by a non-bulky amino acid selected from the group consisting of GPLIVACSTN.

In a particular embodiment, the invention relates to the mutated hyperthermophilic PTE having a lactonase activity as defined above, wherein the at least one mutation is selected from the group consisting of:

substitution of the leucine L in position 28 by an amino acid selected from the group consisting of AGV, substitution of the tyrosine Y in position 100 by an amino acid E, substitution of the arginine R in position 224 by an amino acid Q, substitution of the tryptophane W in position 264 by an amino acid selected from the group consisting of ACGIMNPQRSTVYDEHKLF.

In a particular embodiment, the invention relates to the mutated hyperthermophilic PTE having a lactonase activity as defined above, wherein the at least one mutation is selected from the group consisting of:

substitution of the leucine L in position 28 by an amino acid selected from the group consisting of AGV, substitution of the tryptophane W in position 264 by an amino acid selected from the group consisting of ACGIMNPQSTVY.

In a particular embodiment, the invention relates to the mutated hyperthermophilic PTE having a lactonase activity as defined above, wherein the at least one mutation is selected from the group consisting of:

substitution of the leucine L in position 28 by an amino acid selected from the group consisting of AG, substitution of the tyrosine Y in position 100 by an amino acid E, substitution of the arginine R in position 224 by an amino acid Q, substitution of the tryptophane W in position 264 by an amino acid selected from the group consisting of ADEGHIKLMNQRSTVYF.

In a particular embodiment, the invention relates to the mutated hyperthermophilic PTE having a lactonase activity as defined above, wherein the at least one mutation is selected from the group consisting of:

substitution of the leucine L in position 28 by an amino acid selected from the group consisting of AG, substitution of the tryptophane W in position 264 by an amino acid selected from the group consisting of AGIMNQSTVY.

In a particular embodiment, the invention relates to the mutated hyperthermophilic PTE having a lactonase activity as defined above, wherein the at least one mutation is a single substitution of the leucine L in position 28 by an amino acid selected from the group consisting of ACGIMNPQRSTVYDEHKWF, in particular AGV.

In a particular embodiment, the invention relates to the mutated hyperthermophilic PTE having a lactonase activity as defined above, wherein the at least one mutation is a single substitution of the tyrosine Y in position 98 by an amino acid selected from the group consisting of ACGIMNPQRSTVWDEHKLF.

In a particular embodiment, the invention relates to the mutated hyperthermophilic PTE having a lactonase activity as defined above, wherein the at least one mutation is a single substitution of the tyrosine Y in position 100 by an amino acid selected from the group consisting of ACGIMNPQRSTVWDEHKLF, in particular E.

In a particular embodiment, the invention relates to the mutated hyperthermophilic PTE having a lactonase activity as defined above, wherein the at least one mutation is a single substitution of the arginine R in position 224 by an amino acid selected from the group consisting of ACGIMNPQWSTVYDEHKLF, in particular Q.

In a particular embodiment, the invention relates to the mutated hyperthermophilic PTE having a lactonase activity as defined above, wherein the at least one mutation is a single substitution of the tryptophane W in position 264 by an amino acid selected from the group consisting of ACGIMNPQRSTVYDEHKLF.

In a particular embodiment, the at least one mutation is a single substitution of the W in position 264 by A.

In a particular embodiment, the at least one mutation is a single substitution of the W in position 264 by C.

In a particular embodiment, the at least one mutation is a single substitution of the W in position 264 by G.

In a particular embodiment, the at least one mutation is a single substitution of the W in position 264 by I.

In a particular embodiment, the at least one mutation is a single substitution of the W in position 264 by M.

In a particular embodiment, the at least one mutation is a single substitution of the W in position 264 by N.

In a particular embodiment, the at least one mutation is a single substitution of the W in position 264 by P.

In a particular embodiment, the at least one mutation is a single substitution of the W in position 264 by Q.

In a particular embodiment, the at least one mutation is a single substitution of the W in position 264 by R.

In a particular embodiment, the at least one mutation is a single substitution of the W in position 264 by S.

In a particular embodiment, the at least one mutation is a single substitution of the W in position 264 by T.

In a particular embodiment, the at least one mutation is a single substitution of the W in position 264 by V.

In a particular embodiment, the at least one mutation is a single substitution of the W in position 264 by Y.

In a particular embodiment, the at least one mutation is a single substitution of the W in position 264 by D.

In a particular embodiment, the at least one mutation is a single substitution of the W in position 264 by E.

In a particular embodiment, the at least one mutation is a single substitution of the W in position 264 by H.

In a particular embodiment, the at least one mutation is a single substitution of the W in position 264 by K.

In a particular embodiment, the at least one mutation is a single substitution of the W in position 264 by L.

In a particular embodiment, the at least one mutation is a single substitution of the W in position 264 by F.

In a particular embodiment, the invention relates to the mutated hyperthermophilic PTE having a lactonase activity as defined above, said mutated hyperthermophilic PTE being chosen among the group consisting of the following sequences: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206 and SEQ ID NO: 207.

The invention also relates to the isolated nucleic acid sequence encoding the mutated hyperthermophilic PTE having a lactonase activity as defined above.

A subject of the invention is also the vectors comprising the nucleic acid encoding the mutated hyperthermophilic PTE having a lactonase activity as defined above. Such vectors can be plasmids, cosmids, phagemids or any other tool useful for cloning and expressing a nucleic acid.

The invention also relates to host cells, in particular bacteria, transformed by using the vector as defined above, such that their genome contains nucleotide sequences encoding the mutated hyperthermophilic PTE having a lactonase activity as defined above, said mutated hyperthermophilic PTE having a lactonase activity being produced in the cytoplasm of the host cells or secreted at their surface.

A subject of the invention is also is a method for generating a library of mutated hyperthermophilic PTE variants having a lactonase activity comprising:
  introducing into a population of host cells of a plurality of vectors comprising a nucleic acid sequence encoding the mutated hyperthermophilic PTE having a lactonase activity,
  culturing the population of host cells in an appropriate culture media,
  expressing the polypeptide in the said cultured host cell,
  recovering a plurality of mutated hyperthermophilic PTE variants.

The invention also relates to a library of mutated hyperthermophilic PTE variants having a lactonase activity obtainable by the method for generating a library of mutated hyperthermophilic PTE variants having a lactonase activity as disclosed above.

The aim of said library is to provide polypeptide variants of mutated hyperthermophilic PTE having a lactonase activity with enhanced phenotypic properties relative to those of the wild-type hyperthermophilic PTE having a lactonase activity from which they derived.

The invention also relates to compositions comprising the mutated hyperthermophilic PTE having a lactonase activity as defined above.

In a preferred embodiment, the compositions as defined above comprising the mutated hyperthermophilic PTE having a lactonase activity further comprise at least one detergent.

In a more preferred embodiment, the above mentioned composition comprising both the mutated hyperthermophilic PTE having a lactonase activity and at least one detergent can be used as laundry detergent to clean up materials impregnated with OPs compounds.

The invention also relates to the use of a mutated hyperthermophilic PTE having a lactonase activity as defined above, or of host cells as defined above, as bioscavengers:
  within the context of the decontamination of the surfaces of materials, of the skin or mucous membranes contaminated with organophosphorus compounds, or
  within the context of the prevention or treatment of an external or of an internal poisoning by ingestion or inhalation of organophosphorous compounds,
  within the context of the pollution control of water polluted with organophosphorus compounds, or
  within the context of the destruction of stocks of neurotoxic agents.

A subject of the invention is also materials impregnated with mutated hyperthermophilic PTE having a lactonase activity as defined above, in liquid or solid form, such as gloves, strips, plasters, bandages, stupes, various garments, wipes, spray foams.

The mutated hyperthermophilic PTE having a lactonase activity as defined in the invention can also be added to painting media in order to limit the formation of biofilms, notably in boats or other sea equipments.

The mutated hyperthermophilic PTE having a lactonase activity as defined in the invention can also be used to inhibit the fire blight in plants.

Another subject of the invention is kits of decontamination of the surfaces of the materials, of the skins or mucous membranes, contaminated with organophosphorus compounds, or for the pollution control of water polluted with organophosphorus compounds, said kit comprising mutated hyperthermophilic PTE having a lactonase activity as defined above, or materials impregnated with mutated hyperthermophilic PTE having a lactonase activity as defined above.

A subject of the invention is also bioscavengers of organophosphorus compounds comprising mutated hyperthermophilic PTE having a lactonase activity as defined above.

The invention also related to cartridges for external decontamination inside which mutated hyperthermophilic PTE having a lactonase activity as defined above are grafted. Said cartridges can be used for decontaminating the waters poisoned with OPs compounds. Said cartridges can also be used for decontaminating the blood of an individual poisoned with OPs compounds.

The invention also related to pharmaceutical compositions comprising as active ingredient at least one mutated hyperthermophilic PTE having a lactonase activity as defined above in combination with a pharmaceutically acceptable vehicle.

The invention also relates to a composition comprising as active ingredient at least one mutated hyperthermophilic PTE having a lactonase activity as defined above for its use as a medicament.

The invention also relates to pharmaceutical compositions for their use in the treatment of pathology due to the presence of bacteria, notably pneumonia or nosocomial diseases.

The invention also relates to pharmaceutical compositions for their use in the treatment of dental plaque.

The invention also relates to pharmaceutical compositions for their use as eye drops in the treatment of eye infections or eye surface healing.

The invention also relates to pharmaceutical compositions for grafting medical device. By the term "grafting", is meant that mutated hyperthermophilic PTE having a lactonase activity of pharmaceutical compositions are covalently linked to medical device. By the term "medical device" is meant not only simple device such as for example tongue depressors, bedpans, medical thermometer, disposable gloves or surgical instruments, but also implantable medical device such as for example prosthesis, implants, pacemakers or insulin pumps.

In a preferred embodiment, pharmaceutical compositions as defined above comprising the mutated hyperthermophilic PTE having a lactonase activity further comprise at least one antibiotic selected from the group consisting of gentamycine, ciprofloxacin, ceftazidime, imipenem, tobramycine.

In a more preferred embodiment, pharmaceutical compositions as defined above are presented in a form which can be administered by injectable route, in particular in solution or packaged or pegylated, or by topical route, in particular in the form of an ointment, aerosol or wipes.

The invention also related to use of materials impregnated according with comprising the mutated hyperthermophilic PTE having a lactonase activity, as antiseptics for the decontamination of the surface bacterial infection.

The invention also relates to composition or pharmaceutical composition comprising the mutated hyperthermophilic PTE having a lactonase activity for its use in the treatment of bacterial infections caused by bacteria using homoserin lactone substrates to communicate, in particular in the blood, wounds, burn, skin, biomaterial-body contact area.

The invention also relates to composition or pharmaceutical composition comprising the mutated hyperthermophilic PTE having a lactonase activity for its use in the treatment of eyes infection or eye surface healing.

A subject of the invention is also a method for disrupting the quorum sensing of micro-organisms using homoserin lactone substrates to communicate, said method consisting of administering to a patient in need thereof a sufficient amount of composition or pharmaceutical composition comprising the mutated hyperthermophilic PTE having a lactonase activity as defined above.

A subject of the invention is also the use of a mutated hyperthermophilic PTE as defined above, to disrupt quorum-sensing in bacteria.

A subject of the invention is also the use of a mutated hyperthermophilic PTE as defined above, to limit the formation of biofilms, notably in boats or other sea equipments.

A subject of the invention is also the use se of a mutated hyperthermophilic phosphotriesterase as defined above, to inhibit the fire blight in plants or to inhibit the rotting of vegetables.

A subject of the invention is also a phytosanitary composition comprising as active ingredient at least one mutated hyperthermophilic phosphotriesterase as defined above.

A subject of the invention is also an antibacterial composition comprising as active ingredient at least one mutated hyperthermophilic phosphotriesterase as defined above.

The invention is further illustrated by the following examples of the phosphotriesterase of *Vulcanisaeta moutnovskia*, and mutations made to the latter within the context of the preparation of mutated hyperthermophilic PTE having a lactonase activity as defined above according to the invention. These examples are not intended to be limitation of the invention.

EXAMPLES

Example 1

1—Initial Material

VmoLac coding gene is optimized for *Escherichia coli* expression and was synthetized by GeneArt (Life Technologies, France). The gene was subsequently cloned into a custom version of pET22b (Novagen) (pET22b-VmoLac) using XhoI and NdeI as cloning sites. The VmoLac sequence has been verified by sequencing (Sequencing platform, Timone, Marseille, France).

2—Site Directed Mutagenesis

A site saturation of position W264 of VmoLac was ordered to a service provider (Genscript; USA) from the initially used plasmid pET22b-VmoLac. Each variant were checked by sequencing and provided as dried plasmids. The 20 plasmids (pET22b-VmoLac-W264X) have been transformed in *E. coli* BL21(DE3)-pGro7/EL (TaKaRa) by electroporation for activity screening and for high amount production/purification (see concerning section below).

For others site directed mutagenesis or saturation site of selected positions, pfu Turbo polymerase (Agilent) has been used to amplify the overall plasmid using primers incorporating wanted variations. PCR composition has been performed as advised by the provider in a final volume of 50 µL and amplification was performed from 100 ng of plasmid. The PCR protocol was the following:

| 95° C. | 10' | 1× |
|---|---|---|
| 95° C. | 45" | |
| 50° C. | 1' | 30× |
| 68° C. | 15' | |
| 68° C. | 20' | 1× |
| 14° C. | ∞ | 1× |

Remaining initial plasmids were removed by DpnI enzymatic digestion (1 µl; Fermentas) during 45' at 37° C. After inactivation of 20' at 90° C., DNA was purified (QIAquick PCR Purification Kit; Qiagen) to obtain about 30 µL of variable amount of DNA. 5 µL of purified DNA was then transformed into *Escherichia coli* electrocompetent cells (50 µL; *E. cloni*; Lucigen), recovered in 1 mL of SOC medium during 1 h at 37° C. and then plated on agar medium supplemented with ampicillin (100 µg/mL). Several clones were sequenced to verify the well-performed mutagenesis (Sequencing platform, Timone, Marseille, France) and verified plasmids were transformed into *E. coli* strain BL21 (DE₃)-pGro7/GroEL (TaKaRa) for high amount production/purification and analysis (see concerning section below).

TABLE 1

Listing of primers used to create VmoLac variants

| | | |
|---|---|---|
| SEQ ID NO: 208 | L28V Fwd | TGTTTCATGAACATCTGCGTGTTATTACCGAAGTTGTTCGTTG |
| SEQ ID NO: 209 | L28V Rev | CAACGAACAACTTCGGTAATAACACGCAGATGTTCATGAAACA |
| SEQ ID NO: 210 | L28A Fwd | TGTTTCATGAACATCTGCGTGCAATTACCGAAGTTGTTCGTTG |
| SEQ ID NO: 211 | L28A Rev | CAACGAACAACTTCGGTAATTGCACGCAGATGTTCATGAAACA |

TABLE 1 -continued

Listing of primers used to create VmoLac variants

| | | |
|---|---|---|
| SEQ ID NO: 212 | L28G Fwd | TGTTTCATGAACATCTGCGTGGCATTACCGAAGTTGTTCGTTG |
| SEQ ID NO: 213 | L28G Rev | CAACGAACAACTTCGGTAATGCCACGCAGATGTTCATGAAACA |
| SEQ ID NO: 214 | Y100E Fwd | TGGGCACCGGTTTTTATACCGAAACCGAAATCCCGTTCTATTT |
| SEQ ID NO: 215 | Y100E Rev | AAATAGAACGGGATTTCGGTTTCGGTATAAAAACCGGTGCCCA |
| SEQ ID NO: 216 | R224Q Fwd | GTGCATTTATTGGTCTGGATCAGTTTGGCCTGGATATTTATCT |
| SEQ ID NO: 217 | R224Q Rev | AGATAAATATCCAGGCCAAACTGATCCAGACCAATAAATGCAC |
| SEQ ID NO: 218 | W264A Fwd | ATTATTGTCCGACCATTGATGCATATCCGCCTGAAGTTGTGCG |
| SEQ ID NO: 219 | W264A Rev | CGCACAACTTCAGGCGGATATGCATCAATGGTCGGACAATAAT |
| SEQ ID NO: 220 | W264C Fwd | ATTATTGTCCGACCATTGATTGTTATCCGCCTGAAGTTGTGCG |
| SEQ ID NO: 221 | W264C Rev | CGCACAACTTCAGGCGGATAACAATCAATGGTCGGACAATAAT |
| SEQ ID NO: 222 | W264G Fwd | ATTATTGTCCGACCATTGATGGCTATCCGCCTGAAGTTGTGCG |
| SEQ ID NO: 223 | W264G Rev | CGCACAACTTCAGGCGGATAGCCATCAATGGTCGGACAATAAT |
| SEQ ID NO: 224 | W264I Fwd | ATTATTGTCCGACCATTGATATTTATCCGCCTGAAGTTGTGCG |
| SEQ ID NO: 225 | W264I Rev | CGCACAACTTCAGGCGGATAAATATCAATGGTCGGACAATAAT |
| SEQ ID NO: 226 | W264M Fwd | ATTATTGTCCGACCATTGATATGTATCCGCCTGAAGTTGTGCG |
| SEQ ID NO: 227 | W264M Rev | CGCACAACTTCAGGCGGATACATATCAATGGTCGGACAATAAT |
| SEQ ID NO: 228 | W264N Fwd | ATTATTGTCCGACCATTGATAATTATCCGCCTGAAGTTGTGCG |
| SEQ ID NO: 229 | W264N Rev | CGCACAACTTCAGGCGGATAATTATCAATGGTCGGACAATAAT |
| SEQ ID NO: 230 | W264P Fwd | ATTATTGTCCGACCATTGATCCGTATCCGCCTGAAGTTGTGCG |
| SEQ ID NO: 231 | W264P Rev | CGCACAACTTCAGGCGGATACGGATCAATGGTCGGACAATAAT |
| SEQ ID NO: 232 | W264Q Fwd | ATTATTGTCCGACCATTGATCAGTATCCGCCTGAAGTTGTGCG |
| SEQ ID NO: 233 | W264Q Rev | CGCACAACTTCAGGCGGATACTGATCAATGGTCGGACAATAAT |
| SEQ ID NO: 234 | W264S Fwd | ATTATTGTCCGACCATTGATAGCTATCCGCCTGAAGTTGTGCG |
| SEQ ID NO: 235 | W264S Rev | CGCACAACTTCAGGCGGATAGCTATCAATGGTCGGACAATAAT |
| SEQ ID NO: 236 | W264T Fwd | ATTATTGTCCGACCATTGATACCTATCCGCCTGAAGTTGTGCG |
| SEQ ID NO: 237 | W264T Rev | CGCACAACTTCAGGCGGATAGGTATCAATGGTCGGACAATAAT |

TABLE 1 -continued

Listing of primers used to create VmoLac variants

| | | |
|---|---|---|
| SEQ ID NO: 238 | W264V Fwd | ATTATTGTCCGACCATTGATGTTTATCCGCCTGAAGTTGTGCG |
| SEQ ID NO: 239 | W264V Rev | CGCACAACTTCAGGCGGATAAACATCAATGGTCGGACAATAAT |
| SEQ ID NO: 240 | W264Y Fwd | ATTATTGTCCGACCATTGATTATTATCCGCCTGAAGTTGTGCG |
| SEQ ID NO: 241 | W264Y Rev | CGCACAACTTCAGGCGGATAATAATCAATGGTCGGACAATAAT |
| SEQ ID NO: 242 | W264D Fwd | ATTATTGTCCGACCATTGATGATTATCCGCCTGAAGTTGTGCG |
| SEQ ID NO: 243 | W264D Rev | CGCACAACTTCAGGCGGATAATCATCAATGGTCGGACAATAAT |
| SEQ ID NO: 244 | W264E Fwd | ATTATTGTCCGACCATTGATGAATATCCGCCTGAAGTTGTGCG |
| SEQ ID NO: 245 | W264E Rev | CGCACAACTTCAGGCGGATATTCATCAATGGTCGGACAATAAT |
| SEQ ID NO: 246 | W264F Fwd | ATTATTGTCCGACCATTGATTTTATCCGCCTGAAGTTGTGCG |
| SEQ ID NO: 247 | W264F Rev | CGCACAACTTCAGGCGGATAAAAATCAATGGTCGGACAATAAT |
| SEQ ID NO: 248 | W264H Fwd | ATTATTGTCCGACCATTGATCATTATCCGCCTGAAGTTGTGCG |
| SEQ ID NO: 249 | W264H Rev | CGCACAACTTCAGGCGGATAATGATCAATGGTCGGACAATAAT |
| SEQ ID NO: 250 | W264K Fwd | ATTATTGTCCGACCATTGATAAATATCCGCCTGAAGTTGTGCG |
| SEQ ID NO: 251 | W264K Rev | CGCACAACTTCAGGCGGATATTTATCAATGGTCGGACAATAAT |
| SEQ ID NO: 252 | W264L Fwd | ATTATTGTCCGACCATTGATCTGTATCCGCCTGAAGTTGTGCG |
| SEQ ID NO: 253 | W264L Rev | CGCACAACTTCAGGCGGATACAGATCAATGGTCGGACAATAAT |
| SEQ ID NO: 254 | W264R Fwd | ATTATTGTCCGACCATTGATCGTTATCCGCCTGAAGTTGTGCG |
| SEQ ID NO: 255 | W264R Rev | CGCACAACTTCAGGCGGATAACGATCAATGGTCGGACAATAAT |

3. Production & Purification

Pre cultures of selected variants were incubated in 5 mL of LB supplemented with ampicillin (100 µg/mL) and chloramphenicol (34 µg/mL) at 37° C. over night. Production of VmoLac is achieved in 100 mL of ZYP medium supplemented with ampicillin (100 µg/mL) and chloramphenicol (34 µg/mL) seeded using 1 mL of the pre culture. Cells were allowed to grow 5 hours at 37° C. and induced by addition of arabinose (0.2%, w/v) and $CoCl_2$ (0.2 mM), temperature was switched to 25° C. After overnight growth cells were pelleted by centrifugation and resuspended in 2 mL lysis buffer (50 mM HEPES pH 8, 150 mM NaCl, $CoCl_2$ 0.2 mM, Lysozyme 0.25 mg/ml, PMSF 0.1 mM DNAseI 10 µg/ml). Cells were disrupted by freezing/thawing steps and sonication (Ultrasonic cell disruptor XL, Heat-System, USA), cells debris were removed by centrifugation (13 000 g, 4° C., 30'). Partial purification of the protein was performed exploiting VmoLac hyperthermostability by heating 30 minutes at 80° C. Aggregated proteins were removed by centrifugation (13 000 g, 25° C., 30').

4—Screening Procedure 4.1—Phosphotriesterase Activity Screening

Phosphotriesterase activity screening was mediated by monitoring chromophoric phosphotriester hydrolysis using 1 mM paraoxon and parathion (Sigma Aldrich, France). Experiments were performed for 10' monitoring phosphotriester ($\delta_{405\,nm}$=17 000 $M^{-1}\,cm^{-1}$) hydrolysis at 25° C. using a microplate reader (Synergy HT; BioTek, USA) and the Gen5.1 software in a 6.2 mm path length cell for 200 µL reaction in 96-well plate. Standard assays were performed in pte buffer (50 mM HEPES pH 8, 150 mM NaCl, 0.2 mM $CoCl_2$). Assays were made using 100 µL of the partially purified variants.

4.2—Lactonase Activity Screening

Lactonase activity screening was performed in lactonase buffer (2.5 mM Bicine pH 8.3, 150 mM NaCl, 0.2 mM CoCl$_2$, 0.25 mM Cresol purple and 0.5% DMSO) by using Undecanoic-λ-lactone at a 5 mM concentration. Cresol purple (pK$_a$ 8.3 at 25° C.) is a pH indicator (577 nm) used to follow the lactone ring hydrolysis that cause an acidification of the medium. Assays were made using 10 µL of the partially purified variants.

5. Results

Figure 2:
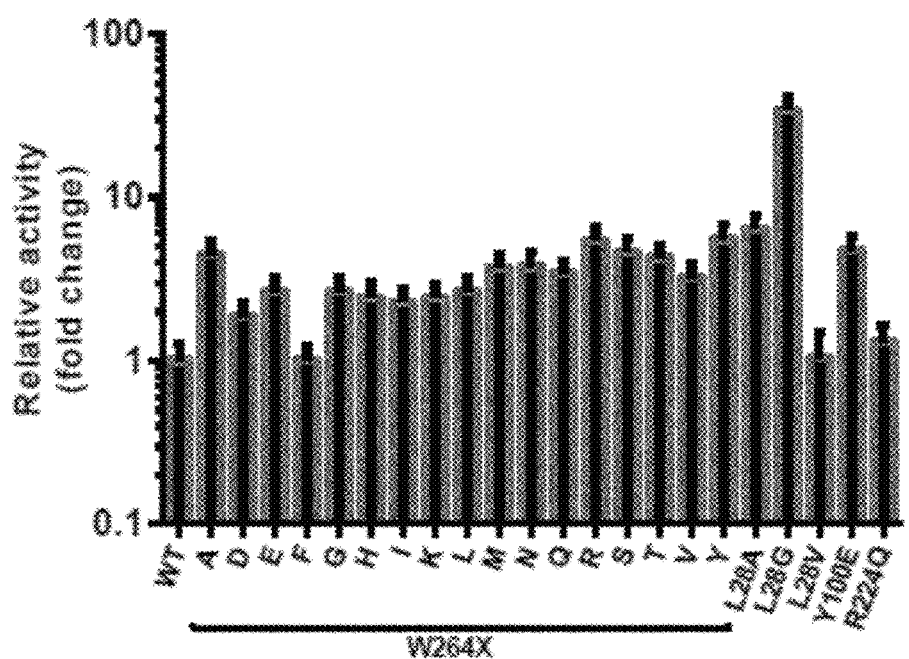
FIG. 2 is a histogram representation of relative activities of VmoLac variants as compared to the wild type enzyme against undecanoic-y-Lactone (5 mM). The Y axis indicates the relative activity (fold change) compared to the wild type (mean values+/−SD).

Each variant was tested against Paraoxon, Parathion and Undecanoic-λ-Lactone. The hydrolysis rates were compared to the wild type enzyme in order to assess variants possessing better hydrolysis potential. No hydrolysis could be detected against parathion. Relative activities are shown in FIGS. 1 and 2.

Example 2

1—Experimental Procedure 1.1—Initial Material

VmoLac coding gene is optimized for *Escherichia coli* expression and was synthetized by GeneArt (Life Technologies, France)[1]. The gene was subsequently cloned into a custom version of pET32b (Novagen) (=pET32b-ΔTrx-VmoLac) NcoI and NotI as cloning sites. The SsoPox sequence has been verified by sequencage (Sequencage plateforme, Timone, Marseille, France). Both plasmids have been used for evolution protocols.

1.2—Site Directed Mutagenesis

A saturation site of position W264 of VmoLac was ordered to service provider (GeneArt, Invitrogen; Germany) from the initially used plasmid pET22b-VmoLac. Each variant were checked by sequencing and provided as *Escherichia coli* DH5α cell glycerol stocks. The 20 plasmids (pET22b-VmoLac-W264X) have been purified from *E. coli* DH5α cells and transformed into BL21(DE$_3$)-pLysS strain by electroporation for activity screening and into BL21(DE3)-pGro7/EL (TaKaRa) for high amount production/purification (see concerning section below).

For others site directed mutagenesis or saturation site of selected positions, pfu Turbo polymerase (Agilent) has been used to amplify the overall plasmid using primers incorporating wanted variations. PCR composition has been performed as advised by the customer in a final volume of 25 µL and amplification was performed from 100 ng of plasmid. The PCR protocol was the following:

| | | |
|---|---|---|
| 95° C. | 10' | 1× |
| 95° C. | 45" | |
| 50° C. | 1' | 30× |
| 68° C. | 15' | |
| 68° C. | 20' | 1× |
| 14° C. | ∞ | 1× |

Remaining initial plasmids were removed by DpnI enzymatic digestion (1 µl; Fermentas) during 45' at 37° C. After inactivation of 20' at 90° C., DNA was purified (QIAquick PCR Purification Kit; Qiagen) to obtain about 30 µL of variable amount of DNA. 5 µL of purified DNA was then transformed into *Escherichia coli* electrocompetent cells (50 µL; *E. cloni*; Lucigen), recovered in 1 mL of SOC medium during 1 h at 37° C. and then plated on agar medium supplemented with ampicillin (100 µg/mL). Several clones were sequenced to verify the well-performed mutagenesis (Sequencage plateforme, Timone, Marseille, France) and verified plasmids were transformed into *E. coli* strain BL21 (DE$_3$)-pGro7/GroEL (TaKaRa) for high amount production/purification and analysis (see concerning section below).

1.3—Directed Evolution Process

Directed evolution protocol has been performed using the GeneMorph® II Random Mutagenesis Kit in 25 µL final, using primers T7-promotor (TAA TAC GAC TCA CTA TAG GG) and T7-RP (GCT AGT TAT TGC TCA GCG G) and 500 ng of matrix (correspond to 6 µg of pET32b-ΔTrx-SsoPox plasmid). Others PCR elements have been performed as advised by the customer recommendations. The PCR protocol was the following:

| | | |
|---|---|---|
| 95° C. | 5' | 1× |
| 95° C. | 30" | |
| 55° C. | 30" | 30× |
| 72° C. | 4' | |
| 72° C. | 10' | 1× |
| 14° C. | ∞ | 1× |

Remaining plasmid was then digested by DpnI enzyme (1 µl; Fermentas) during 45' at 37° C. and then inactivated 20', 90° C. DNA was then purified (QIAquick PCR Purification Kit; Qiagen) to obtain about 50 µL of DNA at 100 ng/µL. For the next steps please refer to part "clonage and bank generation".

1.4—ISOR Method [2]

VmoLac coding gene has been amplified from pET32b-ΔTrx-VmoLac plasmid by PCR (500 µL RedTaq; Sigma) using primers T7-promotor (TAA TAC GAC TCA CTA TAG GG) and T7-RP (GCT AGT TAT TGC TCA GCG G). The PCR protocol was the following:

| | | |
|---|---|---|
| 95° C. | 2' | 1× |
| 95° C. | 30" | |
| 55° C. | 1.5' | 25× |
| 72° C. | 1.2' | |
| 72° C. | 7' | 1× |
| 16° C. | ∞ | 1× |

Remaining plasmid was then digested by DpnI enzyme (1 µl; Fermentas) during 45' at 37° C. and then inactivated 20', 90° C. DNA was then purified (QIAquick PCR Purification Kit; Qiagen) to obtain about 100 µL of DNA at 200 ng/µL. 15 µL of DNA (~3 µg) was digested by 2 UE of DNAseI (TaKaRa) in buffer TrisHCl 100 mM pH 7.5, MnCl$_2$ 10 mM at 20° C. during 30", 1' and 2'. Digestions were stopped by 10' incubation at 90° C. in presence of EDTA 60 mM. After spin down, DNA aliquots were pooled and run on electrophoresis agarose (2%; w/v) gel in TAE buffer during 15' at 50 mA. Fragments consisting of average size of 70 bp (from 50 to 150 pb) were excised from gel and purified using D-Tube™ Dyalizer Maxi (Calbiochem) devices.

DNA extracted from gel (concentration>12 ng/µL) was used as matrix in "assembly PCR" consisting of 100 ng of matrix, 2 pmol of primers incorporating mutations and using 2.5 UE of Pfu Turbo polymerase (Agilent) with a final volume of 25 µl. The primer mix was composed of an oligonucleotide mix consisting of equivalent amount of modified positions. The PCR protocol was the following:

| | | |
|---|---|---|
| 94° C. | 2' | 1× |
| 94° C. | 30" | |
| 65° C. | 1.5' | |
| 62° C. | 1.5' | |
| 59° C. | 1.5' | |
| 56° C. | 1.5' | |
| 53° C. | 1.5' | 35× |
| 50° C. | 1.5' | |

| | | |
|---|---|---|
| 47° C. | 1.5' | |
| 45° C. | 1.5' | |
| 41° C. | 1.5' | |
| 72° C. | 45" | |

| | | |
|---|---|---|
| 72° C. | 7' | 1× |
| 4° C. | ∞ | 1× |

The primer incorporating mutations in the directions 5'-3' are as follows:

TABLE 2

Listings of primers used to create VmoLac variants

| SEQ ID NO | Primer | Sequence 5'-3' |
|---|---|---|
| SEQ ID NO: 136 | G9E-F | GTATTAGCATTGCCGGTGAAAATGAAATTGATCCGGG |
| SEQ ID NO: 137 | G9E-R | CCCGGATCAATTTCATTTTCACCGGCAATGCTAATAC |
| SEQ ID NO: 138 | L28A-F | GTTTCATGAACATCTGCGTGCGATTACCGAAGTTGTTCG |
| SEQ ID NO: 139 | L28A-R | CGAACAACTTCGGTAATCGCACGCAGATGTTCATGAAAC |
| SEQ ID NO: 140 | L68V-F | GTGAAAACCATTATTGATGTGACCGTTGCAGGTATTG |
| SEQ ID NO: 141 | L68V-R | CAATACCTGCAACGGTCACATCAATAATGGTTTTCAC |
| SEQ ID NO: 142 | T69S-F | CCATTATTGATCTGAGCGTTGCAGGTATTGG |
| SEQ ID NO: 143 | T69S-R | CCAATACCTGCAACGCTCAGATCAATAATGG |
| SEQ ID NO: 144 | V77T-F | GTTGCAGGTATTGGTTGTGATACCCGCTTTAATGAAAAAGTTGC |
| SEQ ID NO: 145 | V77T-R | GCAACTTTTTCATTAAAGCGGGTATCACAACCAATACCTGCAAC |
| SEQ ID NO: 146 | Y98W-F | GGGCACCGGTTTTTGGACCTATACCGAAATC |
| SEQ ID NO: 147 | Y98W-R | GATTTCGGTATAGGTCCAAAAACCGGTGCCC |
| SEQ ID NO: 148 | Y100F-F | CCGGTTTTTATACCTTTACCGAAATCCCGTTC |
| SEQ ID NO: 149 | Y100F-R | GAACGGGATTTCGGTAAAGGTATAAAAACCGG |
| SEQ ID NO: 150 | V120I-F | GCCTGGTTGATGCCTTTATTCATGATATTACCATTGG |
| SEQ ID NO: 151 | V120I-R | CCAATGGTAATATCATGAATAAAGGCATCAACCAGGC |
| SEQ ID NO: 152 | I123L-F | GATGCCTTTGTTCATGATCTGACCATTGGTATTCAGGGC |
| SEQ ID NO: 153 | I123L-R | GCCCTGAATACCAATGGTCAGATCATGAACAAAGGCATC |
| SEQ ID NO: 154 | N131P-F | CATTGGTATTCAGGGCACCCCGACCCGTGCAGCATTTG |
| SEQ ID NO: 155 | N131P-R | CAAATGCTGCACGGGTCGGGGTGCCCTGAATACCAATG |
| SEQ ID NO: 156 | D165N-F | GCACATATCAAAACCAATGTTCCGATTATCACCC |
| SEQ ID NO: 157 | D165N-R | GGGTGATAATCGGAACATTGGTTTTGATATGTGC |
| SEQ ID NO: 158 | L227V-F | CTGGATCGTTTTGGCGTGGATATTTATCTGC |
| SEQ ID NO: 159 | L227V-R | GCAGATAAATATCCACGCCAAAACGATCCAG |
| SEQ ID NO: 160 | I229M-F | GATCGTTTTGGCCTGGATATGTATCTGCCGCTGGATAAAC |
| SEQ ID NO: 161 | I229M-R | GTTTATCCAGCGGCAGATACATATCCAGGCCAAAACGATC |
| SEQ ID NO: 162 | Y230S-F | GTTTTGGCCTGGATATTAGCCTGCCGCTGGATAAAC |
| SEQ ID NO: 163 | Y230S-R | GTTTATCCAGCGGCAGGCTAATATCCAGGCCAAAAC |
| SEQ ID NO: 164 | L231P-F | CCTGGATATTTATCCGCCGCTGGATAAACG |
| SEQ ID NO: 165 | L231P-R | CGTTTATCCAGCGGCGGATAAATATCCAGG |
| SEQ ID NO: 166 | C259A-F | CTGCTGAGCCATGATTATGCGCCGACCATTGATTGGTATC |
| SEQ ID NO: 167 | C259A-R | GATACCAATCAATGGTCGGCGCATAATCATGGCTCAGCAG |

TABLE 2 -continued

Listings of primers used to create VmoLac variants

| SEQ ID NO | Primer | Sequence 5'-3' |
|---|---|---|
| SEQ ID NO: 168 | C259L-F | CTGCTGAGCCATGATTATCTGCCGACCATTGATTGGTATC |
| SEQ ID NO: 169 | C259L-R | GATACCAATCAATGGTCGGCAGATAATCATGGCTCAGCAG |
| SEQ ID NO: 170 | I262F-F | GATTATTGTCCGACCTTTGATTGGTATCCGC |
| SEQ ID NO: 171 | I262F-R | GCGGATACCAATCAAAGGTCGGACAATAATC |
| SEQ ID NO: 172 | W264L-F | GATTATTGTCCGACCATTGATCTGTATCCGCCTGAAGTTGTGC |
| SEQ ID NO: 173 | W264L-R | GCACAACTTCAGGCGGATACAGATCAATGGTCGGACAATAATC |
| SEQ ID NO: 174 | W264M-F | GATTATTGTCCGACCATTGATATGTATCCGCCTGAAGTTGTGC |
| SEQ ID NO: 175 | W264M-R | GCACAACTTCAGGCGGATACATATCAATGGTCGGACAATAATC |
| SEQ ID NO: 176 | W264C-F | CCGACCATTGATTGCTATCCGCCTGAAG |
| SEQ ID NO: 177 | W264C-R | CTTCAGGCGGATAGCAATCAATGGTCGG |
| SEQ ID NO: 178 | W264F-F | CCGACCATTGATTTTTATCCGCCTGAAGTTGTGCG |
| SEQ ID NO: 179 | W264F-R | CGCACAACTTCAGGCGGATAAAAATCAATGGTCGG |
| SEQ ID NO: 180 | W264A-F | GTCCGACCATTGATGCGTATCCGCCTGAAG |
| SEQ ID NO: 181 | W264A-R | CTTCAGGCGGATACGCATCAATGGTCGGAC |
| SEQ ID NO: 182 | T273P-F | GAAGTTGTGCGTAGCCCGGTTCCGGATTGGAC |
| SEQ ID NO: 183 | T273P-R | GTCCAATCCGGAACCGGGCTACGCACAACTTC |
| SEQ ID NO: 184 | V274T-F | GAAGTTGTGCGTAGCACCACCCCGGATTGGACCATGAC |
| SEQ ID NO: 185 | V274T-R | GTCATGGTCCAATCCGGGGTGGTGCTACGCACAACTTC |
| SEQ ID NO: 186 | M279T-F | GTTCCGGATTGGACCACCACCCTGATTTTTGAG |
| SEQ ID NO: 187 | M279T-R | CTCAAAAATCAGGGTGGTGGTCCAATCCGGAAC |
| SEQ ID NO: 188 | L281M-F | CCGGATTGGACCATGACCATGATTTTTGAG |
| SEQ ID NO: 189 | L281M-R | CTCAAAAATCATGGTCATGGTCCAATCCGG |
| SEQ ID NO: 190 | T296S-F | GCGTAGCGAAGGTATTAGCGAAGAACAAATTAATCGC |
| SEQ ID NO: 191 | T296S-R | GCGATTAATTTGTTCTTCGCTAATACCTTCGCTACGC |

Finally, assembly PCR was used as matrix for "nested PCR". 1 µL of assembly PCR was used as classical PCR (50 µL, RedTaq; Sigma) with cloning primers VmoLac-lib-pET-5'(ATGCGCATTCCGCTGGTTGG) and VmoLac-lib-pET-3' (TTATTAGCTAAAGAATTTTTTCGGATTTTC). The PCR protocol was the following:

| 95° C. | 2' | 1× |
|---|---|---|
| 95° C. | 30" | 25× |
| 65° C. | 1.5' | |
| 72° C. | 7' | 1× |
| 16° C. | ∞ | 1× |

1.5—Clonage and Bank Generation

PCR product has been purified using extraction kit (QIAquick PCR Purification Kit; Qiagen) and then digested for 45' at 37° C. by NcoI Fastdigest and NotI Fastdigest enzymes (12UE of each enzyme; Fermentas). Enzymes were then inactivated by 20' incubation at 90° C. and then purified (QIAquick PCR Purification Kit; Qiagen) to be cloned into pET32b-Δtrx plasmid at the corresponding restriction sites previously dephosphorylated as recommended by the customer (10 UE/µl CIP; NEB). Ligation has been performed in a molar ratio 1:3 with 50 ng of plasmid using T4-DNA ligase during 16 h at 16° C. (20 UE; NEB).

After ligation, ligase was inactivated 20' at 90° C. and then purified from salts by classical alcohol precipitation and recovered in 10 µL of water. *Escherichia coli* electrocompetent cells (50 µL; *E. cloni*; Lucingen) were electroporated with 5 µL of purified ligation and recovered in 1 mL of SOC medium for 1 h at 37° C. All 1 mL was then plated on agar selected medium (ampicillin 100 µg/mL) and incubated overnight at 37° C.

Obtaining transformation efficiency higher than $10^4$ colonies on agar plate, the colonies were then harvested using 1 mL of plasmidic extraction kit solution 1 (Qiaprep Spin Miniprep kit; Quiagen) and plasmids were then extracted from cells following the recommended procedure. The plasmid pool obtained constituting the bank, 100 ng were used to electroporate 50 µL of electrocompetent BL21(DE3)-pGro7/EL (TaKaRa). After 1 h of recovering in SOC medium at 37° C., cells were plated on agar plate added of ampicillin (100 µg/mL) and chloramphenicol (37 µg/mL).

2—Screening Procedure

Microcultures consisting of 600 µL of ZYP medium [3,4] supplemented by ampicillin (100 g/mL) and chloramphenicol (34 µg/mL) are inoculated by a tip picked colony in 96 well plates. Cultures grew at 37° C. under 1 600 rpm agitation for 5 h before activation mediated by temperature transition to 25° C. and addition of $CoCl_2$ (0.2 mM) and arabinose (0.2%, w/v). After overnight growth, tips were removed and used to pick separated colony on agar plate (ampicilin 100 µg/mL; chloramphenicol 34 µg/mL) for strain conservation. Cultures were centrifuged to keep cell pellets which were resuspended in lysis buffer consisting of 50 mM HEPES pH 8, 150 mM NaCl, $CoCl_2$ 0.2 mM, Lysozyme 0.25 mg/ml, PMSF 0.1 mM DNAseI 10 µg/ml and $MgSO_4$ 20 mM. Cells were disrupted by freezing/thawing steps and cells debris were removed by centrifugation (13 000 g, 4° C., 30'). Partial purification of the protein was performed exploiting VmoLac hyperthermostability [5] by 15 minutes incubation at 70° C. Aggregated proteins were harvested by centrifugation (13 000 g, 25° C., 30').

2.1—Phosphotriesterase Activity Screening

Phosphotriesterase activity screening was mediated by monitoring chromophoric phosphotriester hydrolysis (paraoxon, methyl-paroxon, parathion, methyl parathion (1 mM or 100 µM, Fluka). Kinetics experiments were performed for 10' monitoring phosphotriester ($\varepsilon_{405\ nm}$=17 000 $M^{-1}$ $cm^-$) hydrolysis at 25° C. using a microplate reader (Synergy HT; BioTek, USA) and the Gen5.1 software in a 6.2 mm path length cell for 200 µL reaction in 96-well plate. Standard assays were performed in pte buffer (50 mM HEPES pH 8, 150 mM NaCl, 0.2 mM $CoCl_2$).

2.2—Lactonase Activity Screening

Lactonase activity screening was mediated by a genetically modified strain POA1 of *Pseudomonas aeruginosa* (PAO1-ΔlasI-JP2). The JP2 plasmid encodes proteins coding for bioluminescence production in presence of 3-oxo-C12 AHLs in *P. aeruginosa*; the lasI gene, responsible of 3-oxo-C12 AHLs synthesis in wt *P. aeruginosa*, is deleted. SsoPox variants (5 µL of tenfold diluted partially purified variants) are mixed in 100 µL of pte buffer with 3-oxo-C12 AHL (100 nM) and incubated 20 minutes at room temperature. A volume of 450 µL of LB media (Trimethoprime lactate 300 µg/mL) was inoculated by overnight preculture of *P. aeruginosa* PAO1-ΔlasI-JP2 (1/50) and supplemented with the mixture protein/AHLs (50 µL). The final theoretical concentration of 3-oxo-C12 AHLs is 20 nM, prior to enzymatic hydrolysis by VmoLac. After 270 minutes of culture at 37° C., cell density ($OD_{600\ nm}$) and bioluminescence (460-40 nm; intensity 100) of 200 µL aliquots of culture are measured in a 96-well plate using a microplate reader (Synergy HT, BioTek, USA) monitored by Gen5.1 software. Controls consist in the same experiment without enzyme and/or without AHLs.

Best hits were re-plated and then placed in microcultures as previously explained despite each clones were represented four times. The previous protocol was performed as identic to confirm the results. However, lysis buffer and pte buffer doesn't contain $CoCl_2$ salt to avoid affinity loss for the metals by the enzyme during the improvement process.

3—Improvement Confirmation and Analysis

The best variants were then sequenced (Sequencage plateforme, Timone, Marseille, France) and produce in larger amount for catalytic properties analysis. Genes or plasmids selected for the best improvement can have been used to perform the next round of diversity generation (i.e. go back to the first sections).

The high amount of protein production was performed using *E. coli* strain BL21($DE_3$)-pGro7/GroEL (TaKaRa). Productions have been performed in 500 mL of ZYP medium [3] (100 µg/ml ampicilline, 34 µL/g/ml chloramphenicol) as previously explained [4,6,7], 0.2% (w/v) arabinose (Sigma-Aldrich; France) was added to induce the expression of the chaperones GroEL/ES and temperature transition to 25° C. was perfomed. Purification was performed as previously explained [7]. Briefly, a single step of 30' incubation at 70° C. was performed, followed by differential ammonium sulfate precipitation, dialysis and exclusion size chromatography. Proteins were quantified using nanospectrophotometer (nanodrop, thermofisher scientific, France) using protein molar extinction coefficient generated using protein primary sequence in PROT-PARAM (expasy tool softwares)[8].

3.1—Kinetics Generalities

Catalytic parameters were evaluated at 25° C., and recorded with a microplate reader (Synergy HT, BioTek, USA) and the Gen5.1 software in a 6.2 mm path length cell for 200 µL reaction in 96-well plate as previously explained [6]. Catalytic parameters were obtained by fitting the data to the Michaelis-Menten (MM) equation [9] using Graph-Pad Prism 5 software. When $V_{max}$ could not be reached in the experiments, the catalytic efficiency was obtained by fitting the linear part of MM plot to a linear regression using Graph-Pad Prism 5 software.

3.2—Phosphotriesterase Activity Characterization

Standard assays were performed in pte buffer measuring time course hydrolysis of PNP derivative of OPs ($\varepsilon_{405\ nm}$=17 000 $M^{-1}$ $cm^{-1}$), nerve agents coumarin derivatives (CMP-coumarin, IMP-coumarin, PinP-coumarin)[10]($\varepsilon_{412\ nm}$=37 000 $M^{-1}$ $cm^{-1}$) or malathion bu adding 2 mM DTNB in the buffer ($\varepsilon_{412\ nm}$=13 700 $M^{-1}$ $cm^{-1}$). Kinetics have also been performed in pte buffer added of 0.1 and/or 0.01% of SDS as previously exemplified [1].

3.3—Lactonase Activity Characterization

The lactonase kinetics were performed using a previously described protocol [6]. The time course hydrolysis of lactones were performed in lac buffer (Bicine 2.5 mM pH 8.3, NaCl 150 mM, $CoCl_2$ 0.2 mM, Cresol purple 0.25 mM and 0.5% DMSO) over a concentration range 0-2 mM for AHLs. Cresol purple ($pK_a$ 8.3 at 25° C.) is a pH indicator used to follow lactone ring hydrolysis by acidification of the medium. Molar coefficient extinction at 577 nm was evaluated recording absorbance of the buffer over an acetic acid range of concentration 0-0.35 mM.

REFERENCES

1. Hiblot J, Gotthard G, Chabriere E, Elias M (2012) Characterisation of the organophosphate hydrolase catalytic activity of SsoPox. Sci Rep 2: 779.
2. Herman A, Tawfik D S (2007) Incorporating Synthetic Oligonucleotides via Gene Reassembly (ISOR): a versatile tool for generating targeted libraries. Protein Eng Des Sel 20: 219-226.
3. Studier F W (2005) Protein production by auto-induction in high density shaking cultures. Protein Expr Purif 41: 207-234.
4. Gotthard G, Hiblot J, Elias M, Chabriere E (2011) Crystallization and preliminary X-ray diffraction analysis of the hyperthermophilic *Sulfolobus islandicus* lactonase. Acta Crystallogr Sect F Struct Biol Cryst Commun 67: 354-357.
5. Del Vecchio P, Elias M, Merone L, Graziano G, Dupuy J, et al. (2009) Structural determinants of the high thermal stability of SsoPox from the hyperthermophilic archaeon *Sulfolobus solfataricus*. Extremophiles 13: 461-470.
6. Hiblot J, Gotthard G, Chabriere E, Elias M (2012) Structural and Enzymatic characterization of the lactonase SisLac from *Sulfolobus islandicus*. PLoS One 7: e47028.
7. Hiblot J, Gotthard G, Chabriere E, Elias M (2012) Characterisation of the organophosphate hydrolase catalytic activity of SsoPox. Sci Rep 2.
8. Gasteiger E, Hoogland C, Gattiker A, Duvaud S, Wilkins M R, et al. (2005) Protein Identification and Analysis Tools on the ExPASy Server. In: Walker J M, editor. The proteomics protocols handbook: Humana Press.
9. Copeland R A (2000) Enzymes, A Practical Introduction to Structure, Mechanism, and Data Analysis. New York, Chichester, Weiheim, Brisbane, Singapore, Toronto: WILEY-VCH. 390.
10. Ashani Y, Gupta R D, Goldsmith M, Silman I, Sussman J L, et al. (2010) Stereo-specific synthesis of analogs of nerve agents and their utilization for selection and characterization of paraoxonase (PON1) catalytic scavengers. Chem Biol Interact 187: 362-369.

The invention claimed is:

1. A mutated hyperthermophilic phosphotriesterase (PTE) having a lactonase activity derived from a hyperthermophilic PTE corresponding to the sequence of SEQ ID NO: 1 or having at least 70% identity to the amino acid sequence of SEQ ID NO: 1,
    said mutated PTE comprising at least one mutation selected from the group consisting of:
        substitution of the valine L in position 29,
        substitution of the tyrosine Y in position 99,
        substitution of the tyrosine Y in position 101,
        substitution of the arginine R in position 225,
        substitution of the tryptophane W in position 265, of SEQ ID NO: 1 by any other natural or non-natural amino acid.

2. The mutated hyperthermophilic PTE having a lactonase activity according to claim 1, said mutated hyperthermophilic PTE being derived from a hyperthermophilic PTE of *Vulcanisaeta moutnovskia* corresponding to the sequence of SEQ ID NO: 3 or having at least 70% identity to the amino acid sequence of SEQ ID NO: 3,
    said SEQ ID NO: 3 corresponding to SEQ ID NO: 1 in which the amino acid in position 2 is missing,
    said mutated PTE comprising at least one mutation selected from the group consisting of:
        substitution of the valine L in position 28,
        substitution of the tyrosine Y in position 98,
        substitution of the tyrosine Y in position 100,
        substitution of the arginine R in position 224,
        substitution of the tryptophane W in position 264, of SEQ ID NO: 3 by any other natural or non-natural amino acid.

3. The mutated hyperthermophilic PTE having a lactonase activity according to claim 1, said mutated PTE having at least 70% identity to the amino acid sequence SEQ ID NO: 3.

4. The mutated hyperthermophilic PTE having a lactonase activity according to claim 1, wherein said mutated hyperthermophilic PTE having a lactonase activity possesses: a greater phosphotriesterase activity, and/or a greater lactonase activity, than that of the non-mutated hyperthermophilic PTE having a lactonase activity from which they derived.

5. The mutated hyperthermophilic PTE having a lactonase activity according to claim 2, wherein the at least one mutation is selected from the group consisting of:
    substitution of the leucine L in position 28 by a non-bulky amino acid selected from the group consisting of G, P, I, A, D, C, S, T, and N or by a hydrophobic amino acid selected from the group consisting of V, I, M, F, G, A, P, W, Y, and C,
    substitution of the tyrosine Y in position 98 by a bulky amino acid selected from the group consisting of E, H, K, R, Q, W, F, and M or by a hydrophobic amino acid selected from the group consisting of V, I, L, M, F, G, A, P, W, and C,
    substitution of the tyrosine Y in position 100 by a bulky amino acid selected from the group consisting of E, H, K, R, Q, W, F, and M or by a hydrophobic amino acid selected from the group consisting of V, I, L, M, F, G, A, P, W, and C,
    substitution of the arginine R in position 224 by a non-bulky amino acid selected from the group consisting of G, P, L, I, V, A, D, C, S, T, and N or by a polar amino acid selected from the group consisting of W, Y, S, T, C, Q, N, K, H, D, and E,
    substitution of the tryptophane W in position 264 by a hydrophobic amino acid selected from the group consisting of V, I, L, M, F, G, A, P, Y, and C or by a non-bulky amino acid selected from the group consisting of G, P, L, I, V, A, C, S, T, and N.

6. The mutated hyperthermophilic PTE having a lactonase activity according to claim 2, wherein the at least one mutation is selected from the group consisting of:
    substitution of the leucine L in position 28 by an amino acid selected from the group consisting of A, G, and V,
    substitution of the tyrosine Y in position 100 by an amino acid E,
    substitution of the arginine R in position 224 by an amino acid Q,
    substitution of the tryptophane W in position 264 by an amino acid selected from the group consisting of A, C, G, I, M, N, P, Q, R, S, T, V, Y, D, E, H, K, L, and F.

7. The mutated hyperthermophilic PTE having a lactonase activity according to claim 2, wherein the at least one mutation is a single substitution of the leucine L in position 28 by an amino acid selected from the group consisting of A, C, G, I, M, N, P, Q, R, S, T, V, Y, D, E, H, K, W, and F.

8. The mutated hyperthermophilic PTE having a lactonase activity according to claim 2, wherein the at least one mutation is a single substitution of the tyrosine Y in position 98 by an amino acid selected from the group consisting of A, C, G, I, M, N, P, Q, R, S, T, V, W, D, E, H, K, L, and F.

9. The mutated hyperthermophilic PTE having a lactonase activity according to claim 2, wherein the at least one mutation is a single substitution of the tyrosine Y in position 100 by an amino acid selected from the group consisting of A, C, G, I, M, N, P, Q, R, S, T, V, W, D, E, H, K, L, and F.

10. The mutated hyperthermophilic PTE having a lactonase activity according to claim 2, wherein the at least one mutation is a single substitution of the arginine R in position 224 by an amino acid selected from the group consisting of A, C, G, I, M, N, P, Q, W, S, T, V, Y, D, E, H, K, L, and F.

11. The mutated hyperthermophilic PTE having a lactonase activity according to claim 2, wherein the at least one mutation is a single substitution of the tryptophane W in position 264 by an amino acid selected from the group consisting of A, C, G, I, M, N, P, Q, R, S, T, V, Y, D, E, H, K, L, and F.

12. The mutated hyperthermophilic PTE having a lactonase activity according to claim 2, wherein said mutated hyperthermophilic PTE is selected from the group consisting of: SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 192, SEQ ID NO: 193, SEQ ID NO: 194, SEQ ID NO: 195, SEQ ID NO: 196, SEQ ID NO: 197, SEQ ID NO: 198, SEQ ID NO: 199, SEQ ID NO: 200, SEQ ID NO: 201, SEQ ID NO: 202, SEQ ID NO: 203, SEQ ID NO: 204, SEQ ID NO: 205, SEQ ID NO: 206, and SEQ ID NO: 207.

13. A pharmaceutical composition comprising as active ingredient at least one mutated hyperthermophilic PTE having a lactonase activity as defined in claim 1 in combination with a pharmaceutically acceptable vehicle.

14. The pharmaceutical composition as defined in claim 13 for use in the treatment of bacterial infections caused by bacteria using homoserin lactone substrates to communicate, in particular in the blood, wounds, burn, skin, biomaterial-body contact area, or for use in the treatment of eyes infection or eye surface healing.

15. An antibacterial composition comprising as active ingredient at least one mutated hyperthermophilic phosphotriesterase as defined in claim 1.

* * * * *